United States Patent
Borodina et al.

(10) Patent No.: US 11,434,506 B2
(45) Date of Patent: *Sep. 6, 2022

(54) PRODUCTION OF DESATURATED FATTY ALCOHOLS AND DESATURATED FATTY ALCOHOL ACETATES IN YEAST

(71) Applicant: Danmarks Tekniske Universitet, Kgs. Lyngby (DK)

(72) Inventors: Irina Borodina, Nivå (DK); Carina Holkenbrink, Kongens Lyngby (DK); Marie Inger Dam, Birkerød (DK); Christer Löfstedt, Lund (SE); Baojian Ding, Södra Sandby (SE); Hong-Lei Wang, Lund (SE)

(73) Assignee: Danmarks Tekniske Universitet, Kgs. Lyngby (DK)

(*) Notice: Subject to any disclaimer, the term of this patent is extended or adjusted under 35 U.S.C. 154(b) by 0 days.

This patent is subject to a terminal disclaimer.

(21) Appl. No.: 16/468,784

(22) PCT Filed: Dec. 15, 2017

(86) PCT No.: PCT/EP2017/083030
§ 371 (c)(1),
(2) Date: Jun. 12, 2019

(87) PCT Pub. No.: WO2018/109167
PCT Pub. Date: Jun. 21, 2018

(65) Prior Publication Data
US 2020/0102582 A1    Apr. 2, 2020

(30) Foreign Application Priority Data
Dec. 16, 2016 (EP) .................... 16204783

(51) Int. Cl.
| | | |
|---|---|---|
| *C12N 9/02* | (2006.01) | |
| *C12N 9/10* | (2006.01) | |
| *C12N 9/20* | (2006.01) | |
| *C12P 7/64* | (2022.01) | |
| *C12P 7/04* | (2006.01) | |
| *C12N 1/16* | (2006.01) | |

(52) U.S. Cl.
CPC ............ *C12P 7/04* (2013.01); *C12N 1/16* (2013.01); *C12N 9/001* (2013.01); *C12N 9/0071* (2013.01); *C12Y 103/01086* (2013.01); *C12Y 114/19001* (2013.01)

(58) Field of Classification Search
CPC ........ C12P 7/6409; C12P 7/64; C12P 7/6427; C12P 7/00; C12N 9/16; C12N 9/0008; C12N 15/79; C12N 9/0004; C12N 15/63; C12Y 301/02014
USPC ......... 435/134, 136, 167, 255.1, 252.2, 189, 435/233, 195
See application file for complete search history.

(56) References Cited

U.S. PATENT DOCUMENTS

| | | |
|---|---|---|
| 5,876,994 A | 3/1999 | Knipple et al. |
| 8,323,935 B2 | 12/2012 | Xue et al. |
| 9,157,103 B2 | 10/2015 | Hattendorf et al. |
| 2012/0165562 A1 | 6/2012 | Hattendorf et al. |

FOREIGN PATENT DOCUMENTS

| | | |
|---|---|---|
| CN | 102795997 A | 11/2012 |
| EP | 2655612 B1 | 7/2017 |
| WO | 200062792 A2 | 10/2000 |
| WO | 03074715 A2 | 9/2003 |
| WO | 2004031395 A1 | 4/2004 |
| WO | 2012087958 A2 | 6/2012 |
| WO | 2013096082 A1 | 6/2013 |
| WO | 2015013674 A2 | 1/2015 |
| WO | 2015057155 A1 | 4/2015 |
| WO | 2015171057 A1 | 11/2015 |
| WO | 2016207339 A1 | 12/2016 |
| WO | 2017087846 A1 | 5/2017 |

OTHER PUBLICATIONS

Devos et al., Proteins Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Li et al. (J. Compu. and struct. Boil. 2016, 14, pp. 341-349. (Year: 2016).*
Moraes et al. Biology 2021, 10(245), pp. 1-4. (Year: 2021).*
Reis et al. Biochem Soc Trans. 2019, 47, pp. 47-61. (Year: 2019).*
Machine English translation of CN102795997A.
Rodriguez, G. et al., Expanding ester biosynthesis in *Escherichia coli*, Nat Chem Biol., 10(4): 259-265, Apr. 2014.
Bjostad, L. et al., Biosynthesis of Sex Pheromone Components and Glycerolipid Precursors From Sodium [lj4c] Acetate In Redbanded Leafroller Moth, Journal of Chemical Ecology, 10(4): 681-691, 1984.
Bari, M.A.; "Development of pheromone mating disruption strategies for the suppression of the artichoke plume moth in artichokes grown on the central coast of California"; Proc. of Vth IC of Artichoke; Ed. F.J.Sanz Villar, Acta Hort, 660, pp. 523-527; 2002.
Dunkelblum et al.: "Identification of the sex pheromone of the cotton bollworm, *Heliothis armigera*, inIsrael", Phytoparasitica 8, 209-211 (1980).
Fujii et al.: "Molecular Cloning, Sequence Analysis, and Expression of the Yeast Alcohol Acetyltransferase Gene", Applied and Environmental Microbiology, Aug. 1994, p. 2786-2792.

(Continued)

*Primary Examiner* — Robert B Mondesi
*Assistant Examiner* — Mohammad Y Meah
(74) *Attorney, Agent, or Firm* — Dinsmore & Shohl

(57) ABSTRACT

The present invention relates to the production of compounds comprised in pheromones, in particular moth pheromones, such as desaturated fatty alcohols and desaturated fatty alcohol acetates and derivatives thereof, from a yeast cell.

18 Claims, 4 Drawing Sheets
Specification includes a Sequence Listing.

(56) References Cited

OTHER PUBLICATIONS

Kehat et al.: "Behavioral responses of male Heliothis armigera (Lepidoptera: noctuidae) moths in a flight tunnel to combinations of components identified from female sex pheromone glands", Journal of Insect Bhavior, 3(1):75-83, 1990.
Knipple et al.: "Cloning and functional expression of a cDNA encoding a pheromone gland-specific acyl-CoA D11-desaturase of the cabbage looper moth, Trichoplusia ni", Proc. Natl. Acad. Sci. USA, vol. 95, pp. 15287-15292, Dec. 1998, Biochemistry.
Knoll et al.: "Biochemical Studies of Three Saccharomyces cerevisiaeAcyl-CoA Synthetases, Faalp, FaaZp, and Faa3p", The journal of Biological Chemist, vol. 269, No. 23, Issue of Jun. 10,pp. 16348-16356, 1994.
Moto et al.: "Pheromone gland-specific fatty-acyl reductase of the silkmoth, Bombyx mori", 9156-9161 PNAS, Aug. 5, 2003, vol. 100, No. 16.
Nesbitt et al.: (Z)-9-Hexadecenal: a minor component of the female sex pheromone of Heliothis armigera (Hübner) (Lepidoptera, Noctuidae). Entomol. Exp. Appl. 27, 306-308 (1980).
Zhang et al.: "An overlooked component: (Z)-9-tetradecenal as a sex pheromone in Helicoverpa armigera", J. Insect Physiol. 58, 1209-1216 (2012).
Roelofs, W. et al., Molecular genetics and evolution of pheromone biosynthesis in Lepidoptera, PNAS, 10016): 9179-9184, Aug. 5, 2003.
Ando, T. et al.; "LepidopteranSex Pheromone, Topics in Current Chemistry"; 239: pp. 51-96; Year: 2004.
Gatter, M.; "A newly identified fatty alcohol oxidase gene is mainly responsible for the oxidation of long-chain x-hydroxy fatty acids in Yarrowia lipolytica", FEMS Yeast Res 14, 858-872; Year: 2014.
Heath, R. et al., "Periodicity of Female Sex Pheromone Titer and Release in Heliothis subflexa and H. virescens (Lepidoptera: Noctuidae)", Annals of the Entomological Society of America, 84:2; pp. 182-189; Year: 1991.
Lee, S. et al., "Sex pheromone composition if the diamondback moth Plutella xylostella in Korea", J. Asia-Pacific Entomol., 8(3), pp. 243-248; Year: 2005.
Rosenfield, C-L. et al., "Structural and functional conservation and divergence among acyl-CoA desaturases of two noctuid species, the corn earworm, Helicoverpa zea1, and the cabbage looper, Trichoplusia ni", Insect Biochemistry and Molecular Biology, vol. 31, pp. 949-964; Year: 2001.
Sheng, J. et al., Metabolic engineering of yeast to produce fatty acid-derived biofuels: bottlenecks and solutions, Frontiers in Microbiology; vol. 6, pp. 1-11; Year: 2015.
Suckling, D.M. et al.; "Improving the Pheromone Lure for Diamondback Moth", New Zealand Plant Protection, vol. 55, pp. 182-187: Year: 2002.
Bao-Jian Ding, et al.; Nature Communications; vol. 5; 2014; DOI: 10.1038/ncomms4353.
Alfaro, et al.; Crop Protection, vol. 28; pp. 567-572, 2009.
Angerer, et al.; PNAS, vol. 111, No. 14, pp. 5207-5212; 2014.
Antony, et al.; Scientific Reports, vol. 6, No. 29927; DOI: 10.1038/srep29927, 2016.
Bari, M.A.; "Development of pheromone mating disruption strategies for the suppression of the artichoke plume moth in artichokes grown on the central coast of California"; pp. 523-527; 2003.
Chen, et al.; Appl Microbiol Biotechnol; vol. 48, pp. 232-235, 1997.
Dallerac, et al.; PNAS, vol. 97, No. 17; pp. 9449-9454, Aug. 15, 2000.
Ding,; Lund: Lund University, Faculty of Science, Department of Biology; pp. 1-34; 2014.
Ding, Baojian & Lofstedt, Christer; BMC Genomics, vol. 16; DOI 10.1186/s12864-015-1909-2; 2015.
Ding, et al.; Lipids; vol. 51, pp. 469-475; 2016.
Eizaguirre, et al.; Use of pheromones and other semiochemicals in integrated production, IOBC wprs Bulletin; vol. 25, pp. 1-10; 2002.
Feng, et al.; Metabolic Engineering, vol. 27, pp. 10-19; 2015.
Ferrell, William J. and Yao, Kuo-Ching; J Lipid Res., vol. 13, pp. 23-26; 1972.
Fickers, et al.; FEMS Yeast Research, vol. 5, pp. 527-543; 2005.
Gietz, R. Daniel and Schiestl, Robert H.; Nat Protoc., vol. 2, No. 1, pp. 31-34, 2007.
Gietz, R. Daniel and Schiestl, Robert H.; Nat Protoc., vol. 2, No. 1; pp. 35-37; 2007.
Suerful et al.; Microbial Cell Factories; vol. 12, No. 122; 2013.
Hagstrom, et al.; Microbial Cell Factories; vol. 12, pp. 1-11; 2013.
Iwama, et al.; FEMS Yeast Res.; vol. 15, No. 3; doi: 10.1093/femsyr/fov014; 2015.
Iwama, et al.; J Biol Chem., vol. 289, No. 48; pp. 33275-33286, 2014.
Jensen, et al.; FEMS Yeast Res., vol. 14, No. 2; pp. 238-248; 2014.
Jessop-Fabre, et al.; Biotechnol J., vol. 11, No. 8; pp. 1110-1117; 2016.
Kehat, Moshe and Dunkelblum, Ezra; Archives of Insect Biochemistry and Physiology, vol. 22, pp. 425-431; 1993.
Knipple, et al.; Genetics, vol. 162, pp. 1737-1752; 2002.
Li, et al.; Synthesis, No. 7, pp. 1163-1169; 2009.
Maury, et al.; PLoS One, vol. 11, No. 3; doi:10.1371/journal.pone. 0150394; 2016.
Meyer et al.; J. Org. Chern., vol. 59, pp. 7549-7552; 1994.
Mitchell et al.; Journal of Economic Entomology, vol. 75, No. 2, pp. 270-274; 1982.
Okada, et al.; ChemInform, vol. 45(33), one page; DOI: 10.1002/chin.201433042; 2014.
Schneiter, et al.; J. Bacteriol., vol. 182, No. 13 pp. 3655-3660; 2000.
Sheng, et al.; Frontiers in Microbiology, Article 554, vol. 6; doi: 10.3389/fmicb.2015.00554; 2015.
Steves, et al.; J. Am. Chem. Soc., vol. 135, pp. 15742-15745; 2013.
Stovicek, et al.; J Ind Microbiol Biotechnol, vol. 42, pp. 1519-1531; 2015.
Sumita, et al.; FEMS Microbiol Lett., vol. 214, pp. 31-38; 2002.
Tamura, et al.; Synlett, vol. 23, pp. 1397-1407; 2012.
Tumlinson, et al.; Journal of Chemical Ecology, vol. 12, No. 9, 1986.
Wang, et al.; Biotechnology for Biofuels, vol. 9, No. 1; DOI 103.1186/s13068-016-0512-3; 2016.
Wu, et al.; Insect Science, vol. 19, pp. 643-648; DOI 10.1111/j.1744-7917.2011.01497.x; 2012.
Yadav et al.; Tetrahedron, vol. 60, pp. 2131-2135; 2004.
XP-002750785; Database UniProt—2014, one page.
XP-002750785; Database UniProt—2013, one page.
Zhang, Y. et al., Identification and Expression Profiles of Sex Pheromone Biosynthesis and Transport Related Genes in Spodoptera litura, PLoS ONE 10(10): e0140019, 2015.
Liu, et al. "Desaturases from the spotted fireworm moth (Choristoneura parallela) shed light on the evolutionary origins of novel moth sex pheromone desaturases." Gene 342: 303-311 (2004).
Hao, et al. "Characterization of Z/E11- and Z9-desaturases from the obliquebanded leafroller moth, Choristoneura roseaceana." J. Insect Sci. 2:26 (2002).
Jurenka, R., Insect Pheromone Biosynthesis, Topics in Current Chemistry, 239: 97-132, 2004.

* cited by examiner

A pex20 term. Dmd9 GPD Prom. TefI Prom. HarFAR lip2 term.

B

Tefintron Atf1 pex20 term.

C

TDH3 prom. ADH1 term.

D

Pex20 term. Atf1 GPD Prom. TefI Prom. HarFAR Lip2 term.

E

F

G

PRODUCTION OF DESATURATED FATTY ALCOHOLS AND DESATURATED FATTY ALCOHOL ACETATES IN YEAST

CROSS REFERENCE TO RELATED APPLICATIONS

This application is a U.S. national stage of PCT/EP2017/083030 filed Dec. 15, 2017, which claims priority to European Application No: 16204783.1 filed Dec. 16, 2016, the contents of each of which are incorporated herein by reference.

This application incorporates by reference a Sequence Listing with this application as an ASCII text file entitled "16DMTU-H070902PA_Sequence_listing_ST25_ corrected" created on Oct. 29, 2019 having a size of 168,300 bytes.

TECHNICAL FIELD

The present invention relates to the production of compounds comprised in pheromones, in particular moth pheromones, such as desaturated fatty alcohols and desaturated fatty alcohol acetates and derivatives thereof, from a yeast cell.

BACKGROUND

Since the advent of DDT more than 50 years ago, broad-spectrum neurotoxic insecticides have provided the principal means for the control of economically important insects in agriculture and public health programs. Whereas the use of synthetic insecticides initially resulted in spectacular increases in crop yields and the suppression of some important human and animal disease vectors, the development of insecticide resistance in insect pest populations and the environmental damage caused by insecticides have become widely recognized as serious drawbacks to their use. Among the most significant environmental problems associated with the manufacture and use of insecticides are 1) their direct toxicity to non-target organisms (including humans); 2) their persistence in the biosphere where they can accumulate and cause untoward developmental and reproductive effects in higher organisms; 3) significant point-source pollution associated with their manufacture and distribution; 4) their worldwide dispersal.

Pheromones can be used as pest control instead of insecticides. (Z)19-14:OAc for example has been found to disrupt mating efficiency of fall armyworm with 86% efficiency when applied alone, i.e. without other pheromone components (Mitchell & McLaughlin, 1982). The commercial use of pheromones to control insect pests by mating disruption has several advantages over conventional insecticides. Pheromones are: 1) non-toxic and environmentally benign; 2) specific to one target species and do not adversely affect non-target beneficial insects, making them extremely well suited for use in integrated pest management programs; and 3) much less likely (and have never been shown) to produce resistance in the target insect. In contrast to pheromone synthesis in nature, current approaches for the commercial production of pheromones employ traditional synthetic chemical routes. Because pheromones require very high purity to elicit an insect's response, these synthesis methods are expensive and difficult, and generate large amounts of organic wastes that require treatment.

Thus the major hurdle standing in the way of using sex pheromones remains the production cost. As a result, a very small part of global agricultural land employs pheromones (estimated to less than 0.05%). Pheromone production from a cell factory is expected to significantly lower the production costs of pheromones.

SUMMARY OF INVENTION

The invention is as defined in the claims.

Herein is provided a yeast cell capable of producing a desaturated fatty alcohol and optionally a desaturated fatty alcohol acetate, said yeast cell expressing:
i) at least one heterologous desaturase capable of introducing at least one double bond in a fatty acyl-CoA having a carbon chain length of 14; and
ii) at least one heterologous fatty acyl-CoA reductase (FAR), capable of converting at least part of said desaturated fatty acyl-CoA to a desaturated fatty alcohol; and
iii) optionally an acetyltransferase capable of converting at least part of said desaturated fatty alcohol to a desaturated fatty alcohol acetate;
wherein the desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA.

Also provided are methods for production of a desaturated fatty acid and optionally a desaturated fatty alcohol acetate in a yeast cell, said method comprising the steps of providing a yeast cell and incubating said yeast cell in a medium, wherein the yeast cell expresses:
i) at least one heterologous desaturase capable of introducing at least one double bond in a fatty acyl-CoA having a carbon chain length of 14, thereby converting at least part of said fatty acyl-CoA to a desaturated fatty acyl-CoA; and
ii) at least one heterologous fatty acyl-CoA reductase, capable of converting at least part of said desaturated fatty acyl-CoA to a desaturated fatty alcohol, thereby producing said desaturated fatty alcohol; and
iii) optionally an acetyltransferase capable of converting at least part of said desaturated fatty alcohol to a desaturated fatty alcohol acetate, thereby producing said desaturated fatty alcohol acetate;
wherein the desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA.

Also provided herein are nucleic acid constructs for modifying a yeast cell, said constructs comprising:
i) a first polynucleotide encoding at least one heterologous desaturase capable of introducing at least one double bond in a fatty acyl-CoA having a carbon chain length of 14; and
ii) a second polynucleotide encoding at least one heterologous fatty acyl-CoA reductase (FAR), capable of converting at least part of said desaturated fatty acyl-CoA to a desaturated fatty alcohol; and
iii) optionally a third polynucleotide encoding an acetyltransferase capable of converting at least part of said desaturated fatty alcohol to a desaturated fatty alcohol acetate,
wherein optionally the first polynucleotide, the second polynucleotide and/or the third polynucleotide are under the control of a promoter.

Also provided is a kit of parts comprising:
a) the yeast cell as disclosed herein and instructions for use; and/or
b) a nucleic acid construct as disclosed herein, wherein said construct is for modifying a yeast cell, and
c) optionally the yeast cell to be modified.

Also provided is a desaturated fatty alcohol obtainable by the methods disclosed herein.

Also provided is a desaturated fatty alcohol acetate obtainable by the methods disclosed herein.

Also provided is the use of a desaturated fatty alcohol as disclosed herein.

Also provided is the use of a desaturated fatty alcohol acetate as disclosed herein.

DETAILED DESCRIPTION OF THE INVENTION

Definitions

Figure 1:
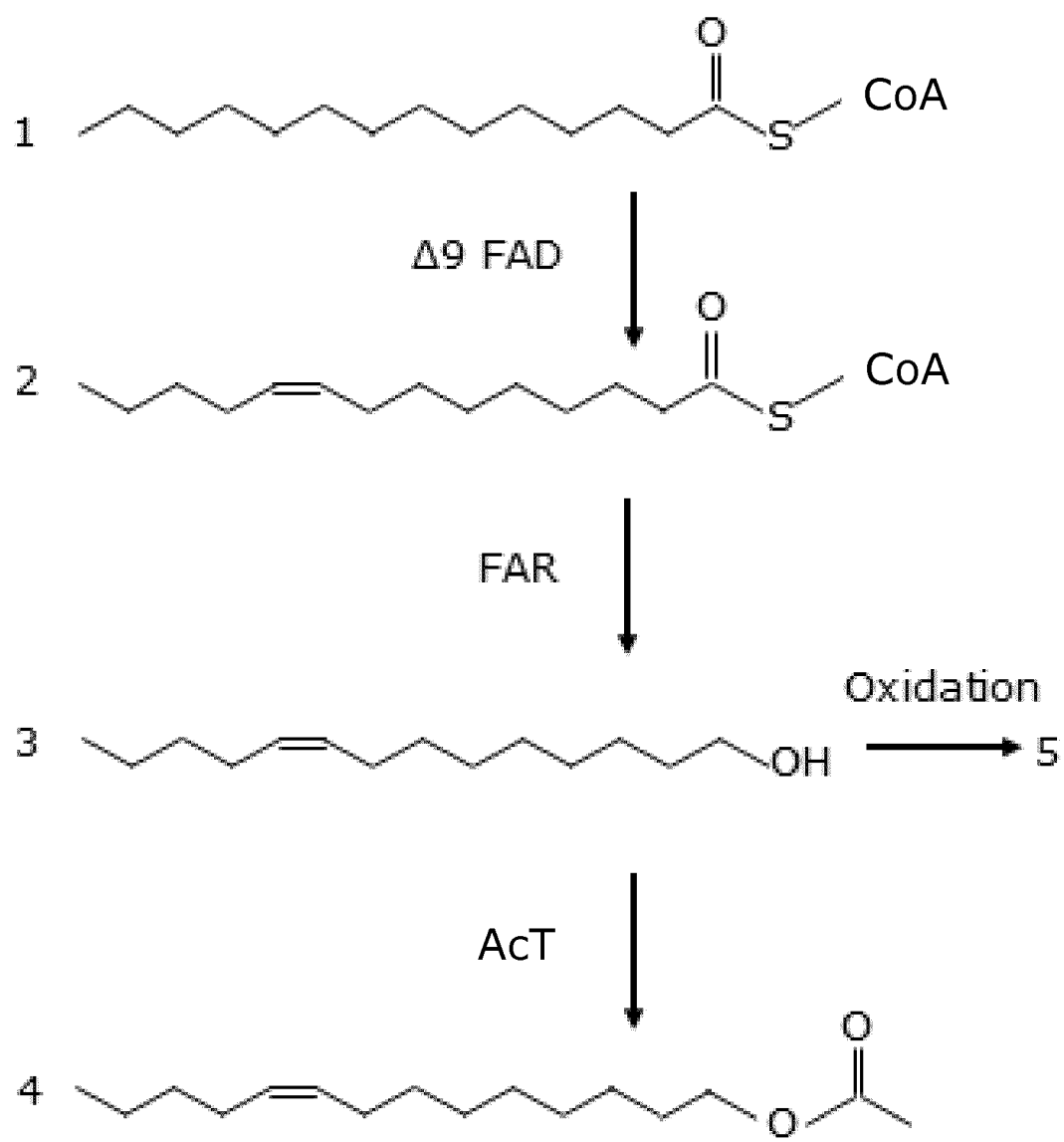
FIG. 1: pathway towards Z9-C14:OAc. (1) tetradecanoyl-CoA (myristoyl-CoA), 14:CoA (2) (Z)9-tetradecen-1-yl-CoA, Z9-14:CoA, (3) (Z)9-tetradecen-1-ol, Z9-14:OH, (4) (Z)9-tetradecen-1-yl acetate, Z9-14:OAc, (5) (Z)9-tetradecenal, Z9-14:Ald. Δ9 FAD—Z9-fatty acyl desaturase, FAR—fatty acyl-CoA reductase, AcT—acetyl-CoA transferase.

Biopesticide: the term 'biopesticide' is a contraction of 'biological pesticide' and refers to several types of pest management intervention: through predatory, parasitic, or chemical relationships. In the EU, biopesticides have been defined as "a form of pesticide based on micro-organisms or natural products". In the US, they are defined by the EPA as "including naturally occurring substances that control pests (biochemical pesticides), microorganisms that control pests (microbial pesticides), and pesticidal substances produced by plants containing added genetic material (plant-incorporated protectants) or PIPs". The present disclosure relates more particularly to biopesticides comprising natural products or naturally occurring substances. They are typically created by growing and concentrating naturally occurring organisms and/or their metabolites including bacteria and other microbes, fungi, nematodes, proteins, etc. They are often considered to be important components of integrated pest management (IPM) programmes, and have received much practical attention as substitutes to synthetic chemical plant protection products (PPPs). The Manual of Biocontrol Agents (2009: formerly the Biopesticide Manual) gives a review of the available biological insecticide (and other biology-based control) products.

Desaturated: the term "desaturated" will be herein used interchangeably with the term "unsaturated" and refers to a compound containing one or more double or triple carbon-carbon bonds.

Derived from: the term when referring to a polypeptide or a polynucleotide derived from an organism means that said polypeptide or polynucleotide is native to said organism.

Fatty acid: the term "fatty acid" refers to a carboxylic acid having a long aliphatic chain, i.e. an aliphatic chain between 4 and 28 carbon atoms, such as 4, 5, 6, 7, 8, 9, 10, 11, 12, 13, 14, 15, 16, 17, 18, 19, 20, 21, 22, 23, 24, 25, 26, 27 or 28 carbon atoms. Most naturally occurring fatty acids are unbranched. They can be saturated, or desaturated.

Fatty alcohol acetate: the term will herein be used interchangeably with "fatty acetate" and refers to an acetate having a fatty carbon chain, i.e. an aliphatic chain between 4 and 28 carbon atoms, such as 4, 5, 6, 7, 8, 9, 10, 11, 12, 13, 14, 15, 16, 17, 18, 19, 20, 21, 22, 23, 24, 25, 26, 27 or 28 carbon atoms. Fatty alcohol acetates can be saturated or desaturated.

Fatty acyl-CoA: the term will herein be used interchangeably with "fatty acyl-CoA ester", and refers to compounds of general formula R—CO—SCoA, where R is a fatty carbon chain having a carbon chain length of 4 to 28 carbon atoms, such as 4, 5, 6, 7, 8, 9, 10, 11, 12, 13, 14, 15, 16, 17, 18, 19, 20, 21, 22, 23, 24, 25, 26, 27 or 28 carbon atoms. The fatty carbon chain is joined to the —SH group of coenzyme A by a thioester bond. Fatty acyl-CoAs can be saturated or desaturated, depending on whether the fatty acid which it is derived from is saturated or desaturated.

Fatty alcohol: the term "fatty alcohol" refers herein to an alcohol derived from a fatty acyl-CoA, having a carbon chain length of 4 to 28 carbon atoms, such as 4, 5, 6, 7, 8, 9, 10, 11, 12, 13, 14, 15, 16, 17, 18, 19, 20, 21, 22, 23, 24, 25, 26, 27 or 28 carbon atoms. Fatty alcohols can be saturated or desaturated.

Fatty aldehyde: the term refers herein to an aldehyde derived from a fatty acyl-CoA, having a carbon chain length of 4 to 28 carbon atoms, such as 4, 5, 6, 7, 8, 9, 10, 11, 12, 13, 14, 15, 16, 17, 18, 19, 20, 21, 22, 23, 24, 25, 26, 27 or 28 carbon atoms. Fatty aldehydes can be saturated or desaturated.

Heterologous: the term "heterologous" when referring to a polypeptide, such as a protein or an enzyme, or to a polynucleotide, shall herein be construed to refer to a polypeptide or a polynucleotide which is not naturally present in a wild type cell. For example, the term "heterologous Δ9 desaturase" when applied to *Saccharomyces cerevisiae* refers to a Δ9 desaturase which is not naturally present in a wild type *S. cerevisiae* cell, e.g. a Δ9 desaturase derived from *Drosophila melanogaster*.

Native: the term "native" when referring to a polypeptide, such as a protein or an enzyme, or to a polynucleotide, shall herein be construed to refer to a polypeptide or a polynucleotide which is naturally present in a wild type cell.

Pest: as used herein, the term 'pest' shall refer to an organism, in particular an animal, detrimental to humans or human concerns, in particular in the context of agriculture or livestock production. A pest is any living organism which is invasive or prolific, detrimental, troublesome, noxious, destructive, a nuisance to either plants or animals, human or human concerns, livestock, human structures, wild ecosystems etc. The term often overlaps with the related terms vermin, weed, plant and animal parasites and pathogens. It is possible for an organism to be a pest in one setting but beneficial, domesticated or acceptable in another.

Pheromone: pheromones are naturally occurring compounds. Lepidopteran pheromones are designated by an unbranched aliphatic chain (between 9 and 18 carbons, such as 9, 10, 11, 12, 13, 14, 15, 16, 17 or 18 carbon atoms) ending in an alcohol, aldehyde or acetate functional group and containing up to 3 double bonds in the aliphatic backbone. Pheromone compositions may be produced chemically or biochemically, for example as described herein. Pheromones thus comprise desaturated fatty alcohols, fatty aldehydes and/or fatty alcohol acetates, such as can be obtained by the methods and cells described herein.

Saturated: the term "saturated" refers to a compound which is devoid of double or triple carbon-carbon bonds.

Specificity: the specificity of an enzyme towards a given substrate is the preference exhibited by this enzyme to catalyse a reaction starting from said substrate. In the present disclosure, a desaturase and/or a fatty acyl-CoA reductase having a higher specificity towards tetradecanoyl-CoA (myristoyl-CoA) than towards hexadecanoyl-CoA (palmitoyl-CoA) preferably catalyse a reaction with tetradecanoyl-CoA than with hexadecanoyl-CoA as a substrate. Methods to determine the specificity of a desaturase or a fatty acyl-CoA reductase are known in the art. For example, specificity of a given desaturase can be determined by incubating cells that express said desaturase in a solution comprising methyl myristate for up to 48 hours, followed by extraction and esterification of the products with methanol. The profiles of the resulting fatty acid methyl esters can then be determined by GC-MS. Desaturases with higher specificity towards myristoyl-CoA and low specificity towards palmitoyl-CoA will result in higher concentration of (Z)9-C14:Me than (Z)9-C16:Me. For example, specificity of a given reductase can be determined by incubating cells that express said reductase in a solution comprising methyl ester of (Z)9-myristate for up to 48 hours, followed by extraction and analysis of the resulting fatty alcohols by GC-MS. Reductases with higher specificity towards (Z)9-C14:CoA and low specificity towards (Z)9-C16:CoA will result in higher concentration of (Z)9-C14:OH than (Z)9-C16:OH.

Desaturase

In the present disclosure, the terms 'fatty acyl-CoA desaturase', 'desaturase', 'fatty acyl desaturase' and 'FAD' will be used interchangeably. The term generally refers to an enzyme capable of introducing at least one double bond in E/Z confirmations in an acyl-CoA having a chain length of 8, 9, 10, 11, 12, 13, 14, 15, 16, 17, 18, 19, 20, 21 or 22 carbon atoms. The double bond may be introduced in any position. For example, a desaturase introducing a double bond in position 3 is termed Δ3 desaturase. A desaturase introducing a double bond in position 5 is termed Δ5 desaturase. A desaturase introducing a double bond in position 6 is termed Δ6 desaturase. A desaturase introducing a double bond in position 7 is termed Δ7 desaturase. A desaturase introducing a double bond in position 8 is termed Δ8 desaturase. A desaturase introducing a double bond in position 9 is termed Δ9 desaturase. A desaturase introducing a double bond in position 10 is termed Δ10 desaturase. A desaturase introducing a double bond in position 11 is termed Δ11 desaturase. A desaturase introducing a double bond in position 12 is termed Δ12 desaturase. A desaturase introducing a double bond in position 13 is termed Δ13 desaturase. A desaturase introducing a double bond in position 14 is termed Δ14 desaturase. A desaturase introducing a double bond in position 15 is termed Δ15 desaturase. A desaturase introducing a double bond in position 16 is termed Δ16 desaturase. A desaturase introducing a double bond in position 17 is termed Δ17 desaturase. A desaturase introducing a double bond in position 18 is termed Δ18 desaturase. A desaturase introducing a double bond in position 19 is termed Δ19 desaturase. A desaturase introducing a double bond in position 20 is termed Δ20 desaturase.

Desaturases Catalyse the Reaction (FIG. 1):

Fatty acyl-CoA+2 ferrocytochrome b5+O(2)+2H(+) <=>desaturated fatty acyl-CoA+

2 ferricytochrome b5+2H(2)O

For the purpose of the present disclosure, the desaturase is capable of introducing at least one double bond in a fatty acyl-CoA having a carbon chain length of 14.

The yeast cell disclosed herein expresses a desaturase having a higher specificity towards tetradecanoyl-CoA than towards hexadecanoyl-CoA and/or a acyl-CoA reductase having a higher specificity towards desaturated tetradecanoyl-CoA than towards desaturated hexadecanoyl-CoA. In other words, the desaturase is more specific for substrates having a carbon chain length of 14 than for substrates having a chain length of 16. Methods to determine the specificity of a desaturase or a fatty acyl-CoA reductase are known in the art. For example, specificity of a given desaturase can be determined by incubating cells that express said desaturase in a solution comprising methyl myristate for up to 48 hours, followed by extraction and esterification of the products with methanol. The profiles of the resulting fatty acid methyl esters can then be determined by GC-MS. Desaturases with higher specificity towards myristoyl-CoA and low specificity towards palmitoyl-CoA will result in higher concentration of (Z)9-C14:Me than (Z)9-C16:Me. For example, specificity of a given reductase can be determined by incubating cells that express said reductase in a solution comprising methyl ester of (Z)9-myristate for up to 48 hours, followed by extraction and analysis of the resulting fatty alcohols by GC-MS. Reductases with higher specificity towards (Z)9-C14:CoA and low specificity towards (Z)9-C16:CoA will result in higher concentration of (Z)9-C14:OH than (Z)9-C16:OH.

In one embodiment, the cell is capable of expressing at least one heterologous Δ5 desaturase. In another embodiment, the cell is capable of expressing at least one heterologous D6 desaturase. In another embodiment, the cell is capable of expressing at least one heterologous Δ7 desaturase. In another embodiment, the cell is capable of expressing at least one heterologous Δ8 desaturase. In another embodiment, the cell is capable of expressing at least one heterologous Δ9 desaturase. In another embodiment, the cell is capable of expressing at least one heterologous Δ10 desaturase. In another embodiment, the cell is capable of expressing at least one heterologous Δ11 desaturase. In another embodiment, the cell is capable of expressing at least one heterologous Δ12 desaturase. In another embodiment, the cell is capable of expressing at least one heterologous Δ13 desaturase. The gene encoding the heterologous desaturase may be codon-optimised for the yeast cell, as is known in the art.

The skilled person will know, depending on which desaturated fatty alcohol is desired, which kind of desaturase to use. For example, for the production of a fatty alcohol desaturated in position 11, a Δ11 desaturase is preferably used. If a fatty alcohol desaturated in position 9 is desired, a Δ9 desaturase may be used, such as a Δ9 desaturase having at least 60% homology to the Δ9 desaturase from *Drosophila melanogaster* as set forth in SEQ ID NO: 10 or a Δ9 desaturase having at least 60% homology to the Δ9 desaturase from *Spodoptera litura* as set forth in SEQ ID NO: 12.

In one embodiment, the at least one heterologous desaturase is a Δ9 desaturase having at least 60% homology to the Δ9 desaturase from *Drosophila melanogaster* as set forth in SEQ ID NO: 10, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the Δ9 desaturase from *Drosophila melanogaster* as set forth in SEQ ID NO: 10.

In another embodiment, the at least one heterologous desaturase is a Δ9 desaturase having at least 60% homology to the Δ9 desaturase from *Spodoptera litura* as set forth in SEQ ID NO: 12, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the Δ9 desaturase from *Spodoptera litura* as set forth in SEQ ID NO: 12.

In one embodiment, the heterologous desaturase is derived from *Pelargonium hortorum*. In another embodiment, the heterologous desaturase is derived from *Chauliognathus lugubris*. In some embodiments, the heterologous desaturase is derived from *Drosophila melanogaster*.

The heterologous desaturase may be derived from an organism belonging to the order of Lepidoptera. Thus in one embodiment, the heterologous desaturase is derived from *Spodoptera litura*. In another embodiment, the heterologous desaturase is derived from *Choristoneura rosaceana*. In another embodiment, the heterologous desaturase is derived from *Choristoneura parallela*.

A heterologous desaturase may be expressed from a nucleic acid introduced in the cell, e.g. on a vector such as a plasmid, or by genomic integration. The nucleic acid may be codon-optimised as is known in the art for the specific yeast cell used.

In one embodiment, the at least one heterologous desaturase is encoded by a nucleic acid having at least 60% homology to the nucleic acid encoding the Δ9 desaturase from *Drosophila melanogaster* as set forth in SEQ ID NO: 9, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the nucleic acid encoding the Δ9 desaturase from *Drosophila melanogaster* as set forth in SEQ ID NO: 9.

In another embodiment, the at least one heterologous desaturase is encoded by a nucleic acid having at least 60% homology to the nucleic acid encoding the Δ9 desaturase from *Drosophila melanogaster* as set forth in SEQ ID NO: 36, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the nucleic acid encoding the Δ9 desaturase from *Drosophila melanogaster* as set forth in SEQ ID NO: 36.

In another embodiment, the at least one heterologous desaturase is encoded by a nucleic acid having at least 60% homology to the nucleic acid encoding the Δ9 desaturase from *Spodoptera litura* as set forth in SEQ ID NO: 11, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the nucleic acid encoding the Δ9 desaturase from *Spodoptera litura* as set forth in SEQ ID NO: 11.

In some embodiments, the at least one heterologous desaturase is at least two heterologous desaturases, for example two heterologous desaturases. In some embodiments, the two heterologous desaturases are the Δ9 desaturase from *Drosophila melanogaster* Dmd9 and the Δ11 desaturase from *Amyelois transitella*, as set forth in SEQ ID NO: 10 and SEQ ID NO: 68, respectively.

The yeast cell to be modified may express a native desaturase, which may have a negative impact on the production of desaturated fatty alcohol and/or desaturated fatty alcohol acetate. Accordingly, if the yeast cell to be modified expresses such a native desaturase, the cell may preferably be modified so that activity of the native desaturase is reduced or absent.

To ensure lack of activity of a native desaturase, methods known in the art can be employed. The gene encoding the native desaturase may be deleted or partly deleted in order to ensure that the native desaturase is not expressed. Alternatively, the gene may be mutated so that the native desaturase is expressed but lacks activity, e.g. by mutation of the catalytical site of the enzyme. Alternatively, translation of mRNA to an active protein may be prevented by methods such as silencing RNA or siRNA. Alternatively, the yeast cell may be incubated in a medium comprising an inhibitor which inhibits activity of the native desaturase. A compound inhibiting transcription of the gene encoding the native desaturase may also be provided so that transcription is inactivated when said compound is present.

Inactivation of the native desaturase may thus be permanent or long-term, i.e. the modified yeast cell exhibits reduced or no activity of the native desaturase in a stable manner, or it may be transient, i.e. the modified yeast cell may exhibit activity of the native desaturase for periods of time, but this activity can be suppressed for other periods of time.

Alcohol-Forming Fatty Acyl-CoA Reductase (EC 1.2.1.84)

The terms 'alcohol-forming fatty acyl-CoA reductase', 'fatty acyl-CoA reductase' and 'FAR' will be used herein interchangeably. The term 'heterologous FAR' refers to a FAR which is not naturally expressed by the yeast cell.

FARs Catalyse the Two-Step Reaction (FIG. 1)

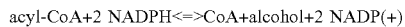

wherein in a first step, the fatty acyl-CoA is reduced to a fatty aldehyde, before the fatty aldehyde is further reduced into a fatty alcohol in a second step. The fatty acyl-CoA may be a desaturated fatty acyl-CoA.

The FARs capable of catalyzing such reaction are alcohol-forming fatty acyl-CoA reductases with an EC number 1.2.1.84.

In some embodiments, the FAR is selected from the group consisting of Har_FAR (SEQ ID NO: 25, FAR from *Helicoverpa armigera*) or a variant thereof, such as the modified Har_FAR as set forth in SEQ ID NO: 27, Has_FAR (SEQ ID NO 29, FAR from *Helicoverpa assulta*) or a variant thereof, such as the modified Has_FAR as set forth in SEQ ID NO: 31, Hs_FAR (SEQ ID: 33, FAR from *Heliothis subflexa*) or a variant thereof, such as the modified Hs_FAR as set forth in SEQ ID NO: 35, and a Ban_FAR (SEQ ID NO: 45, FAR from *Bicyclus anynana*). In specific embodiments, the FAR is Har_FAR as set forth in SEQ ID NO: 25 or a variant thereof, such as the modified Har_FAR as set forth in SEQ ID NO: 27.

In one embodiment, the FAR is Har_FAR (SEQ ID NO: 25, FAR from *Helicoverpa armigera*) or a variant thereof having at least 75% homology to Har_FAR, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Har_FAR (SEQ ID NO: 25).

In another embodiment, the FAR is a modified Har_FAR (SEQ ID NO: 27, FAR from *Helicoverpa armigera* wherein the signal peptide has been modified to HDEL) or a variant thereof having at least 75% homology thereto, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the modified Har_FAR as set forth in SEQ ID NO: 27.

In another embodiment, the FAR is Has_FAR (SEQ ID NO: 29, FAR from *Helicoverpa assulta*) or a variant thereof having at least 75% homology to Has_FAR, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Has_FAR (SEQ ID NO: 29).

In another embodiment, the FAR is a modified Has_FAR (SEQ ID NO: 31, FAR from *Helicoverpa assulta* wherein the signal peptide has been modified to HDEL) or a variant thereof having at least 75% homology thereto, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the modified Has_FAR as set forth in SEQ ID NO: 31.

In another embodiment, the FAR is Hs_FAR (SEQ ID NO: 33, FAR from *Heliothis subflexa*) or a variant thereof having at least 75% homology to Hs_FAR, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Hs_FAR (SEQ ID NO: 33).

In another embodiment, the FAR is a modified Hs_FAR (SEQ ID NO: 35, FAR from *Heliothis subflexa* wherein the signal peptide has been modified to H DEL) or a variant thereof having at least 75% homology thereto, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the modified Hs_FAR as set forth in SEQ ID NO: 35.

In another embodiment, the FAR is Ban_FAR (SEQ ID NO: 45, FAR from *Bicyclus anynana*) or a variant thereof having at least 75% homology to Hs_FAR, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Ban_FAR (SEQ ID NO: 45).

In one embodiment, the FAR is selected from a FAR having at least 60% homology to SEQ ID NO: 25, SEQ ID NO: 27, SEQ ID NO: 29, SEQ ID NO: 31, SEQ ID NO: 33, SEQ ID NO: 35 or SEQ ID NO: 45. In another embodiment, the FAR is selected from a FAR having at least 60% homology to SEQ ID NO: 25, SEQ ID NO: 27, SEQ ID NO: 29, SEQ ID NO: 31, SEQ ID NO: 33 or SEQ ID NO: 35. In another embodiment, the FAR is selected from a FAR having at least 60% homology to SEQ ID NO: 29, SEQ ID NO: 31, SEQ ID NO: 33, SEQ ID NO: 35 or SEQ ID NO: 45. In another embodiment, the FAR is selected from a FAR having at least 60% homology to SEQ ID NO: 25, SEQ ID NO: 27, SEQ ID NO: 33, SEQ ID NO: 35 or SEQ ID NO: 45. In another embodiment, the FAR is selected from a FAR having at least 60% homology to SEQ ID NO: 25, SEQ ID NO: 27, SEQ ID NO: 29, SEQ ID NO: 31 or SEQ ID NO: 45.

In some embodiments, expression of the desaturase and/or of the FAR can be induced, for example if the genes encoding these enzymes are under the control of inducible promoters, as is known in the art. The yeast cell is incubated under suitable conditions, such as in an appropriate medium and at an appropriate temperature as is known to a person of skill in the art. Suitable media supporting yeast growth are known in the art and include, but are not limited to: undefined, complete media such as YEPD (or YPD, Yeast Extract Peptone Dextrose); defined, complete medium such as SC (Synthetic Complete); defined, drop-out medium such as SD (Synthetic Dextrose) lacking one or more elements such as an amino acid or an inducer; or mineral medium, consisting of salts, vitamins and a carbon source, and others.

A heterologous fatty acyl-CoA reductase may be expressed from a nucleic acid introduced in the cell, e.g. on a vector such as a plasmid, or by genomic integration. The nucleic acid may be codon-optimised as is known in the art for the specific yeast cell used.

In some embodiments, the yeast cell may express at least two, such as two, heterologous reductases. In a specific embodiment, the yeast cell expresses the reductase from *H. armigera* and the reductase from *H. subflexa*, or variants thereof as described herein.

Acetyltransferase (EC 2.3.1.84)

The term "acetyltransferase" refers to enzymes of EC number 2.3.1.84 and can also be termed "alcohol-O-acetyltransferase" or "AcT". The enzyme acts on aliphatic alcohols, and catalyses the reaction (FIG. 1):

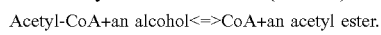
Acetyl-CoA+an alcohol<=>CoA+an acetyl ester.

The yeast cell of the present disclosure preferably overexpresses an acetyltransferase. The acetyltransferase may be a native acetyltransferase which the cell to be modified is already capable of expressing, or it may be a heterologous acetyltransferase. If the yeast cell expresses a native acetyltransferase, the yeast cell is preferably modified so that expression of the native acetyltransferase is increased. This can be done by methods known in the art, such as but not limited to introduction of additional copies of the nucleic acid encoding the acetyltransferase in the genome or on a vector, modification of the promoter to a constitutive promoter with a high expression level, or to an inducible promoter which upon induction leads to high expression levels.

If the yeast cell does not express a native acetyltransferase or if the activity of the native acetyltransferase is insufficient, resulting in low titres, a nucleic acid encoding a heterologous acetyltransferase may be introduced in the cell, either in a genomic location or on a vector, to enable expression of the acetyltransferase. Preferably, the acetyltransferase is expressed at a high level, e.g. by introducing multiple copies of the nucleic acid encoding the acetyltransferase, or by taking advantage of a constitutive promoter with a high expression level, or of an inducible promoter which upon induction leads to high expression levels. The acetyltransferase may be expressed from a nucleic acid introduced in the cell, e.g. on a vector such as a plasmid, or by genomic integration. The nucleic acid may be codon-optimised as is known in the art for the specific yeast cell used.

The term "overexpress" thus refers to the overexpression of an acetyltransferase in a yeast cell when compared to a yeast cell which has not been modified to overexpress the acetyltransferase, i.e. the parent strain.

In some embodiments, the acetyltransferase is the AcT of SEQ ID NO: 21 (Atf1, the *S. cerevisiae* AcT) or a variant thereof having at least 75% homology to Sc_Atf1, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 21.

In other embodiments, the conversion of at least part of the desaturated fatty alcohols produced by the present yeast cells to desaturated fatty alcohol acetates is done chemically, as is known to the skilled person. For example, acetyl chloride can be added to the fatty alcohol and the mixture incubated at room temperature after mixing.

Production of a Desaturated Fatty Alcohol

The yeast cells of the present disclosure can be used for the production of a desaturated fatty alcohol and optionally a desaturated fatty alcohol acetate. The yeast cell preferably expresses:
  i) at least one heterologous desaturase capable of introducing at least one double bond in a fatty acyl-CoA having a carbon chain length of 14; and
  ii) at least one heterologous fatty acyl-CoA reductase (FAR), capable of converting at least part of said desaturated fatty acyl-CoA to a desaturated fatty alcohol; and iii) optionally an acetyltransferase capable of converting at least part of said desaturated fatty alcohol to a desaturated fatty alcohol acetate;
wherein the desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA.

The yeast cell, the desaturase, the fatty acyl-CoA reductase and the acetyltransferase may all be as described above.

The yeast cell of the present disclosure may thus be used for the production of a range of desaturated fatty alcohols, such as:

(Z)—Δ5 desaturated fatty alcohols having a carbon chain length of 14;
(E)—Δ5 desaturated fatty alcohols having a carbon chain length of 14;
(Z)—Δ6 desaturated fatty alcohols having a carbon chain length of 14;
(E)—Δ6 desaturated fatty alcohols having a carbon chain length of 14;
(Z)—Δ7 desaturated fatty alcohols having a carbon chain length of 14;
(E)—Δ7 desaturated fatty alcohols having a carbon chain length of 14;
(Z)—Δ8 desaturated fatty alcohols having a carbon chain length of 14;
(E)—Δ8 desaturated fatty alcohols having a carbon chain length of 14;
(Z)—Δ9 desaturated fatty alcohols having a carbon chain length of 14;
(E)—Δ9 desaturated fatty alcohols having a carbon chain length of 14;
(Z)—Δ10 desaturated fatty alcohols having a carbon chain length of 14;
(E)—Δ10 desaturated fatty alcohols having a carbon chain length of 14;
(Z)—Δ11 desaturated fatty alcohols having a carbon chain length of 14;
(E)—Δ11 desaturated fatty alcohols having a carbon chain length of 14;
(Z)—Δ12 desaturated fatty alcohols having a carbon chain length of 14;
(E)—Δ12 desaturated fatty alcohols having a carbon chain length of 14;
(Z)—Δ13 desaturated fatty alcohols having a carbon chain length of 14; and
(E)—Δ13 desaturated fatty alcohols having a carbon chain length of 14.

The yeast cell disclosed herein may thus express a heterologous Δ9 desaturase and a fatty acyl-CoA reductase, and be used to produce (Z)9-C14:OH, i.e. a fatty alcohol having a carbon chain length of 14 harbouring a desaturation in Z conformation at position 9. This fatty alcohol is a precursor of (Z)9-C14:OAc, which is an important component of pheromones derived from various species, for example the fall armyworm *Spodoptera frugiperda*.

In other embodiments, the yeast cell expresses a heterologous Δ11 desaturase and a fatty acyl-CoA reductase, and can be used to produce (Z)11-C14:OH, i.e. a fatty alcohol having a carbon chain length of 14 harbouring a desaturation in Z conformation at position 11. This fatty alcohol is a precursor of (Z)11-C14:OAc, which is an important component of pheromones derived from various species, for example the European corn borer *Ostrinia nubilalis* and the red-banded leafroller *Argyrotaenia velutinana*.

In other embodiments, the yeast cell expresses a heterologous Δ11 desaturase and a fatty acyl-CoA reductase, and can be used to produce (E)11-C14:OH, i.e. a fatty alcohol having a carbon chain length of 14 harbouring a desaturation in E conformation at position 11. This fatty alcohol is a precursor of (E)11-C14:OAc, which is an important component of pheromones derived from various species, for example the lightbrown apple moth *Epiphyas postvittana*.

The desaturated fatty alcohols produced by the present yeast cell may be desaturated in more than one position. The desaturated fatty alcohols may be desaturated in at least two positions, such as at least three positions, such as four positions.

For example, (E)7, (Z)9 desaturated fatty alcohols may be produced having a carbon chain length of 14. (E)3, (Z)8, (Z)11 desaturated fatty alcohols may be produced having a carbon chain length of 14. (Z)9, (E)11, (E)13 desaturated fatty alcohols may be produced having a carbon chain length of 14.

The thus produced desaturated fatty alcohols may be further modified as is known in the art, for example by carbon chain shortening, in order to obtain desaturated fatty alcohols having a carbon chain of less than 14, such as 12, 10, 8, 6 or 4. Thus, (E)7, (Z)9 desaturated fatty alcohols may be produced having a carbon chain length of 12, (E)3, (Z)8, (Z)11 desaturated fatty alcohols may be produced having a carbon chain length of 12, and (Z)9, (E)11, (E)13 desaturated fatty alcohols may be produced having a carbon chain length of 12.

In order to further increase production of desaturated fatty alcohols, it may be beneficial to mutate one or more genes encoding a lipase so that the corresponding lipase has partial or total loss of activity. Accordingly, in some embodiments, the yeast cell may be as described herein and additionally carry one or more mutations resulting in total or partial loss of activity of one or more lipases.

It is known in the art that there are numerous genes encoding lipases. Their expression and/or activity may be a function of the medium in which the yeast cell is cultivated. Accordingly, the choice of medium may help choosing which lipase gene should be deleted or mutated in order for the corresponding lipase to have reduced or total loss of activity in said medium.

Several lipases may be active in one medium at the same time. Thus, in some embodiments, the yeast cell has several mutations, resulting in total or partial loss of activity of several lipases. In order to limit degradation of fatty alcohol acetate, in some embodiments the yeast cell has several mutations resulting in total or partial loss of activity of all the lipases known to be or suspected of being active in a given medium.

By way of example, lipase 2, lipase 5 and lipase 8 are the major lipases active in *Yarrowia lipolytica* when the cells are grown on glucose. Accordingly, if a glucose-based medium is employed, total or partial loss of activity of one, two or all of lipase 2, lipase 5 and lipase 8 may be considered.

In some embodiments, the lipase has at least 60% homology to lipase 2 of *Y. lipolytica* as set forth in SEQ ID NO: 72, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology. In other embodiments, the lipase has at least 60% homology to lipase 7 of *Y. lipolytica* as set forth in SEQ ID NO: 73, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology. In other embodiments, the lipase has at least 60% homology to lipase 8 of *Y. lipolytica* as set forth in SEQ ID NO: 74, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology.

In some embodiments, the yeast cell has:
a mutation resulting in total or partial loss of activity of a lipase having at least 60% homology to lipase 2 of *Y. lipolytica* as set forth in SEQ ID NO: 72; and
a mutation resulting in total or partial loss of activity of a lipase having at least 60% homology to lipase 7 of *Y. lipolytica* as set forth in SEQ ID NO: 73.

In other embodiments, the yeast cell has:
a mutation resulting in total or partial loss of activity of a lipase having at least 60% homology to lipase 2 of *Y. lipolytica* as set forth in SEQ ID NO: 72; and
a mutation resulting in total or partial loss of activity of a lipase having at least 60% homology to lipase 8 of *Y. lipolytica* as set forth in SEQ ID NO: 74.

In other embodiments, the yeast cell has:
a mutation resulting in total or partial loss of activity of a lipase having at least 60% homology to lipase 7 of *Y. lipolytica* as set forth in SEQ ID NO: 73; and
a mutation resulting in total or partial loss of activity of a lipase having at least 60% homology to lipase 8 of *Y. lipolytica* as set forth in SEQ ID NO: 74.

In some embodiments, the yeast cell has:
a mutation resulting in total or partial loss of activity of a lipase having at least 60% homology to lipase 2 of *Y. lipolytica* as set forth in SEQ ID NO: 72; and
a mutation resulting in total or partial loss of activity of a lipase having at least 60% homology to lipase 7 of *Y. lipolytica* as set forth in SEQ ID NO: 73; and
a mutation resulting in total or partial loss of activity of a lipase having at least 60% homology to lipase 8 of *Y. lipolytica* as set forth in SEQ ID NO: 74.

Production of a Desaturated Fatty Alcohol Acetate

The yeast cell of the present disclosure may optionally express or overexpress a native or a heterologous acetyltransferase capable of converting at least part of the desaturated fatty alcohols produced by the cell in desaturated fatty alcohol acetates, and may thus be used for the production of a range of desaturated fatty acetates, such as:

(Z)—$\Delta 5$ desaturated fatty acetates having a carbon chain length of 14;
(E)—$\Delta 5$ desaturated fatty acetates having a carbon chain length of 14;
(Z)—$\Delta 6$ desaturated fatty acetates having a carbon chain length of 14;
(E)—$\Delta 6$ desaturated fatty acetates having a carbon chain length of 14;
(Z)—$\Delta 7$ desaturated fatty acetates having a carbon chain length of 14;
(E)—$\Delta 7$ desaturated fatty acetates having a carbon chain length of 14;
(Z)—$\Delta 8$ desaturated fatty acetates having a carbon chain length of 14;
(E)—$\Delta 8$ desaturated fatty acetates having a carbon chain length of 14;
(Z)—$\Delta 9$ desaturated fatty acetates having a carbon chain length of 14;
(E)—$\Delta 9$ desaturated fatty acetates having a carbon chain length of 14;
(Z)—$\Delta 10$ desaturated fatty acetates having a carbon chain length of 14;
(E)—$\Delta 10$ desaturated fatty acetates having a carbon chain length of 14;
(Z)—$\Delta 11$ desaturated fatty acetates having a carbon chain length of 14;
(E)—$\Delta 11$ desaturated fatty acetates having a carbon chain length of 14;
(Z)—$\Delta 12$ desaturated fatty acetates having a carbon chain length of 14;
(E)—$\Delta 12$ desaturated fatty acetates having a carbon chain length of 14;
(Z)—$\Delta 13$ desaturated fatty acetates having a carbon chain length of 14; and
(E)—$\Delta 13$ desaturated fatty acetates having a carbon chain length of 14.

Accordingly, in one embodiment, the yeast cell expresses a heterologous $\Delta 9$ desaturase, a heterologous FAR and an acetyltransferase and can be used to obtain (Z)9-C14:OAc, i.e. a fatty alcohol acetate having a carbon chain length of 14 harbouring a desaturation in Z conformation at position 9. This fatty alcohol acetate is an important component of pheromones derived from various species, for example the fall armyworm *Spodoptera frugiperda*.

In other embodiments, the yeast cell expresses a heterologous $\Delta 11$ desaturase, a heterologous FAR and an acetyltransferase, and can be used to produce (Z)11-C14:OAc, i.e. a fatty alcohol acetate having a carbon chain length of 14 harbouring a desaturation in Z conformation at position 11. This fatty alcohol acetate is an important component of pheromones derived from various species, for example the European corn borer *Ostrinia nubilalis* and the red-banded leafroller *Argyrotaenia velutinana*.

In other embodiments, the yeast cell expresses a heterologous Δ11 desaturase, a heterologous FAR and an acetyltransferase, and can be used to produce (E)11-C14:OAc, i.e. a fatty alcohol acetate having a carbon chain length of 14 harbouring a desaturation in E conformation at position 11. This fatty alcohol acetate is an important component of pheromones derived from various species, for example the lightbrown apple moth *Epiphyas postvittana*.

The desaturated fatty acetates produced by the present yeast cell may be desaturated in more than one position. The desaturated fatty acetates may be desaturated in at least two positions, such as at least three positions, such as four positions.

For example, (E)7, (Z)9 desaturated fatty acetates may be produced having a carbon chain length of 14. (E)3, (Z)8, (Z)11 desaturated fatty acetates may be produced having a carbon chain length of 14. (Z)9, (E)11, (E)13 desaturated fatty acetates may be produced having a carbon chain length of 14.

The thus produced desaturated fatty acetates may be further modified as is known in the art, for example by carbon chain shortening, in order to obtain desaturated fatty acetates having a carbon chain of less than 14, such as 12, 10, 8, 6 or 4. Thus, (E)7, (Z)9 desaturated fatty acetates may be produced having a carbon chain length of 12, (E)3, (Z)8, (Z)11 desaturated fatty acetates may be produced having a carbon chain length of 12, and (Z)9, (E)11, (E)13 desaturated fatty acetates may be produced having a carbon chain length of 12.

Production of a Desaturated Fatty Aldehyde

While the present disclosure provides methods for producing desaturated fatty alcohols and desaturated fatty alcohol acetates, it may be of interest to further convert said fatty alcohols to the corresponding aldehydes. Thus in some embodiments, the method may further comprise the step of converting at least part of the fatty alcohols to fatty aldehydes, thereby producing fatty aldehydes. This can be achieved by chemical methods or by further engineering of the yeast cell.

In some embodiments, the step of converting at least part of the fatty alcohols to the corresponding aldehydes is a step of chemical conversion. The chemical conversion is based on the oxidation of fatty alcohols to the corresponding aldehydes. Methods for performing this conversion are known in the art. Preferred methods are environmentally friendly and minimize the amount of hazardous waste.

Thus in some embodiments, the chemical conversion may be metal free, avoiding toxic heavy metal based reagents such as manganese oxides, chromium oxides (Jones ox. PDC, PCC) or ruthenium compounds (TPAP, Ley-Griffith ox.). In some embodiments, the conversion does not involve reactions with activated dimethyl sulfoxide such as the Swern oxidation or the Pfitzner-Moffat type. Such reactions may involve the stereotypic formation of traces of intensively smelling organic sulfur compounds such as dimethyl sulfide which can be difficult to remove from the target product.

In some embodiments, the method comprises a Dess-Martin reaction (Yadav et al., 2004, Meyer et al., 1994). In some embodiments, the method comprises a Copper(I)/ABNO-catalysed aerobic alcohol oxidation reaction (Steves & Stahl, 2013).

In other embodiments, the chemical conversion comprises the oxidation with sodium hypochlorite under aqueous/organic two phase conditions (Okada et al., 2014; Tamura et al., 2012; Li et al., 2009). In some embodiments, the chemical oxidation can be performed with 1-chlorobenzotriazole in a medium of methylene chloride containing 25% pyridine (Ferrell and Yao, 1972).

Alternatively, the oxidation of a fatty alcohol to the corresponding fatty aldehyde can be performed enzymatically by alcohol dehydrogenases. The skilled person will know how to carry out enzymatic oxidation. For example, enzymatic oxidation can be carried out by contacting purified enzymes, cell extracts or whole cells, with the fatty alcohol.

The fatty alcohols obtainable by the cells and methods described herein can be further converted in fatty aldehydes by introducing a gene encoding an aldehyde-forming fatty acyl-CoA reductase EC 1.2.1.50 (FAR'). In this way, at least part of the desaturated fatty acyl-CoA can be converted to the corresponding fatty aldehyde by an aldehyde-forming fatty acyl-CoA reductase (FAR'). The enzymes capable of catalyzing this conversion can catalyse a reduction reaction, where the fatty acyl-CoA is reduced to a fatty aldehyde. Such enzymes are aldehyde-forming fatty acyl-CoA reductases, herein also referred to as FAR' or "aldehyde-forming FAR'", with an EC number 1.2.1.50. They catalyse the following reaction:

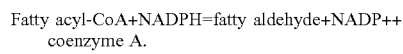

Fatty acyl-CoA+NADPH=fatty aldehyde+NADP++ coenzyme A.

In some embodiments, expression of the aldehyde-forming FAR' can be induced, for example if the gene encoding this enzyme is under the control of inducible promoters, as is known in the art. The yeast cell is incubated under suitable conditions, such as in an appropriate medium and at an appropriate temperature as is known to a person of skill in the art. Suitable media supporting yeast growth are known in the art and include, but are not limited to: undefined, complete media such as YEPD (or YPD, Yeast Extract Peptone Dextrose), defined, complete medium such as SC (Synthetic Complete), or defined, drop-out medium such as SD (Synthetic Dextrose) lacking one or more elements such as an amino acid or an inducer.

Thus, the following aldehydes can be obtained:
(Z)—Δ5 desaturated fatty aldehydes having a carbon chain length of 14;
(E)—Δ5 desaturated fatty aldehydes having a carbon chain length of 14;
(Z)—Δ6 desaturated fatty aldehydes having a carbon chain length of 14;
(E)—Δ6 desaturated fatty aldehydes having a carbon chain length of 14;
(Z)—Δ7 desaturated fatty aldehydes having a carbon chain length of 14;
(E)—Δ7 desaturated fatty aldehydes having a carbon chain length of 14;
(Z)—Δ8 desaturated fatty aldehydes having a carbon chain length of 14;
(E)—Δ8 desaturated fatty aldehydes having a carbon chain length of 14;
(Z)—Δ9 desaturated fatty aldehydes having a carbon chain length of 14;
(E)—Δ9 desaturated fatty aldehydes having a carbon chain length of 14;
(Z)—Δ10 desaturated fatty aldehydes having a carbon chain length of 14;
(E)—Δ10 desaturated fatty aldehydes having a carbon chain length of 14;

(Z)—Δ11 desaturated fatty aldehydes having a carbon chain length of 14;
(E)—Δ11 desaturated fatty aldehydes having a carbon chain length of 14;
(Z)—Δ12 desaturated fatty aldehydes having a carbon chain length of 14;
(E)—Δ12 desaturated fatty aldehydes having a carbon chain length of 14;
(Z)—Δ13 desaturated fatty aldehydes having a carbon chain length of 14; and
(E)—Δ13 desaturated fatty aldehydes having a carbon chain length of 14.

The desaturated fatty aldehydes produced by the present yeast cell may be desaturated in more than one position. The desaturated fatty aldehydes may be desaturated in at least two positions, such as at least three positions, such as four positions.

For example, (E)7, (Z)9 desaturated fatty aldehydes may be produced having a carbon chain length of 14. (E)3, (Z)8, (Z)11 desaturated fatty aldehydes may be produced having a carbon chain length of 14. (Z)9, (E)11, (E)13 desaturated fatty aldehydes may be produced having a carbon chain length of 14.

The thus produced desaturated fatty aldehydes may be further modified as is known in the art, for example by carbon chain shortening, in order to obtain desaturated fatty aldehydes having a carbon chain of less than 14, such as 12, 10, 8, 6 or 4. Thus, (E)7, (Z)9 desaturated fatty aldehydes may be produced having a carbon chain length of 12, (E)3, (Z)8, (Z)11 desaturated fatty aldehydes may be produced having a carbon chain length of 12, and (Z)9, (E)11, (E)13 desaturated fatty aldehydes may be produced having a carbon chain length of 12.

Fatty Acyl-CoA

In order for the yeast cell to produce desaturated fatty alcohols and desaturated fatty alcohol acetates as described herein, the yeast cell needs to be provided with fatty acyl-CoAs as a substrate. Preferably, the fatty acyl-CoA has a carbon chain length of 14 and is myristoyl-CoA.

Such fatty acyl-CoA can either be provided in the medium in which the yeast cell is incubated, or the yeast cell may be naturally able to produce such fatty acyl-CoA, or the yeast cell may be engineered in order to produce or to increase production of such fatty acyl-CoA. Preferably, the yeast cell is provided with or is capable of producing myristoyl-CoA.

In some embodiments, the yeast cell is not naturally capable of producing a fatty acyl-CoA having a carbon chain length of 14. The yeast cell may in this case be engineered as is known in the art, for example by the introduction of a heterologous thioesterase. Thus in some embodiments, a nucleic acid encoding a thioesterase is introduced in the yeast cell, on a vector or by genomic integration. The thioesterase gene may be under the control of an inducible promoter, or under the control of a constitutive promoter. The nucleic acid encoding a thioesterase may be codon-optimised for the yeast cell, as is known in the art. In particular, the nucleic acid may be codon-optimised for a *Yarrowia* cell, such as a *Yarrowia lipolytica* cell.

In some embodiments, the thioesterase is derived from an organism selected from *Cuphea palustris, Cuphea hookeriana, Cinnamomum camphora*, or from *Escherichia coli*. In preferred embodiments, the thioesterase is derived from *Escherichia coli* or *Cinnamomum camphora*. In some embodiments, the thioesterase has at least 60% homology to a thioesterase selected from the thioesterase derived from *Cuphea palustris* as set forth in SEQ ID NO: 23, the thioesterase derived from *Cuphea hookeriana* as set forth in SEQ ID NO: 38, the thioesterase derived from *Cinnamomum camphora* as set forth in SEQ ID NO: 40, and the thioesterase derived from *Escherichia coli* as set forth in SEQ ID NO: 42. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In another embodiment, the thioesterase has at least 60% homology to the thioesterase derived from *Cinnamomum camphora* as set forth in SEQ ID NO: 40, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the thioesterase derived from *Cinnamomum camphora* as set forth in SEQ ID NO: 40.

In another embodiment, the thioesterase has at least 60% homology to the thioesterase derived from *Escherichia coli* as set forth in SEQ ID NO: 42, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the thioesterase derived from *Escherichia coli* as set forth in SEQ ID NO: 42.

The nucleic acid encoding a thioesterase may be codon-optimised as is known in the art. In one embodiment, the yeast cell is a *Yarrowia* cell, preferably a *Yarrowia lipolytica* cell, and the nucleic acid is codon-optimised accordingly.

In one embodiment, the at least one thioesterase is encoded by a nucleic acid having at least 60% homology to the nucleic acid encoding the thioesterase derived from *Cinnamomum camphora* as set forth in SEQ ID NO: 39, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the nucleic acid encoding the thioesterase from *Cinnamomum camphora* as set forth in SEQ ID NO: 39.

In one embodiment, the at least one thioesterase is encoded by a nucleic acid having at least 60% homology to the nucleic acid encoding the thioesterase derived from *Escherichia coli* as set forth in SEQ ID NO: 41, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the nucleic acid encoding the thioesterase from *Escherichia coli* as set forth in SEQ ID NO: 41.

In some embodiments, availability of fatty acids having a chain length of 14 may be increased or further increased. For instance, the fatty acid synthase complex may be engineered so that formation of C14-fatty acyl-CoA is increased. The fatty acid synthase complex (EC 2.3.1.86) consists of two subunits, Fas1 (beta subunit) and Fas2 (alpha subunit). The alpha subunit comprises a ketoacyl synthase domain (a "binding pocket") which is hypothesized to be involved in determining the length of the synthesized fatty acids. In *Yarrowia lipolityca*, the native (wild-type) FAS2 is as set forth in SEQ ID NO: 71.

Accordingly, in order to direct the metabolic flux towards production of desaturated fatty alcohols, acetates or aldehydes having a chain length of 14 C, the yeast cell may further express a fatty acyl synthase variant having a modified ketone synthase domain. Without being bound by theory, it is hypothesized that the modified ketone synthase domain results in a modified binding pocket, which thus more readily accommodates medium length substrates such as C14 substrates, thereby producing a higher proportion of C14 products.

In one embodiment, the yeast cell is a *Yarrowia lipolytica* cell as described herein, wherein the cell further expresses a modified fatty acid synthase complex. In one embodiment, the fatty acid synthase complex is modified by mutating the gene encoding the alpha subunit of the complex. In some embodiments, the mutation is in the gene encoding FAS2. The mutation may result in modification of one or more of residue 1220 (I1220), residue 1217 (M1217) or residue 1226 (M1226) of SEQ ID NO: 71, resulting in a variant FAS2. The skilled person will know how to design such mutations.

Preferably, the mutation results in an I1220F variant, an I1220W variant, an I1220Y variant or an I1220H variant. In a specific embodiment, the mutation results in an I1220F variant. In some embodiments, the mutation results in an M1217F variant, an M1217W variant, an M1217Y variant or an M1217H variant. In other embodiments, the mutation results in an M1226F variant, an M1226W variant, an M1226Y variant or an M1226H variant. Yeast cells with more than one of the above mutations are also contemplated, such as two mutations or three mutations at residue I1220, M1217 or M1226.

Yeast Cell

The present disclosure provides a yeast cell which has been modified to produce a desaturated fatty alcohol, and optionally a desaturated fatty alcohol acetate.

Desaturated fatty alcohols and desaturated fatty alcohol acetates are components of pheromones, in particular of moth pheromones. The yeast cell disclosed herein thus provides a platform for environment-friendly moth pheromone production.

The yeast cell may be a non-naturally occurring yeast cell, for example a yeast cell which has been engineered to produce desaturated fatty alcohols and desaturated fatty alcohol acetates.

In some embodiments, the cell has been modified at the genomic level, e.g. by gene editing in the genome. The cell may also be modified by insertion of at least one nucleic acid construct such as at least one vector. The vector may be designed as is known to the skilled person to either enable integration of nucleic acid sequences in the genome, or to enable expression of a polypeptide encoded by a nucleic acid sequence comprised in the vector without genome integration.

The yeast cell may be of a genus selected from *Saccharomyces*, *Pichia*, *Yarrowia*, *Kluyveromyces*, *Candida*, *Rhodotorula*, *Rhodosporidium*, *Cryptococcus*, *Trichosporon* and *Lipomyces*. In a preferred embodiment, the genus is *Saccharomyces* or *Yarrowia*, most preferably the genus is *Yarrowia*.

The yeast cell may be of a species selected from *Saccharomyces cerevisiae*, *Pichia pastoris*, *Kluyveromyces marxianus*, *Cryptococcus albidus*, *Lipomyces lipofera*, *Lipomyces starkeyi*, *Rhodosporidium toruloides*, *Rhodotorula glutinis*, *Trichosporon pullulan* and *Yarrowia lipolytica*. In preferred embodiments, the yeast cell is a *Saccharomyces cerevisiae* cell or a *Yarrowia lipolytica* cell, most preferably the yeast cell is a *Yarrowia lipolytica* cell.

The yeast cell to be modified, which will also be referred to as the host cell, may express native enzymes which are of the same class than the enzymes which are necessary for the production of desaturated fatty alcohols and desaturated fatty alcohol acetates. In some cases, however, such native enzymes may have a negative impact on the titre of desaturated fatty alcohols and/or desaturated fatty alcohol acetates which can be obtained; the native enzymes may thus be inactivated by methods known in the art, such as gene editing. For example, the genes encoding the native enzymes having a negative impact on the titre may be deleted or mutated so as to lead to total or partial loss of activity of the native enzyme.

The yeast cell of the present disclosure express at least one heterologous desaturase capable of introducing at least one double bond in a fatty acyl-CoA having a carbon chain length of 14 as described herein, at least one heterologous fatty acyl-CoA reductase capable of converting at least part of said desaturated fatty acyl-CoA to a desaturated fatty alcohol as described herein, and optionally an acetyltransferase capable of converting at least part of said desaturated fatty alcohol to a desaturated fatty alcohol acetate, wherein the desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA. In some embodiments, the yeast also expresses an acetyltransferase. In some embodiments, the yeast also expresses a thioesterase.

In one embodiment, the yeast cell expresses:
 i) at least one heterologous D3 desaturase; and
 ii) at least one heterologous FAR; and
 iii) optionally overexpresses an acetyltransferase, and
 iv) optionally overexpresses a thioesterase,
wherein the Δ3 desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA, whereby the yeast cell produces a fatty alcohol having a carbon chain length of 14 and desaturated in position 3. The acetyltransferase may be the AcT of SEQ ID NO: 21 (Atf1, the S. cerevisiae AcT) or a variant thereof having at least 75% homology to Sc_Atf1, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 21. In some embodiments, the thioesterase has at least 60% homology to a thioesterase selected from the thioesterase derived from *Cuphea palustris* as set forth in SEQ ID NO: 23, the thioesterase from *Cuphea hookeriana* as set forth in SEQ ID NO: 38, the thioesterase from *Cinnamomum camphora* as set forth in SEQ ID NO: 40, and the thioesterase from *Escherichia coli* as set forth in SEQ ID NO: 42. Preferably, the thioesterase is derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In one embodiment, the yeast cell expresses:
 i) at least one heterologous Δ5 desaturase; and
 ii) at least one heterologous FAR; and
 iii) optionally overexpresses an acetyltransferase, and
 iv) optionally overexpresses a thioesterase,
wherein the Δ5 desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA, whereby the yeast cell produces a fatty alcohol having a carbon chain length of 14 and desaturated in position 5. The acetyltransferase may be the AcT of SEQ ID NO: 21 (Atf1, the S. cerevisiae AcT) or a variant thereof having at least 75% homology to Sc_Atf1, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 21. In some embodiments, the thioesterase has at least 60% homology to a thioesterase selected from the thioesterase derived from *Cuphea palustris* as set forth in SEQ ID NO: 23, the thioesterase from *Cuphea hookeriana* as set forth in SEQ ID NO: 38, the thioesterase from *Cinnamomum camphora* as set forth in SEQ ID NO: 40, and the thioesterase from *Escherichia coli* as set forth in SEQ ID NO: 42. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In one embodiment, the yeast cell expresses:
 i) at least one heterologous D6 desaturase; and
 ii) at least one heterologous FAR; and
 iii) optionally overexpresses an acetyltransferase, and
 iv) optionally overexpresses a thioesterase,
wherein the Δ6 desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA, whereby the yeast cell produces a fatty alcohol having a carbon chain length of 14 and desaturated in position 6. The acetyltransferase may be the AcT of SEQ ID NO: 21 (Atf1, the S. cerevisiae AcT) or a variant thereof having at least 75% homology to Sc_Atf1, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 21. In some embodiments, the thioesterase has at least 60% homology to a thioesterase selected from the thioesterase derived from *Cuphea palustris* as set forth in SEQ ID NO: 23, the thioesterase from *Cuphea hookeriana* as set forth in SEQ ID NO: 38, the thioesterase from *Cinnamomum camphora* as set forth in SEQ ID NO: 40, and the thioesterase from *Escherichia coli* as set forth in SEQ ID NO: 42. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In one embodiment, the yeast cell expresses:
 i) at least one heterologous Δ7 desaturase; and
 ii) at least one heterologous FAR; and
 iii) optionally overexpresses an acetyltransferase, and
 iv) optionally overexpresses a thioesterase, wherein the Δ7 desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA, whereby the yeast cell produces a fatty alcohol having a carbon chain length of 14 and desaturated in position 7. The acetyltransferase may be the AcT of SEQ ID NO: 21 (Atf1, the *S. cerevisiae* AcT) or a variant thereof having at least 75% homology to Sc_Atf1, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 21. In some embodiments, the thioesterase has at least 60% homology to a thioesterase selected from the thioesterase derived from *Cuphea palustris* as set forth in SEQ ID NO: 23, the thioesterase from *Cuphea hookeriana* as set forth in SEQ ID NO: 38, the thioesterase from *Cinnamomum camphora* as set forth in SEQ ID NO: 40, and the thioesterase from *Escherichia coli* as set forth in SEQ ID NO: 42. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In one embodiment, the yeast cell expresses:
  i) at least one heterologous Δ8 desaturase; and
  ii) at least one heterologous FAR; and
  iii) optionally overexpresses an acetyltransferase, and
  iv) optionally overexpresses a thioesterase,
wherein the Δ8 desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA, whereby the yeast cell produces a fatty alcohol having a carbon chain length of 14 and desaturated in position 8. The acetyltransferase may be the AcT of SEQ ID NO: 21 (Atf1, the *S. cerevisiae* AcT) or a variant thereof having at least 75% homology to Sc_Atf1, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 21. In some embodiments, the thioesterase has at least 60% homology to a thioesterase selected from the thioesterase derived from *Cuphea palustris* as set forth in SEQ ID NO: 23, the thioesterase from *Cuphea hookeriana* as set forth in SEQ ID NO: 38, the thioesterase from *Cinnamomum camphora* as set forth in SEQ ID NO: 40, and the thioesterase from *Escherichia coli* as set forth in SEQ ID NO: 42. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In one embodiment, the yeast cell expresses:
  i) at least one heterologous Δ9 desaturase; and
  ii) at least one heterologous FAR; and
  iii) optionally overexpresses an acetyltransferase, and
  iv) optionally overexpresses a thioesterase,
wherein the Δ9 desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA, whereby the yeast cell produces a fatty alcohol having a carbon chain length of 14 and desaturated in position 9. The acetyltransferase may be the AcT of SEQ ID NO: 21 (Atf1, the *S. cerevisiae* AcT) or a variant thereof having at least 75% homology to Sc_Atf1, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 21. In some embodiments, the thioesterase has at least 60% homology to a thioesterase selected from the thioesterase derived from *Cuphea palustris* as set forth in SEQ ID NO: 23, the thioesterase from *Cuphea hookeriana* as set forth in SEQ ID NO: 38, the thioesterase from *Cinnamomum camphora* as set forth in SEQ ID NO: 40, and the thioesterase from *Escherichia coli* as set forth in SEQ ID NO: 42. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In a particular embodiment, the yeast cell expresses:
  a Δ9 desaturase having at least 60% homology to the Δ9 desaturase from *Drosophila melanogaster* as set forth in SEQ ID NO: 10, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the Δ9 desaturase from *Drosophila melanogaster* as set forth in SEQ ID NO: 10; and a FAR having at least 75% homology to Har_FAR as set forth in SEQ ID NO: 25 or SEQ ID NO: 27, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Har_FAR as set forth in SEQ ID NO: 25 or SEQ ID NO: 27;

and optionally expresses or overexpresses an acetyltransferase and/or a thioesterase. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In another particular embodiment, the yeast cell expresses:

a Δ9 desaturase having at least 60% homology to the Δ9 desaturase from *Drosophila melanogaster* as set forth in SEQ ID NO: 10, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the Δ9 desaturase from *Drosophila melanogaster* as set forth in SEQ ID NO: 10; and a FAR having at least 75% homology to Has_FAR as set forth in SEQ ID NO: 29 or SEQ ID NO: 31, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Has_FAR as set forth in SEQ ID NO: 29 or SEQ ID NO: 31;

and optionally expresses or overexpresses an acetyltransferase and/or a thioesterase. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In another particular embodiment, the yeast cell expresses:

a Δ9 desaturase having at least 60% homology to the Δ9 desaturase from *Drosophila melanogaster* as set forth in SEQ ID NO: 10, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the Δ9 desaturase from *Drosophila melanogaster* as set forth in SEQ ID NO: 10; and a FAR having at least 75% homology to Hs_FAR as set forth in SEQ ID NO: 33 or SEQ ID NO: 35, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Hs_FAR as set forth in SEQ ID NO: 33 or SEQ ID NO: 35;

and optionally expresses or overexpresses an acetyltransferase and/or a thioesterase. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In another particular embodiment, the yeast cell expresses:

a Δ9 desaturase having at least 60% homology to the Δ9 desaturase from *Drosophila melanogaster* as set forth in SEQ ID NO: 10, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the Δ9 desaturase from *Drosophila melanogaster* as set forth in SEQ ID NO: 10; and a FAR having at least 75% homology to Ban_FAR as set forth in SEQ ID NO: 45, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Ban_FAR as set forth in SEQ ID NO: 45;

and optionally expresses or overexpresses an acetyltransferase and/or a thioesterase. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In a particular embodiment, the yeast cell expresses:

a Δ9 desaturase having at least 60% homology to the Δ9 desaturase from *Spodoptera litura* as set forth in SEQ ID NO: 12, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the Δ9 desaturase from *Spodoptera litura* as set forth in SEQ ID NO: 12; and a FAR having at least 75% homology to Har_FAR as set forth in SEQ ID NO: 25 or SEQ ID NO: 27, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Har_FAR as set forth in SEQ ID NO: 25 or SEQ ID NO: 27;

and optionally expresses or overexpresses an acetyltransferase and/or a thioesterase. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In another particular embodiment, the yeast cell expresses:

a Δ9 desaturase having at least 60% homology to the Δ9 desaturase from *Spodoptera litura* as set forth in SEQ ID NO: 12, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Δ9 desaturase from *Spodoptera litura* as set forth in SEQ ID NO: 12; and a FAR having at least 75% homology to Has_FAR as set forth in SEQ ID NO: 29 or SEQ ID NO: 31, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Has_FAR as set forth in SEQ ID NO: 29 or SEQ ID NO: 31;

and optionally expresses or overexpresses an acetyltransferase and/or a thioesterase. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In another particular embodiment, the yeast cell expresses:
a Δ9 desaturase having at least 60% homology to the Δ9 desaturase from *Spodoptera litura* as set forth in SEQ ID NO: 12, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the Δ9 desaturase from *Spodoptera litura* as set forth in SEQ ID NO: 12; and
a FAR having at least 75% homology to Hs_FAR as set forth in SEQ ID NO: 33 or SEQ ID NO: 35, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Hs_FAR as set forth in SEQ ID NO: 33 or SEQ ID NO: 35;
and optionally expresses or overexpresses an acetyltransferase and/or a thioesterase. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In another particular embodiment, the yeast cell expresses:
a Δ9 desaturase having at least 60% homology to the Δ9 desaturase from *Spodoptera litura* as set forth in SEQ ID NO: 12, such as at least 61% homology, such as at least 62% homology, such as at least 63% homology, such as at least 64% homology, such as at least 65% homology, such as at least 66% homology, such as at least 67% homology, such as at least 68% homology, such as at least 69% homology, such as at least 70% homology, such as at least 71% homology, such as at least 72%, such as at least 73%, such as at least 74%, such as at least 75%, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to the Δ9 desaturase from *Spodoptera litura* as set forth in SEQ ID NO: 12; and
a FAR having at least 75% homology to Ban_FAR as set forth in SEQ ID NO: 45, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to Ban_FAR as set forth in SEQ ID NO: 45;
and optionally expresses or overexpresses an acetyltransferase and/or a thioesterase. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In one embodiment, the yeast cell expresses:
i) at least one heterologous Δ10 desaturase; and
ii) at least one heterologous FAR; and
iii) optionally overexpresses an acetyltransferase, and
iv) optionally overexpresses a thioesterase,
wherein the Δ10 desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA, whereby the yeast cell produces a fatty alcohol having a carbon chain length of 14 and desaturated in position 10. The acetyltransferase may be the AcT of SEQ ID NO: 21 (Atf1, the *S. cerevisiae* AcT) or a variant thereof having at least 75% homology to Sc_Atf1, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 21. In some embodiments, the thioesterase has at least 60% homology to a thioesterase selected from the thioesterase derived from *Cuphea palustris* as set forth in SEQ ID NO: 23, the thioesterase from *Cuphea hookeriana* as set forth in SEQ ID NO: 38, the thioesterase from *Cinnamomum camphora* as set forth in SEQ ID NO: 40, and the thioesterase from *Escherichia coli* as set forth in SEQ ID NO: 42. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In one embodiment, the yeast cell expresses:
  i) at least one heterologous Δ11 desaturase; and
  ii) at least one heterologous FAR; and
  iii) optionally overexpresses an acetyltransferase, and
  iv) optionally overexpresses a thioesterase,
wherein the Δ11 desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA, whereby the yeast cell produces a fatty alcohol having a carbon chain length of 14 and desaturated in position 11. The acetyltransferase may be the AcT of SEQ ID NO: 21 (Atf1, the *S. cerevisiae* AcT) or a variant thereof having at least 75% homology to Sc_Atf1, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 21. In some embodiments, the thioesterase has at least 60% homology to a thioesterase selected from the thioesterase derived from *Cuphea palustris* as set forth in SEQ ID NO: 23, the thioesterase from *Cuphea hookeriana* as set forth in SEQ ID NO: 38, the thioesterase from *Cinnamomum camphora* as set forth in SEQ ID NO: 40, and the thioesterase from *Escherichia coli* as set forth in SEQ ID NO: 42. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In one embodiment, the yeast cell expresses:
  i) at least one heterologous Δ12 desaturase; and
  ii) at least one heterologous FAR; and
  iii) optionally overexpresses an acetyltransferase, and
  iv) optionally overexpresses a thioesterase,
wherein the Δ12 desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA, whereby the yeast cell produces a fatty alcohol having a carbon chain length of 14 and desaturated in position 12. The acetyltransferase may be the AcT of SEQ ID NO: 21 (Atf1, the *S. cerevisiae* AcT) or a variant thereof having at least 75% homology to Sc_Atf1, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 21. In some embodiments, the thioesterase has at least 60% homology to a thioesterase selected from the thioesterase derived from *Cuphea palustris* as set forth in SEQ ID NO: 23, the thioesterase from *Cuphea hookeriana* as set forth in SEQ ID NO: 38, the thioesterase from *Cinnamomum camphora* as set forth in SEQ ID NO: 40, and the thioesterase from *Escherichia coli* as set forth in SEQ ID NO: 42. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In one embodiment, the yeast cell expresses:
  i) at least one heterologous Δ13 desaturase; and
  ii) at least one heterologous FAR; and
  iii) optionally overexpresses an acetyltransferase, and
  iv) optionally overexpresses a thioesterase,
wherein the Δ13 desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA, whereby the yeast cell produces a fatty alcohol having a carbon chain length of 14 and desaturated in position 13. The acetyltransferase may be the AcT of SEQ ID NO: 21 (Atf1, the *S. cerevisiae* AcT) or a variant thereof having at least 75% homology to Sc_Atf1, such as at least 76%, such as at least 77%, such as at least 78%, such as at least 79%, such as at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% homology to SEQ ID NO: 21. In some embodiments, the thioesterase has at least 60% homology to a thioesterase selected from the thioesterase derived from *Cuphea palustris* as set forth in SEQ ID NO: 23, the thioesterase from *Cuphea hookeriana* as set forth in SEQ ID NO: 38, the thioesterase from *Cinnamomum camphora* as set forth in SEQ ID NO: 40, and the thioesterase from *Escherichia coli* as set forth in SEQ ID NO: 42. Preferably, the thioesterase has at least 60% homology to the thioesterase derived from *Cinnamomum camphora* as set forth in SEQ ID NO: 40 or from *Escherichia coli* as set forth in SEQ ID NO: 42. In one embodiment, the thioesterase has at least 60% homology to the thioesterase derived from *Cinnamomum camphora* as set forth in SEQ ID NO: 40. In another embodiment the thioesterase has at least 60% homology to the thioesterase derived from *Escherichia coli* as set forth in SEQ ID NO: 42.

In some embodiments, the yeast cell further has one or more mutations resulting in a partial or total loss of activity of one or more lipases, as detailed herein above. In some embodiments, the yeast cell further has a mutation resulting in modification of one or more subunits of the fatty acyl synthase complex; particularly mutations resulting in modifications of the ketone synthase domain, as detailed herein above, are contemplated.

In some embodiments, the yeast cell further has one or more mutations resulting in a partial or total loss of activity of one or more lipases and a mutation in one or more modification of one or more subunits of the fatty acyl synthase complex, particularly mutations resulting in modifications of the ketone synthase domain, as described herein above.

Nucleic Acids

It will be understood that throughout the present disclosure, the term 'nucleic acid encoding an activity' shall refer to a nucleic acid molecule capable of encoding a peptide, a protein or a fragment thereof having said activity. Such nucleic acid molecules may be open reading frames or genes or fragments thereof. The nucleic acid construct may also be a group of nucleic acid molecules, which together may encode several peptides, proteins or fragments thereof having an activity of interest. The term 'activity' or 'activity of interest' refers to one of the following activities: a desaturase as described herein, a fatty acyl-CoA reductase, an aldehyde-forming fatty acyl coA reductase, a thioesterase and/or an acetyltransferase activity. The nature of the one or more activity of interest will depend on the nature of the desired product one wishes to obtain with the present methods.

In some embodiments of the present methods, each of the nucleic acids encoding each of the present activities, i.e. a desaturase as described herein, a fatty acyl-CoA reductase, an aldehyde-forming fatty acyl-CoA reductase, a thioesterase and/or an acetyltransferase, may be comprised within the genome of the yeast cell or within a vector comprised within yeast cell.

In some embodiments, each of the nucleic acids encoding each of the present activities may be present in the genome of said yeast cell, either because the nucleic acid encodes a native protein, or because it has been integrated therein by genome engineering or genome editing or by crossing yeast cells of different mating types. Methods for integrating a nucleic acid are well known in the art. Thus in some embodiments the activity of interest is encoded by introduction of a heterologous nucleic acid in the yeast cell. The heterologous nucleic acid encoding said activity may be codon-optimised, or may comprise features that can help improve the activity. For example, the heterologous nucleic acid may be modified so as to encode a modified protein. Such modifications include, but are not limited to, the introduction of localisation signals, gain-of-function or loss-of-function mutations, fusion of the protein to a marker or a tag such as fluorescent tag, insertion of an inducible promoter, introduction of modifications conferring increased stability and/or half-life.

The introduction of the heterologous nucleic acid encoding the activity of interest can be performed by methods known in the art. The skilled person will recognise that such methods include, but are not limited to: cloning and homologous recombination-based methods. Cloning methods may involve the design and construction of a plasmid in an organism such as *Escherichia coli*. The plasmid may be an integrative or a non-integrative vector. Cloning-free methods comprise homologous recombination-based methods such as adaptamer-mediated PCR or gap repair. Such methods often result in integration of the heterologous nucleic acid in the genome of the yeast cell.

The nucleic acids encoding the activities of interest may be present in high copy number.

Methods for Production of Desaturated Fatty Alcohols and/or Desaturated Fatty Alcohol Acetates Provided herein is a method for production of a desaturated fatty acid and optionally a desaturated fatty alcohol acetate in a yeast cell, said method comprising the steps of providing a yeast cell and incubating said yeast cell in a medium, wherein the yeast cell expresses:

i) at least one heterologous desaturase capable of introducing at least one double bond in a fatty acyl-CoA having a carbon chain length of 14, thereby converting at least part of said fatty acyl-CoA to a desaturated fatty acyl-CoA; and ii) at least one heterologous fatty acyl-CoA reductase, capable of converting at least part of said desaturated fatty acyl-CoA to a desaturated fatty alcohol, thereby producing said desaturated fatty alcohol; and iii) optionally an acetyltransferase capable of converting at least part of said desaturated fatty alcohol to a desaturated fatty alcohol acetate, thereby producing said desaturated fatty alcohol acetate;

wherein the desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA.

The yeast cell may be able to synthesise tetradecanoyl-CoA naturally or may be engineered to synthesise tetradecanoyl-CoA or tetradecanoyl-CoA may be provided in the medium in which the cell is incubated, as described in the section "fatty acyl-CoA". The at least one heterologous desaturase and at least one heterologous fatty acyl-CoA reductase may be as described herein elsewhere. The yeast cell may be as described above.

The yeast cells described herein can be used in a method for producing a desaturated fatty alcohol and/or a desaturated fatty alcohol acetate having a chain length of 14 with unprecedented titres.

In particular, in some embodiments, the ratio of desaturated tetradecanoyl-CoA to desaturated hexadecanoyl-CoA is of at least 0.1, such as at least 0.2, such as at least 0.3, such as at least 0.4, such as at least 0.5, such as at least 0.75, such as at least 1, such as at least 2, such as at least 3, such as at least 4, such as at least 5, such as at least 6, such as at least 7, such as at least 8, such as at least 9, such as at least 10, such as at least 12.5, such as at least 15, or more.

In some embodiments, the method yields a titre of desaturated fatty alcohols of at least 1 mg/L, such as at least 1.5 mg/L, such as at least 5 mg/L, such as at least 10 mg/L, such as at least 25 mg/L, such as at least 50 mg/L, such as at least 100 mg/L, such as at least 250 mg/L, such as at least 500 mg/L, such as at least 750 mg/L, such as at least 1 g/L, such as at least 2 g/L, such as at least 3 g/L, such as at least 4 g/L, such as at least 5 g/L, or more.

In some embodiments, the method yields a titre of desaturated fatty alcohol having a chain length of 14 of at least 1 mg/L, such as at least 1.5 mg/L, such as at least 5 mg/L, such as at least 10 mg/L, such as at least 25 mg/L, such as at least 50 mg/L, such as at least 100 mg/L, such as at least 250 mg/L, such as at least 500 mg/L, such as at least 750 mg/L, such as at least 1 g/L, such as at least 2 g/L, such as at least 3 g/L, such as at least 4 g/L, such as at least 5 g/L, or more.

In some embodiments, the method yields desaturated fatty alcohols comprising at least 1% of a desaturated fatty alcohol having a chain length of 14, such as at least 1.5%, such as at least 2%, such as at least 2.5%, such as at least 3%, such as at least 3.5%, such as at least 4%, such as at least 4.5%, such as at least 5%, such as at least 7.5%, such as at least 10%, or more.

In some embodiments, the method yields a titre of desaturated fatty acetates of at least 1 mg/L, such as at least 1.5 mg/L, such as at least 5 mg/L, such as at least 10 mg/L, such as at least 25 mg/L, such as at least 50 mg/L, such as at least 100 mg/L, such as at least 250 mg/L, such as at least 500 mg/L, such as at least 750 mg/L, such as at least 1 g/L, such as at least 2 g/L, such as at least 3 g/L, such as at least 4 g/L, such as at least 5 g/L, or more.

In some embodiments, the method yields a titre of desaturated fatty acetate having a chain length of 14 of at least 1 mg/L, such as at least 1.5 mg/L, such as at least 5 mg/L, such as at least 10 mg/L, such as at least 25 mg/L, such as at least 50 mg/L, such as at least 100 mg/L, such as at least 250 mg/L, such as at least 500 mg/L, such as at least 750 mg/L, such as at least 1 g/L, such as at least 2 g/L, such as at least 3 g/L, such as at least 4 g/L, such as at least 5 g/L, or more.

In some embodiments, the method yields desaturated fatty acetates comprising at least 1% of a desaturated fatty acetate having a chain length of 14, such as at least 1.5%, such as at least 2%, such as at least 2.5%, such as at least 3%, such as at least 3.5%, such as at least 4%, such as at least 4.5%, such as at least 5%, such as at least 7.5%, such as at least 10%.

In some embodiments, the yeast cell may further express an aldehyde-forming fatty acyl-CoA reductase EC 1.2.1.50 (FAR') as described herein above.

Recovery

It may be desirable to recover the products obtained by the methods disclosed herein. Thus the present methods may comprise a further step of recovering the desaturated fatty alcohol and/or the desaturated fatty alcohol acetate produced by the present yeast cell.

In some embodiments, the method comprises a step of recovering the desaturated fatty alcohols. In a particular embodiment, the method comprises a step of recovering the desaturated fatty alcohols having a carbon chain length of 14. In other embodiments, the method comprises a step of recovering the fatty alcohol acetates. In a particular embodiment, the method comprises a step of recovering the fatty alcohol acetates having a carbon chain length of 14.

Methods for recovering the products obtained by the present invention are known in the art and may comprise an extraction with a hydrophobic solvent such as decane, hexane or a vegetable oil.

The recovered products may be modified further, for example desaturated fatty alcohols may be converted to the corresponding desaturated fatty aldehydes as described herein above.

The recovered products, i.e. the desaturated fatty alcohols and/or desaturated fatty alcohol acetates, may also be formulated into a pheromone composition. The composition may further comprise one or more additional compounds such as a liquid or solid carrier or substrate. Fatty aldehydes obtained from said desaturated fatty alcohols may also be comprised in such compositions.

Kit

Provided herein is a kit of parts for performing the present methods. The kit of parts may comprise a yeast cell "ready to use" as described herein. In one embodiment, the yeast cell is a *Yarrowia* cell, such as a *Yarrowia lipolytica* cell.

In another embodiment, the kit of parts comprises a nucleic acid construct encoding the activities of interest to be introduced in the yeast cell. The nucleic acid construct may be provided as a plurality of nucleic acid constructs, such as a plurality of vectors, wherein each vector encodes one or several of the desired activities.

The kit of parts may optionally comprise the yeast cell to be modified.

In some embodiments, the kit of parts comprises all of the above.

Pheromone Composition

The present disclosure thus provides compounds, in particular fatty alcohols and fatty alcohol acetates, as well as derivatives thereof, and their use. In particular, the compounds obtainable using the present cells and methods are useful as components of pheromone compositions. Such pheromone compositions may be useful for integrated pest management. They can be used as is known in the art for e.g. mating disruption.

The desaturated fatty alcohols and desaturated fatty alcohol acetates obtainable by the present methods or using the present yeast cells may be formulated in a pheromone composition.

Such pheromone compositions may be used as integrated pest management products, which can be used in a method of monitoring the presence of pest or in a method of disrupting the mating of pest.

Pheromone compositions as disclosed herein may be used as biopesticides. Such compositions can be sprayed or dispensed on a culture, in a field or in an orchard. They can also, as is known in the art, be soaked e.g. onto a rubber septa, or mixed with other components. This can result in mating disruption, thereby preventing pest reproduction, or it can be used in combination with a trapping device to entrap the pests. Non-limiting examples of pests against which the present pheromone compositions can be used are: cotton bollworm (*Helicoverpa armigera*), striped stemborer (*Chilo suppressalis*), diamond back moth (*Plutella xylostella*), cabbage moth (*Mamestra brassicae*), large cabbage-heart caterpillar (*Crocidolomia binotalis*), European corn stalk borer (*Sesamia nonagrioides*), currant clearwing (*Synanthedon tipuliformis*) and artichoke plume moth (*Platyptilia carduidactylal*). Accordingly, use of the present compositions on a culture can lead to increased crop yield, with substantially no environmental impact.

The relative amounts of fatty alcohols and fatty alcohol acetates in the present pheromone compositions may vary depending on the nature of the crop and/or of the pest to be controlled; geographical variations may also exist. Determining the optimal relative amounts may thus require routine optimisation. The pheromone compositions may also comprise fatty aldehydes.

Examples of compositions used as repellents can be found in Kehat & Dunkelblum, 1993, for *H. armigera*, in Alfaro et al., 2009, for *C. suppressalis*, in Eizaguirre et al., 2002, for *S. nonagrioides*; in Wu et al., 2012, for *P. xylostella*; in Bari et al., 2003, for *P. carduidactyla*

In some embodiments, the pheromone composition may further comprise one or more additional compounds such as a liquid or solid carrier or substrate. For example, suitable carriers or substrate include vegetable oils, refined mineral oils or fractions thereof, rubbers, plastics, silica, diatomaceous earth, wax matrix and cellulose powder.

The pheromone composition may be formulated as is known in the art. For example, it may be in the form of a solution, a gel, a powder. The pheromone composition may be formulated so that it can be easily dispensed, as is known in the art.

EXAMPLES

Example 1: Construction of Plasmids and Strains

Genes encoding desaturases from *Pelargonium hortorum* (SEQ ID NO: 1) and *Ricinus communis* (SEQ ID NO: 3) were synthesized by GeneArt (Life Technologies) in codon-optimized versions for *Y. lipolytica*. The genes encoding desaturases from *Amyelois transitella* (SEQ ID NO: 5 and SEQ ID NO: 7), from *Drosophila melanogaster* (SEQ ID NO: 9), and OLE1 from *S. cerevisiae* were synthesized by GeneArt in codon-optimized version for *S. cerevisiae*. The synthetic genes encoding *Amyelois transitella* desaturase and *S. cerevisiae* desaturase OLE1 had attB1-attB2 sites incorporated, which allowed to clone these genes into the vector pDONR 221 via Gateway cloning system (Invitrogen: Gateway® Technology Manual. [http://tools.invitrogen.com/content/sfs/manuals/gatewayman.pdf]. The gene encoding alcohol acetyltransferase ATF1 (SEQ ID NO: 19) was amplified from genomic DNA preparation of *S. cerevisiae* strain CEN.PK102-5B. A gene encoding fatty acyl reductase from *Helicoverpa armigera* was modified so that its putative native KKSYE signal was replaced with HDEL signal from *S. cerevisiae* and this gene was also synthesized by GeneArt (Life Technologies) in codon-optimized version for *S. cerevisiae*. All the genes were amplified by PCR to obtain the fragments for cloning into yeast expression vectors. The primers are listed in Table 1 and the resulting DNA fragments are listed in Table 2. The PCR products were separated on a 1%-agarose gel containing RedSafe™ (iNtRON Biotechnology). PCR products of the correct size were excised from the gel and purified using the Nucleospin® Gel and PCR Clean-up kit (Macherey-Nagel).

TABLE 1

Primers.

| Primer name | Primer sequence, 5'->3' | SEQ ID NO: |
|---|---|---|
| PR-1852 (PTDH3_fw) | CACGCGAUATAAAAAACACGCTTTTTCAG | 46 |
| PR-1853 (PTDH3_rv) | ACCTGCACUTTTGTTTGTTTATGTGTGTTTATTC | 47 |
| PR-1565 (PTEF1) | ATGACAGAUTTGTAATTAAAACTTAG | 48 |
| PR-8332 (Har_FAR_U1_fw) | AGTGCAGGUAAAACAATGGTTGTCTTGACCTCCAAAG | 49 |
| PR-10739 (Har_FAR_HDEL_U1_rev) | cgtgcgaUttacaattcatcatgttccaagaaatgtctaacac | 50 |
| PR-14318 (Phd9_U2_fw) | ATCTGTCAUAAAACAatgggcgtcctgctgaac | 51 |
| PR-14276 (Phd9_U2_rev) | cacgcgaUttagacctttcgg | 52 |
| PR-14319 (RCd9_U2_fw) | ATCTGTCAUAAAACAatggccctgaag | 53 |
| PR-14278 (RCd9_U2_rev) | cacgcgaUttacagcttcacctg | 54 |
| PR-14320 (Atf1_U2_fw) | ATCTGTCAUAAAACAATGAATGAAATCGATGAG | 55 |
| PR-14321 (Atf1_U2_rev) | CACGCGAUCTAAGGGCCTAAAAGGAGAGCTTTG | 56 |
| PR-15974 (Dmd9_U1_fw) | AGTGCAGGUAAAACAatggctccatactctagaatc | 57 |
| PR-15975 (Dmd9_U1_rev) | CGTGCGAUttatctggacttgtcaacc | 58 |
| PR-15976 (attB1_Dmd9_F) | GGGGACAAGTTTGTACAAAAAAGCAGGCTATGGCTCCATACTCTAGAATCTAC | 59 |
| PR-15977 (attB2_Dmd9_R) | GGGGACCACTTTGTACAAGAAAGCTGGGTTTATCTGGACTTGTCAACCAACAAAACGTTTCTAG | 60 |
| PR-15978 (attB1_Phd9_F) | GGGGACAAGTTTGTACAAAAAAGCAGGCTATGGCCCTGAAGCTGAACCCCTTC | 61 |
| PR-15979 (attB2_Phd9_R) | GGGGACCACTTTGTACAAGAAAGCTGGGTTTACAGCTTCACCTGTCGGTCGAAG | 62 |
| PR-15980 (attB1_Rcd9_F) | GGGGACAAGTTTGTACAAAAAAGCAGGCTATGGGCGTCCTGCTGAACATCTG | 63 |
| PR-15981 (attB1_Rcd_R) | GGGGACCACTTTGTACAAGAAAGCTGGGTTTAGACCTTTCGGTCGAAGATCCA | 64 |

TABLE 2

DNA fragments obtained by PCR using the indicated template and primers.

| DNA fragment ID and name | Description | Fw_primer | Rv_primer | Template DNA |
|---|---|---|---|---|
| BB0410 (PTDH3) | PTDH3 promotor from S. cerevisiae | PR-1852 (PTDH3_fw) | PR-1853 (PTDH3_rv) | Genomic DNA from S. cerevisiae CEN.PK102-5B |
| BB0464 (<-PTDH3-PTEF1->) | PTDH3 and PTEF1 promotor from S. cerevisiae | PR-1565 (PTEF1) | PR-1853 (PTDH3_rv) | Genomic DNA from S. cerevisiae CEN.PK102-5B |
| BB0915 (HAR_FAR_HDEL <-) | Fatty acyl-CoA reductase from Helicoverpa armigera with modified C-terminus | PR-8332 (Har_FAR_U1_fw) | PR-10739 (Har_FAR_HDEL_U1_rev) | |
| BB1420 (Phd9) | Desaturase from Pelargonium x hortorum | PR-14318 (Phd9_U2_fw) | PR-14276 (Phd9_U2_rev) | |
| BB1421 (RCd9) | Desaturase from Ricinus communis | PR-14319 (RCd9_U2_fw) | PR-14278 (RCd9_U2_rev) | |
| BB1422 (Atf1->) | Alcohol acetyltransferase from Saccharomyces cerevisiae | PR-14320 (Atf1_U2_fw) | PR-14321 (Atf1_U2_rev) | Genomic DNA from S. cerevisiae CEN.PK102-5B |
| BB1696 (Dmd9) | Desaturase from Drosophila melanogaster | PR-15974 (Dmd9_U1_fw) | PR-15975 (Dmd9_U1_rev) | |
| BB1870 (Dmd9) | Desaturase from Drosophila melanogaster | PR-15976 (attB1_Dmd9_F) | PR-15977 (attB2_Dmd9_R) | pCfB5316 |
| BB1871 (Phd9) | Desaturase from Pelargonium x hortorum | PR-15978 (attB1_Phd9_F) | PR-15979 (attB2_Phd9_R) | pCfB4584 |
| BB1872 (Rcd9) | Desaturase from Ricinus communis | PR-15980 (attB1_Rcd9_F) | PR-15981 (attB1_Rcd9_R) | pCfB4585 |

Example 2: Cloning of Vectors pYEX-CHT-Dmd9, pYEX-CHT-Phd9, pYEX-CHT-Rcd9, pYEX-CHT-Atrd1432, pYEX-CHT-Atrd236 and pYEX-CHT-OLE1

DNA fragments BB1870, BB1871, and BB1872 were amplified from respectively plasmids pCfB5316, pCfB4584 and pCfB4585 by using the Maxima Hot Start Green PCR Master Mix (2λ) (ThermoFisher Scientific) according to the manufacturers protocol. The PCR mix contained 20 µl water, 25 µl Maxima Hot Start Green PCR Master Mix, 2.5 µl forward primer (10 µM), 2.5 µl reverse primer (10 µM) and 5 ng DNA template and the following PCR program was used: 94° C. for 2 min, 35 cycles of [94° C. for 15 sec, 55° C. for 30 sec, 72° C. for 2 min 30 sec], 72° C. for 7 min. The PCR products were separated on a 1%-agarose gel. PCR products of the correct size were excised from the gel and purified using the Nucleospin® Gel and PCR Clean-up kit (Macherey-Nagel).

The resulting DNA fragments (BB1870, BB1871 and BB1872) were cloned into the vector pDONR 221 by Gateway cloning technology creating the so called "entry clones" (ThermoFisher Scientific). The BP reaction was performed by mixing 100 ng of synthetic genes, 100 ng of pDONR 221 and 1 µL of BP clonase (Life Technologies). The reaction was incubated at room temperature for 1 hour. The reaction mix was transformed into E. coli competent HB101 cells (Life Technologies) by heat shock and the cells were plated on Lysogeny Broth (LB) agar plates with 50 mg/L kanamycin and incubated overnight at 37° C. Single colonies were inoculated into 5 ml of liquid LB with 50 mg/L kanamycin in 13-ml sterile tubes and cultivated with shaking overnight. The plasmids were purified from overnight E. coli cultures and sequenced to confirm correct cloning. The genes were shuttled from the entry clones to the destination yeast expression vector pYEX-CHT-DEST (Ding B J, Carraher C, Löfstedt C. 2016. Sequence variation determining stereochemistry of a Δ11 desaturase active in moth sex pheromone biosynthesis. Insect Biochem Mol Biol. 74: 68-75. doi: 10.1016/j.ibmb.2016.05.002.) by mixing 100 ng of the entry clones with 100 ng of destination vector pYEX-CHT-DEST and 1 µL of LR clonase (Invitrogen). The reaction was incubated at room temperature for 1 hour, followed by transformation into E. coli competent HB101 cells by heat-shock. The cells were plated on Lysogeny Broth (LB) agar plates with 100 mg/L ampicillin. The plasmids were purified from overnight E. coli cultures and the correct cloning was confirmed by sequencing.

Example 3: Cloning of Vectors pCfB5316, pCfB4584, pCfB4585, pCfB4580

The DNA biobricks BB0410, BB1696, BB0301, BB1420, BB0301, BB1421, BB0464, BB0915 and BB1422 were amplified by PCR like following. The PCR mix contained 32 µl water, 10 µl high fidelity Phusion® polymerase buffer (5×), 1 µl dNTPs (10 mM), 1 µl Phusion U polymerase, 2.5 µl forward primer (10 µM), 2.5 µl reverse primer (10 µM) and 1 µl DNA template and the following PCR program was used: 94° C. for 2 min, 30 cycles of [94° C. for 15 sec, 52° C. for 20 sec, 68° C. for 1 min 30 sec], 68° C. for 2 min, pause at 10° C.

The integrative vector EasyClone 2.0 pCfB2909 (XII-5-MarkerFree) is described in Jessop-Fabre et. al., 2016 and pCfB2190 is described in Stovicek et al., 2015. Plasmid pCfB2912 was constructed by USER fusion of DNA fragments BB0593 (contains pCfB387 vector backbone) and BB0598 (contains nourseothricin resistance cassette), as described in Stovicek et al, 2015. All integrative vectors were linearized with FastDigest® AsiSI (Fermentas) for 2 hours at 37° C. and then nicked with Nb.Bsml (New England Biolabs) for 1 hour at 65° C. The resulting vectors containing sticky ends were separated by gel electrophoresis, excised and gel-purified using the Nucleospin® Gel and PCR Clean-up kit (Macherey-Nagel). The DNA fragments were cloned into the so prepared vectors by USER-cloning via the following protocol: 1 µl of linearized plasmid, 1 µl of promoter fragment, 1.5 µl of gene fragment, 1 µl high fidelity Phusion® polymerase buffer (5×), and 0.5 µl USER enzyme (New England Biolabs) were mixed and incubated at 37° C. for 25 min and at 25° C. for 25 min. The reaction was transformed into chemically competent E. coli DHalpha cells and the cells were plated on Lysogeny Broth (LB) agar plates with 100 mg/L ampicillin. The plates were incubated overnight at 37° C. and the resulting colonies were screened by colony PCR. The plasmids were purified from overnight E. coli cultures and the correct cloning was confirmed by sequencing. The constructed vectors are listed in Table 3.

Example 4: Construction of Strains

The pYEX-CHT derived recombinant expression vectors containing the different desaturase genes were introduced into S. cerevisiae deficient for both OLE1 and ELO1 (MATa elo1::HIS3 ole1::LEU2 ade2 his3 leu2 ura3; (Schneiter et al., 2000)), using the S.c. easy yeast transformation kit (Life Technologies). For selection of uracil and leucine protothrophic clones, the transformed yeast cells were plated on medium composed of 0.7% YNB (without amino acid, with ammonium sulfate), 1.546% drop-out mix lacking uracil and leucine (Formedium™ LTD, Norwich, England), 2% glucose, 1% tergitol (type Nonidet NP-40, Sigma-Aldrich Sweden AB, Stockholm, Sweden), 0.01% adenine (Sigma), and 0.5 mM oleic acid (Sigma). The constructed yeast strains are listed in Table 4.

The integrative expression vectors pCfB4580 and pCfB5316 were linearized with FastDigest® NotI (Fermentas). pCfB4580 was transformed into S. cerevisiae CEN.PK102-5B using lithium-acetate protocol (Gietz & Schiestl, 2007) leading to strain ST4854. Positive transformants were selected on yeast synthetic drop-out plates without leucine (Sigma-Aldrich). Correct integration of the expression constructs into the genome of S. cerevisiae was confirmed by colony PCR. Strain ST5290 was constructed by integrating pCfB5316 into ST4854 using a method described in (Jessop-Fabre et al., 2016). The constructed strains are listed in Table 5.

Example 5: 49 Desaturases Activities and Specificities

The activities and specificities of desaturases were tested in a S. cerevisiae strain with deletions of OLE1 and ELO1

TABLE 3

Expression vectors.

| Expression vector name | Selection marker | Parent vector | DNA fragments cloned into parent vector |
|---|---|---|---|
| pYEX-CHT-Dmd9 | Ura, Leu | pYEX-CHT-DEST | BB1870 (Dmd9) |
| pYEX-CHT-Phd9 | Ura, Leu | pYEX-CHT-DEST | BB1871 (Phd9) |
| pYEX-CHT-Rcd9 | Ura, Leu | pYEX-CHT-DEST | BB1872 (Rcd9) |
| pYEX-CHT-Atrd1432 | Ura, Leu | pYEX-CHT-DEST | |
| pYEX-CHT-Atrd236 | Ura, Leu | pYEX-CHT-DEST | |
| pYEX-CHT-OLE1 | Ura, Leu | pYEX-CHT-DEST | |
| pCfB4584 (pXI-5-loxP-NatMXsyn->PTEF1-Phd9) | NatMXSyn | pCfB2912 | BB0301 (PTEF1->), BB1420 (Phd9->) |
| pCfB4585 (pXI-5-loxP-NatMXsyn->PTEF1-Rcd9) | NatMXSyn | pCfB2912 | BB0301 (PTEF1->), BB1421 (Rcd9->) |
| pCfB4580 (pXI-KlLeu2syn-Har_FAR_HDEL_PTDH3<--> PTef1-Atf1) | KlLEU2 | pCfB2190 | BB0464 (<-PTDH3-PTEF1->), BB0915 (HAR_FAR_HDEL<-), BB1422 (Atf1->) |
| pCfB5316 (pXII-5-Dmd9-PTDH3<-) | markerfree | pCfB2909 | BB0410 (PTDH3<-), BB1696 (Dmd9<-) | genes, encoding for 49-fatty acid desaturase and medium-chain acyl elongase respectively (Schneiter et al., 2000).

Three individual colonies of strains ST_Atr1432, ST_Atr236, ST_Phd9, ST_Rcd9, ST_ScOLE1 and ST_DmeD9 were inoculated into 1 mL selective media (SC-Ura-Leu) and incubated at 30° C. and 300 rpm for 48 h. The cultures were diluted to an OD600 of 0.4 in 5 mL selective medium supplemented with 2 mM CuSO4 and the 0.5 mM methyl myristate (14:Me) (Larodan Fine Chemicals, Sweden). The methyl myristate stock solution was prepared to a concentration of 100 mM in 96% ethanol. The yeast cultures were incubated at 30° C. at 300 rpm for 48 hours.

1 mL of culture was sampled and 3.12 µg of nonadecylic acid methyl ester was added as internal standard. Total lipids were extracted using 3.75 mL of methanol/chloroform (2:1, v/v), in a glass vial. One mL of acetic acid (0.15 M) and 1.25 mL of water were added to the tube. Tubes were vortexed vigorously and centrifuged at 2,000×g for 2 min. The bottom chloroform phase, about 1 mL, containing the total lipids, was transferred to a new glass vial and the solvent was evaporated to dryness. Fatty acid methyl esters (FAMEs) were made from this total lipid extract by acid methanolysis. One mL of 2% sulfuric acid in methanol (v/v) was added to the tube, vortexed vigorously, and incubated at 90° C. for 1 h. After incubation, 1 mL of water was added and mixed well, and then 1 mL of hexane was used to extract the FAMEs.

The methyl ester samples were subjected to GC-MS analyses on a Hewlett Packard 6890 GC coupled to a mass selective detector HP 5973. The GC was equipped with an INNOWax column (30 m×0.25 mm×0.25 µm), and helium was used as the carrier gas (average velocity: 33 cm/s). The MS was operated in electron impact mode (70 eV), and the injector was configured in splitless mode at 220° C. The oven temperature was set to 80° C. for 1 min, then increased at a rate of 10° C./min up to 210° C., followed by a hold at 210° C. for 15 min, and then increased at a rate of 10° C./min up to 230° C. followed by a hold at 230° C. for 20 min. The monounsaturated fatty-acid products were identified by comparing their retention times and mass spectra with those of synthetic standards. Data were analyzed by the ChemStation software (Agilent, Technologies, USA).

The measured concentrations of Z9-14:Me and Z9-16:Me (Table 4) show that strain ST_DmeD9, expressing desaturase from *D. melanogaster*, resulted in the highest concentration of Z9-14:Me (3.67 mg/L) and in the maximal ratio of Z9-14:Me and Z9-16:Me. This indicates that among the tested desaturases, *D. melanogaster* desaturase has the highest activity and specificity towards C14-CoA substrate.

Example 6: Production of (Z)9-tetradecen-1-yl Acetate

The strains for production of pheromone were created on the basis of *S. cerevisiae* CEN.PK102-5B, which had active OLE1 and ELO1 genes. The obtained strains are listed in table 5.

Strains ST4854 and ST5290 were inoculated into 5 ml synthetic complete medium (lacking histidine, leucine, tryptophan supplemented with 20 mg/L uracil and 76 mg/L histidine) and cultivated in 12-ml glass tubes (Duran, Wertheim, Germany) with metal labocap lids (Lüdiswiss, Flawil, Switzerland) overnight at 30° C. with shaking at 250 rpm. The following day the overnight culture was centrifuged, the supernatant was discarded and the pellet was resuspended in 2 ml of mineral medium, which had the composition as described in (Jensen et al, 2014). The medium was supplemented with 76 mg/L histidine and 20 mg/L uracil. The cultures were incubated at 30° C. with shaking at 250 rpm for 48 hours.

1 mL sample of culture was transferred into a 4-mL glass vial and 10 µL of internal standard stock (1 µg/µl (Z)10-heptan-1-yl methyl ester in 100% ethanol) was added. The vials were covered with small pieces of aluminum foil and we used a needle to pierce small holes in the foil covers. The samples were vortexed and placed at −80° C. for storage until analysis. The samples were freeze-dried (Freezone6 and Stoppening tray dryer, Labconco, Kansas City, USA) at −40° C., then 1 mL chloroform:methanol 2:1 was added to disrupt the cells. The mix was vortexed for 45 s and left at room temperature for 4 hours. The organic solvents were evaporated slowly under a nitrogen stream. 1 ml of hexane was added, the samples were vortexed for 10 s, centrifuged and 200 µl were transferred to a new glass vial. GC-MS analysis was performed as described in Example 5. The concentration of (Z)-9-tetradecen-1-yl acetate was calculated based on internal standard.

As apparent from the results, overexpression of *D. melanogaster* desaturase increased the titer of Z9:14:OAc more than 5-fold. Moreover, the product fraction of the total fatty alcohol acetates increased from 2 to 10%.

TABLE 4

Activity and specificity of heterologous desaturases in yeast.

| Strain name | Over-expressed desaturase | Parent strain (key characteristics) | Vectors introduced into parent strain | Z9-14:Me (mg/L) | Z9-16:Me (mg/L) | Ratio of 14:1/16:1 [specificity] |
|---|---|---|---|---|---|---|
| ST_Atr1432 | Atr1432 | Δole1Δelo1 | pYEX-CHT-Atrd1432 | 0.25 | 0.56 | 0.45 |
| ST_Atr236 | Atr236 | Δole1Δelo1 | pYEX-CHT-Atr236 | 0.03 | 0.13 | 0.20 |
| ST_Phd9 | Phd9 | Δole1Δelo1 | pYEX-CHT-Phd9 | 0.00 | 0.00 | 0.00 |
| ST_Rcd9 | Rcd9 | Δole1Δelo1 | pYEX-CHT-Rcd9 | 0.00 | 0.00 | 0.00 |
| ST_ScOLE1 | ScOLE1 | Δole1Δelo1 | pYEX-CHT-OLE1 | 0.39 | 3.01 | 0.13 |
| ST_DmeD9 | DmeΔ9 | Δole1Δelo1 | pYEX-CHT-Dmd9 | 3.67 | 0.24 | 15.29 |

TABLE 5

Production of (Z)-9-tetradecen-1-yl acetate by yeast

| Strain | Overexpressed genes | Parent strain | Vectors introduced into parent strain | Z9-14:OAc (mg/L) | % of Z9-14:OAc in relation to total fatty acyl acetates |
|---|---|---|---|---|---|
| ST4854 | ATF1 from S. cerevisiae, Har_FAR from Helicoverpa armigera | S. cerevisiae CEN.PK102-5B | pCfB4580 (pXI-KlLeu2syn-Har_FAR_HDEL_PTDH3 <-->PTef1-Atf1) | 1.4 ± 0.4 | 1.9 ± 0.1% |
| ST5290 | ATF1 from S. cerevisiae, Har_FAR from Helicoverpa armigera, DmeΔ9 from D. melanogaster | S. cerevisiae CEN.PK102-5B | pCfB4580 (pXI-KlLeu2syn-Har_FAR_HDEL_PTDH3 <-->PTef1-Atf1), pCfB5316 (pXII-5-Dmd9-PTDH3<-) | 7.3 ± 0.2 | 9.8 ± 0.4% |

Example 7: Method to Produce Z11-C14:OAc

A gene, encoding a Δ11 desaturase that preferentially produces Z11-C14:CoA is overexpressed in a yeast strain along with HarFAR and Atf1. The resulting strain is grown in cultivation medium and produces Z11-14:OAc. The gene encodes for example the Δ11 desaturase from the oblique banded leaf roller moth Choristoneura rosaceana (SEQ ID NO: 65). The pheromone is recovered from the broth and formulated into mating disruption product to control pests, as e.g., European corn borer Ostrinia nubilalis.

Example 8: Method to Produce E11-C14:OAc

A gene, encoding a Δ11 desaturase that preferentially produces E11-C14:CoA is overexpressed in a yeast strain along with HarFAR and Atf1. The resulting strain is grown in cultivation medium and produces E11-14:OAc. The gene encodes for example the Δ11 desaturase from the spotted fireworm moth Choristoneura parallela (SEQ ID NO: 66). The pheromone is recovered from the broth and formulated into mating disruption product to control pests, as e.g., lightbrown apple moth Epiphyas postvittana.

Example 9: Construction of Plasmids and Yarrowia lipolytica Strains

Genes encoding desaturases from Amyelois transitella (SEQ ID NO: 68), Spodoptera litura (SEQ ID NO: 12) and Drosophila melanogaster(Dmd9; SEQ ID NO: 10), the fatty acyl reductase of Helicoverpa armigera (HarFAR; SEQ ID NO: 25), the thioesterases from Escherichia coli (SEQ ID NO: 42) and from Cinnamomum camphora (SEQ ID NO: 40) and the alcohol acetyltransferase of Saccharomyces cerevisiae (Atf1; SEQ ID NO: 21) were synthesized by GeneArt (Life Technologies) in codon-optimized versions for Y. lipolytica. The fatty acyl reductase of Heliothis subflexa was synthesized by GeneArt (Life technologies) in codon-optimized version for Saccharomyces cerevisiae (SEQ ID NO: 70).

In strain ST6629 the open-reading frame of genes HFD4 (YALI0B01298g), HFD3 (YALI0Δ17875), HFD2 (YALI0E15400) and HFD1 (YALI0F23793g), as well as nucleotides −1130 to −100 upstream of the coding sequence of GPAT (YALI0C00209g) were deleted. A premature Stop-codon and frame-shift was introduced into PEX10 (YALI0C01023g) and FAO1 (YALI0B14014g) resulting in non-functional genes.

Strain ST7394 is based on ST6629 and expresses Dmd9, HarFAR and Atf1 as described in pCfB6969 and pCfB7600 (FIG. 2) from intergenic regions on chromosomes C (nucleotides 2192680-2193710) and D (nucleotides 1842294-1843343).

In strain ST6365, the open-reading frames of HFD1, HFD4, PEX10, and FAO1 were replaced with selection marker cassettes. ST6365 expressed the 411 desaturase of A. transitella and fatty acyl reductase from Heliothis subflexa.

Figure 2:
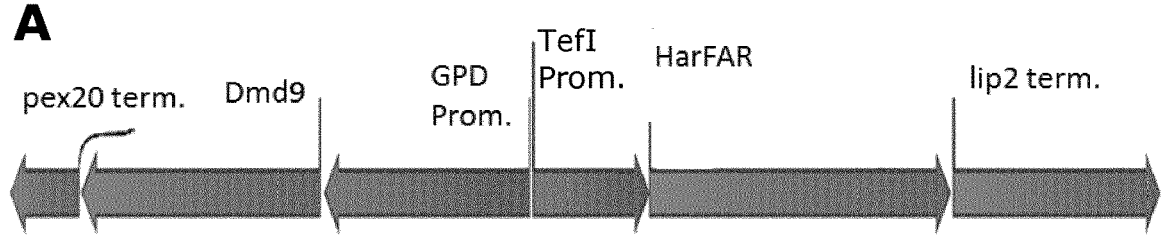
FIG. 2: expression cassettes. A: expression cassette of Dmd9 and HarFAR (encoded on plasmid pCfB6969). B: Expression cassette of Atf1 (encoded on plasmid pCfB7600). C: Expression cassettes of LIP2, LIP7, or LIP5. "Term." Stands for terminator; "prom." Stands for promoter. D: Expression cassette of Atf1 and Dmd9 (pCfB7235). E: Expression cassette of Dmd9 (pCfB7239). F: Expression cassette of SliDes11 (pCfB7240). G: Expression cassette of TesA(LL)/CfFATB1 and Dmd9 (pCfB7251/pCfB7253).
Figure 2:
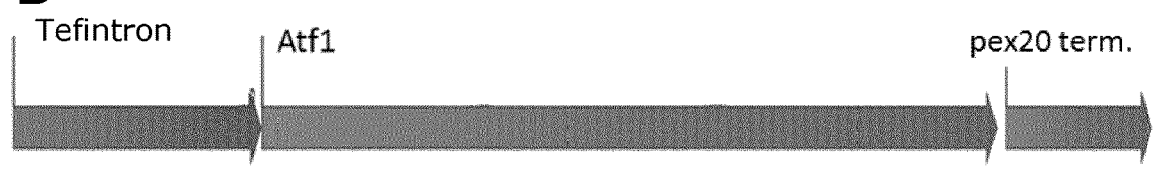
Figure 2:
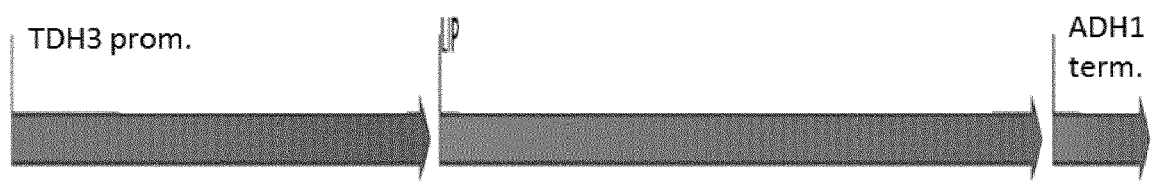
Figure 2:
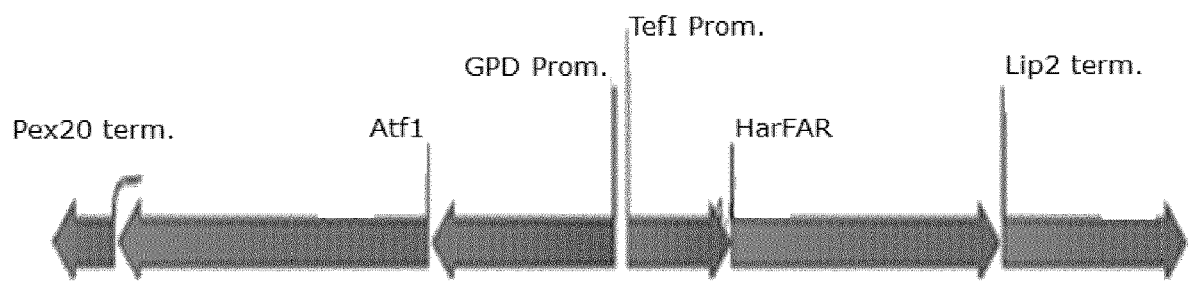

Strain ST6357 expresses Atf1 and HarFAR from an intergenic region on chromosome E (nucleotides 1722042-1723055) as described in pCfB7235 (FIG. 2).

Strain ST6359 expresses Atf1 and HarFAR from an intergenic region on chromosome E (nucleotides 1722042-1723055) as described in pCfB7235 (FIG. 2) and Dmd9 from an intergenic region on chromosome E (2881519-2882566) as described in pCfB7239 (FIG. 2).

Strain ST6360 expresses Atf1 and HarFAR from an intergenic region on chromosome E (nucleotides 1722042-1723055) as described in pCfB7235 and SliDes11 from an intergenic region on chromosome E (2881519-2882566) as described in pCfB7240 (FIG. 2).

Strain ST6373 expresses Atf1 and HarFAR from an intergenic region on chromosome E (nucleotides 1722042-1723055) as described in pCfB7235 and Dmd9 and TesA (LL) from an intergenic region on chromosome E (2881519-2882566) as described in pCfB7251 (FIG. 2).

Strain ST6375 expresses Atf1 and HarFAR from an intergenic region on chromosome E (nucleotides 1722042-1723055) as described in pCfB7235 and Dmd9 and CcFATB1 from an intergenic region on chromosome E (2881519-2882566) as described in pCfB7253 (FIG. 2).

In strain ST7010 nucleotides 3658-3660 (ATC) of Y. lipolytica's native fatty acyl synthetase 2 gene (YAL119382) were replaced by TTC.

In strain ST7895 and ST7944 the open-reading frames of genes LIP2 and LIP2 LIP8 were deleted, respectively.

Example 10: Method for Increasing the Production of (Z)9-14:OH and (Z)9-14:Ac in *Yarrowia lipolytica* by Heterologous Expression of Thioesterases The strains in table 9 were inoculated into 2 mL YPG medium (20 g/L peptone, 10 g/L yeast extract and 70 g/L glycerol) to an optical density (600 nm) of 1 and cultivated in 12-ml glass tubes (Duran, Wertheim, Germany) with metal labocap lids (Lüdiswiss, Flawil, Switzerland) for 48 hours at 30° C. shaken at 250 rpm. If indicated the medium was supplemented with 1 g/L methyl myristate.

For fatty alcohol extraction, 1 mL of culture was transferred into a 4-mL glass vial and 10 µL of internal standard solution (2 µg/µL (Z)-10-heptan-1-yl methyl ester in 100% ethanol) was added. The vials were covered with small pieces of aluminum foil and a needle was used to pierce small holes in the foil covers. The samples were vortexed and placed at −80° C. for storage until analysis. The samples were freeze-dried in a freeze dry system (Freezone6 and Stoppening tray dryer, Labconco, Kansas City, USA) at −40° C., then 1 mL chloroform:methanol 2:1 was added to disrupt the cells. The mix was vortexed for 45 s and left at room temperature for 4 hours. The organic solvents were evaporated slowly under a nitrogen stream. 1 ml of hexane was added, the samples were vortexed for 10 s, centrifuged and 200 µl were transferred to a new glass vial. Quantification was performed with a SCION TQ GC-MS (Bruker), equipped with an INNOWax 30 m×0.25 mm×0.25 µm column, with helium as carrier gas. The injector was configured in splitless mode at 250° C., the oven temperature was set to 80° C. for 1 min, then increased at a rate of 10° C./min to 210° C., followed by a hold at 210° C. for 10 min, and then increased at a rate of 10° C./min to 230° C. followed by a hold at 230° C. for 5 min. The MS was operated in electron impact mode (70 eV), scanning between m/z 30 and 350. Compounds were identified by comparison of retention times and mass spectra with those of reference compounds. Compounds were quantified by the Total Ion Current (TIC) recorded. Data were analyzed by the BrukerMSWorkstation software. The concentrations of fatty alcohols were calculated based on internal standards (Table 9).

The example shows the production of (Z)9-14:OH and (Z)9-14:OAc in the yeast *Y. lipolytica*. The additional expression of thioesterase either from *E. coli* or *C. camphora* increased the production of the compounds by 20% and 25%, respectively.

TABLE 9

Increased production of (Z)9-14:OH and (Z)9-14:OAc in *Yarrowia lipolytica* by heterologous expression of thioesterases.

| Strain | Over-expressed genes | Parent strain | Plasmids integrated | Media supplementation | (Z)9-14:OH (Z)9-16:OH (mg/L) | (Z)9-14:OAc (Z)11-16:OAc (mg/L) |
|---|---|---|---|---|---|---|
| ST3683 | *Yarrowia lipolytica* GB 20 (Angerer et al., 2014) | | | + methyl myristate | 0.1 ± 0.1 | 0.0 ± 0.0 |
| ST6357 | Har_FAR ATF1 | ST6365 | pCfB7235 | +methyl myristate | 11.5 ± 1.5 1.8 ± 0.3 | 8.8 ± 0.6 33.6 ± 1.2 |
| ST6359 | Dmd9 Har_FAR ATF1 | ST6365 | pCfB7239 pCfB7235 | +methyl myristate | 40.3 ± 7 1.2 ± 0.2 | 28 ± 1.0 22.6 ± 6.6 |
| ST6360 | Δ9 desaturase from *S. litura* Har_FAR ATF1 | ST6365 | pCfB7240 pCfB7235 | +methyl myristate | 27.5 ± 0.9 3.6 ± 3.8 | 15.2 ± 0.8 98.6 ± 0.07 |
| ST6373 | Dmd9 Har_FAR ATF1 Thioesterase from *E. coli* | ST6365 | pCfB7251 pCfB7235 | +methyl myristate | 83.3 ± 10.3 N.A. | 50.7 ± 2.8 N.A. |
| ST6375 | Dmd9 Har_FAR ATF1 Thioesterase from *C. camphora* | ST6365 | pCfB7253 pCfB7235 | +methyl myristate | 88.4 ± 5.8 N.A. | 50.6 ± 1.0 N.A. |

In the two right columns, the upper line indicates products in C14, the lower line products in C16.
N.A.: not available.

Example 11: Method for Increasing Production of (Z)9-14:OH in *Yarrowia lipolytica* by Introducing Point Mutation in *Yarrowia lipolytica* Fatty Acyl Synthetase (FAS2)

The strains in table 10 were cultivated as described in example 10, but the medium was not supplemented.

By introducing a point mutation (I1220F) in the native fatty acyl synthetase (FAS2) production of (Z)9-14:OH increased approximately 15 fold.

TABLE 10

| Strain | Overexpressed genes | Parent strain | Plasmids integrated | (Z)9-14:OH (mg/L) | (Z)9-14:OAc (mg/L) |
|---|---|---|---|---|---|
| ST6713 | Δ9 desaturase from *D. melanogaster* Fatty acyl reductase from *H. armigera* | ST6629 | pCfB6969 | 4.9 ± 1.4 | — |
| ST7010 | Δ9 desaturase from *D. melanogaster* Fatty acyl reductase from *H. armigera* YLFAS2 (I1220F) | ST6629 | pCfB6969 | 73.6 ± 16.2 | — |

Figure 3:
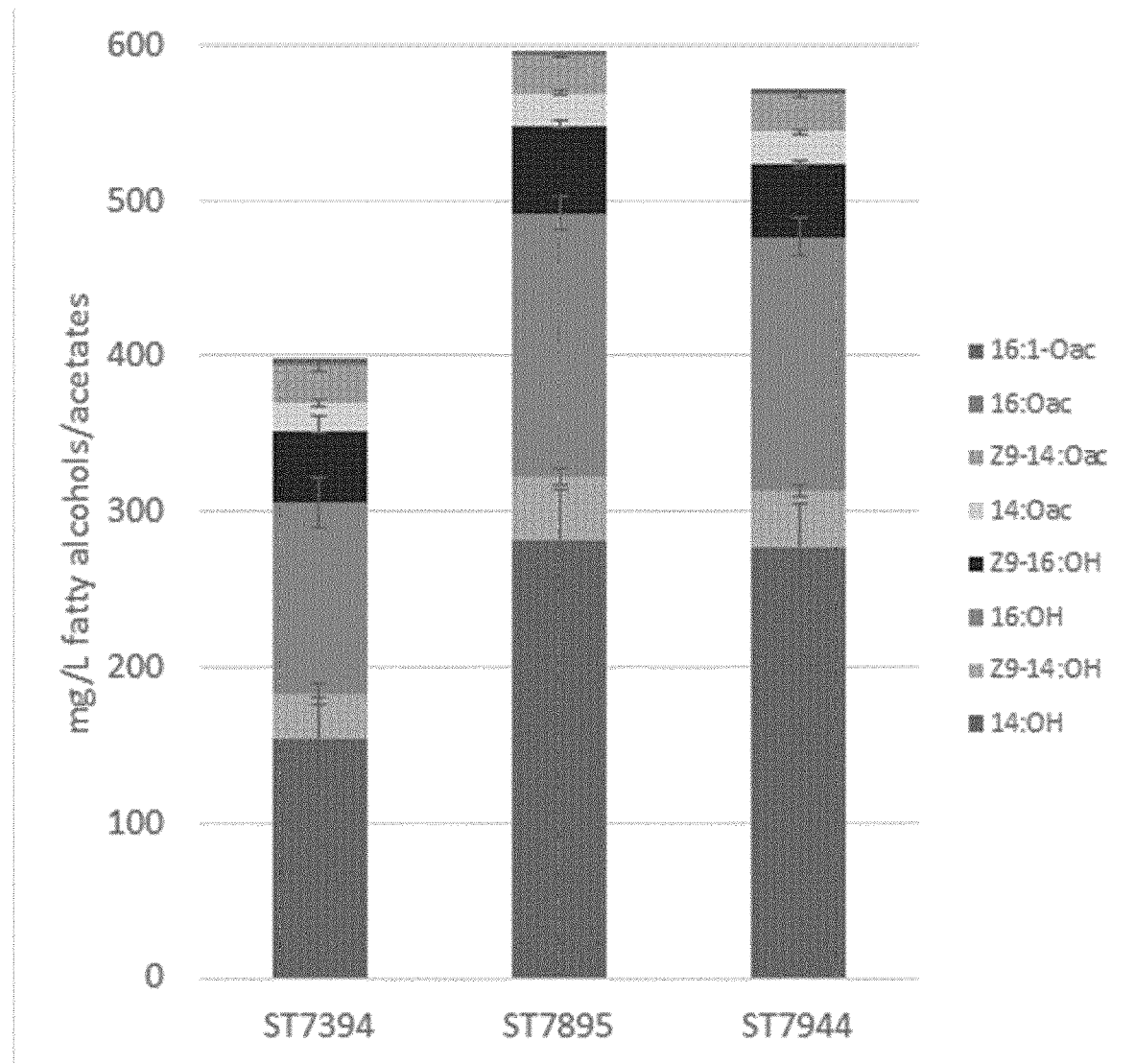
FIG. 3: Deletion of lipase genes in *Y. lipolytica* increases fatty alcohol titres.
Figure 3:
Figure 3:
Figure 3:
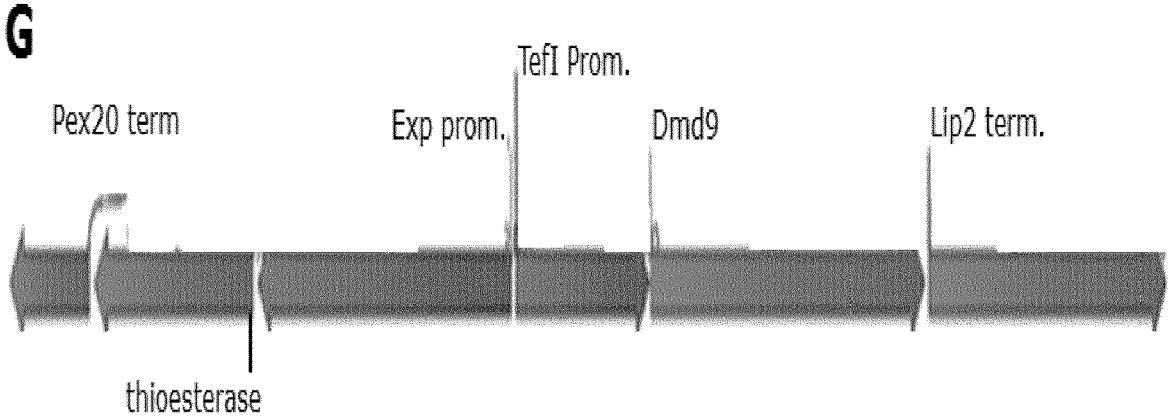

Example 12: Method for Increasing Production of (Z)9-14:Ac in *Yarrowia lipolytica* by Deletion of *Yarrowia lipolytica* Lipase Genes The stains in table 11 were cultivated as described in example 10. The medium was supplemented with 1 g/L methyl myristate. Deletion of lipase 2 alone or lipase 2 and lipase 8 together resulted in increased fatty alcohol titers, as can be seen in FIG. 3.

TABLE 11

| Strain | Overexpressed genes | Parent strain | Plasmids integrated |
|---|---|---|---|
| ST7394 | Δ9 desaturase from *D. melanogaster* Fatty acyl reductase from *H. armigera* Alcohol acetyltransferase from *S. cerevisiae* | ST6629 | pCfB6969 pCfB7600 |
| ST7895 | Δ9 desaturase from *D. melanogaster* Fatty acyl reductase from *H. armigera* Alcohol acetyltransferase from *S. cerevisiae* Δlip2 | ST6629 | pCfB6969 pCfB7600 |
| ST7944 | Δ9 desaturase from *D. melanogaster* Fatty acyl reductase from *H. armigera* Alcohol acetyltransferase from *S. cerevisiae* Δlip2 Δlip8 | ST6629 | pCfB6969 pCfB7600 |

Sequences

Overview

SEQ ID NO: 1—*Y. lipolytica* codon-optimized nucleotide sequence of Δ9 desaturase from *Pelargonium hortorum*
SEQ ID NO: 2—Δ9 desaturase from *Pelargonium hortorum*
SEQ ID NO: 3—*Y. lipolytica* codon-optimized nucleotide sequence of Δ9 desaturase from *Ricinus communis*
SEQ ID NO: 4—Δ9 desaturase from *Ricinus communis*
SEQ ID NO: 5—*S. cerevisiae* codon-optimized nucleotide sequence of Δ9 desaturase from *Amyelois transitella* Atr236
SEQ ID NO: 6—Δ9 desaturase from *Amyelois transitella* Atr236
SEQ ID NO: 7—*S. cerevisiae* codon-optimized nucleotide sequence of Δ9 desaturase from *Amyelois transitella* Atr1432
SEQ ID NO: 8—Δ9 desaturase from *Amyelois transitella* Atr1432
SEQ ID NO: 9—*S. cerevisiae* codon-optimized nucleotide sequence of Δ9 desaturase from *Drosophila melanogaster* Dmd9
SEQ ID NO: 10—Δ9 desaturase from *Drosophila melanogaster* Dmd9
SEQ ID NO: 11—*Y. lipolytica* codon-optimized nucleotide sequence of Δ9 desaturase from *Spodoptera litura* Des11
SEQ ID NO: 12—Δ9 desaturase from *Spodoptera litura* Des11
SEQ ID NO: 13—*Y. lipolytica* codon-optimized nucleotide sequence of Δ9 desaturase from *Chauliognathus lugubris* Cld9
SEQ ID NO: 14—Δ9 desaturase from *Chauliognathus lugubris* Cld9
SEQ ID NO: 15—*Y. lipolytica* codon-optimized nucleotide sequence of desaturase from *Tribolium castaneum* D6
SEQ ID NO: 16—desaturase from *Tribolium castaneum* D6
SEQ ID NO: 17—*Y. lipolytica* codon-optimized nucleotide sequence of desaturase from *Tribolium castaneum* D8
SEQ ID NO: 18—desaturase from *Tribolium castaneum* D8
SEQ ID NO: 19—*Saccharomyces cerevisiae* ATF1 DNA sequence; DNA coding sequence.
SEQ ID NO: 20—*Y. lipolytica* codon-optimized nucleotide sequence of alcohol acetyltransferase from *S. cerevisiae* ATF1
SEQ ID NO: 21—*Saccharomyces cerevisiae* ATF1p amino acid sequence
SEQ ID NO: 22—*Y. lipolytica* codon-optimized nucleotide sequence of thioesterase from *Cuphea palustris* CpFATB2
SEQ ID NO: 23—protein sequence of thioesterase from *Cuphea palustris* CpFATB2
SEQ ID NO: 24—*S. cerevisiae*-codon-optimized nucleotide sequence of *Helicoverpa armigera* fatty acyl reductase; mRNA-coding sequence
SEQ ID NO: 25—*H. armigera* fatty acyl reductase
SEQ ID NO: 26—*S. cerevisiae*-codon-optimized nucleotide sequence of *H. armigera* fatty acyl reductase with signal peptide changed to HDEL; DNA coding sequence.
SEQ ID NO: 27—*H. armigera* fatty acyl reductase with signal peptide changed to HDEL
SEQ ID NO: 28—*S. cerevisiae*-codon-optimized nucleotide sequence of *H. assulta* fatty acyl reductase; mRNA-coding sequence.
SEQ ID NO: 29—Amino acid sequence of *H. assulta* fatty acyl reductase
SEQ ID NO: 30—*S. cerevisiae*-codon-optimized nucleotide sequence of *Helicoverpa assulta* fatty acyl reductase with signal peptide changed to HDEL; mRNA-coding sequence
SEQ ID NO: 31—amino acid sequence of *H. assulta* fatty acyl reductase with signal peptide changed to HDEL
SEQ ID NO: 32—*S. cerevisiae*-codon-optimized nucleotide sequence of *Heliothis subflexa* fatty acyl reductase; mRNA-coding sequence.
SEQ ID NO: 33—Amino acid sequence of *H. subflexa* fatty acyl reductase SEQ ID NO: 34—*S. cerevisiae*-codon-optimized nucleotide sequence of *H. subflexa* fatty acyl reductase with signal peptide changed to HDEL; mRNA-coding sequence SEQ ID NO: 35—amino acid sequence of *H. subflexa* fatty acyl reductase with signal peptide changed to HDEL SEQ ID NO: 36—*Y. lipolytica* codon-optimized nucleotide sequence of Δ9 desaturase from *Drosophila melanogaster* Dmd9

SEQ ID NO: 37—*Y. lipolytica* codon-optimised nucleotide sequence of thioesterase from *Cuphea hookeriana* ChFatB3

SEQ ID NO: 38—amino acid sequence of thioesterase from *Cuphea hookeriana* ChFatB3

SEQ ID NO: 39—*Y. lipolytica* codon-optimised nucleotide sequence of thioesterase from *Cinnamomum camphora* CcFatB1

SEQ ID NO: 40—amino acid sequence of thioesterase from *Cinnamomum camphora* CcFatB1

SEQ ID NO: 41—*Y. lipolytica* codon-optimized nucleotide sequence of thioesterase from *Escherichia coli* TesA, without the leader sequence, named TesA(LL)

SEQ ID NO: 42—protein sequence of thioesterase from *Escherichia coli* TesA, without the leader sequence, named TesA(LL)

SEQ ID NO: 43—*Y. lipolytica* codon-optimized nucleotide sequence of fatty acyl reductase from *H. armigera* Har_FAR SEQ ID NO: 44—*Y. lipolytica* codon-optimized nucleotide sequence of fatty acyl reductase from *Bicyclus anynana* Ban-wFAR2

SEQ ID NO: 45—protein sequence of fatty acyl reductase from *Bicyclus anynana* Ban-wFAR2

SEQ ID NO: 46—PR-1852 (PTDH3_fw)

SEQ ID NO: 47 PR-1853 (PTDH3_rv)

SEQ ID NO: 48 PR-1565 (PTEF1)

SEQ ID NO: 49 PR-8332 (Har_FAR_U1_fw)

SEQ ID NO: 50 PR-10739 (Har_FAR_HDEL_U1_rev)

SEQ ID NO: 51 PR-14318 (Phd9_U2_fw)

SEQ ID NO: 52 PR-14276 (Phd9_U2_rev)

SEQ ID NO: 53 PR-14319 (RCd9_U2_fw)

SEQ ID NO: 54 PR-14278 (RCd9_U2_rev)

SEQ ID NO: 55 PR-14320 (Atf1_U2_fw)

SEQ ID NO: 56 PR-14321 (Atf1_U2_rev)

SEQ ID NO: 57 PR-15974 (Dmd9_U1_fw)

SEQ ID NO: 58 PR-15975 (Dmd9_U1_rev)

SEQ ID NO: 59 PR-15976 (attB1_Dmd9_F)

SEQ ID NO: 60 PR-15977 (attB2_Dmd9_R)

SEQ ID NO: 61 PR-15978 (attB1_Phd9_F)

SEQ ID NO: 62 PR-15979 (attB2_Phd9_R)

SEQ ID NO: 63 PR-15980 (attB1_Rcd9_F)

SEQ ID NO: 64 PR-15981 (attB1_Rcd9_R)

SEQ ID NO: 65 Δ11 desaturase from *Choristoneura rosaceana*.

SEQ ID NO: 66—Δ11 desaturase from *Choristoneura parallela*

SEQ ID NO: 67—*Y. lipolytica* codon-optimized nucleotide sequence of *Amyelois transitella* Δ11 desaturase SEQ ID NO: 68—Δ11 desaturase from *Amyelois transitella*

SEQ ID NO: 69—*Y. lipolytica* codon-optimized nucleotide sequence of *Helicoverpa armigera* fatty acyl reductase SEQ ID NO: 70—*S. cerevisiae* codon-optimized nucleotide sequence of *Heliothis subflexa* fatty acyl reductase SEQ ID NO: 71: FAS2 sequence (wild type)

SEQ ID NO: 72: Sequence of LIP2 from *Yarrowia lipolytica*.

SEQ ID NO: 73: Sequence of LI P7 from *Y. lipolytica*

SEQ ID NO: 74: Sequence of LI P8 from *Y. lipolytica*

REFERENCES

Alfaro, Navarro-Llopis, Primo, 2009. Optimization of pheromone dispenser density for managing the rice striped stem borer, *Chilo suppressalis* (Walker), by mating disruption. Crop Protection. 28:567-572.

Bari, 2003. Development of pheromone mating disruption strategies for the suppression of the artichoke plume moth in artichokes grown on the central coast of California. ISHS Acta Horticulturae 660: V International Congress on Artichoke. doi: 10.17660/ActaHortic.2004.660.80

Eizaguirre, Sans, López, Albajes. 2002. Effects of mating disruption against the Mediterranean corn borer, *Sesamia nonagrioides*, on the European corn borer *Ostrinia nubilalis*. Use of pheromones and other semiochemicals in integrated production IOBC wprs Bulletin.

Ferrell, Yao, 1972. Reductive and oxidative synthesis of saturated and unsaturated fatty aldehydes, J Lipid Res. 13(1):23-6).

Gietz R D, Schiestl R H. High-efficiency yeast transformation using the LiAc/SS carrier DNA/PEG method. Nat Protoc. 2007; 2(1):31-4.

Jessop-Fabre M M, Jakočiūnas T, Stovicek V, Dai Z, Jensen M K, Keasling J D, Borodina I. EasyClone-MarkerFree: A vector toolkit for marker-less integration of genes into *Saccharomyces cerevisiae* via CRISPR-Cas9. Biotechnol J. 2016 August; 11(8):1110-7.

Jensen, Strucko, Kildegaard, David, Maury, Mortensen, Forster, Nielsen, Borodina, 2014. EasyClone: method for iterative chromosomal integration of multiple genes in *Saccharomyces cerevisiae*, FEMS Yeast Res. 14(2):238-48

Kehat, Dunkelblum, 1993. Sex Pheromones: achievements in monitoring and mating disruption of cotton pests in Israel, Achieves of Insect Biochemistry and Physiology. 22:425-431.

Li, Zhang, 2009. An environmentally benign TEMPO-catalyzed efficient alcohol oxidation system with a recyclable hypervalent iodine(III) reagent andilts facile preparation. Synthesis, 1163-1169a.

Meyer, Schreiber, 1994. Acceleration of the Dess-Martin oxidation by water J. Org. Chem., 59, 7549-7552;

Mitchell & McLaughlin (1982), "Suppression of Mating and Oviposition by Fall Armyworm and Mating by Corn Earworm in Corn, Using the Air Permeation Technique", Journal of Economic Entomology, 75(2):270-274

Okada, Asawa, Sugiyama, Kirihara, Iwai, Kimura, 2014. Sodium hypochlorite pentahydrate (NaOCl.5H2O) crystals as an extraordinary oxidant for primary and secondary alcohols. Synlett, 25, 596-598.

Schneiter, R., Tatzer, V., Gogg, G., Leitner, E., Kohlwein, S. D., 2000. Elo1p-dependent carboxy-terminal elongation of $C14:\Delta^9$ to $C16:\Delta^{11}$ fatty acids in *Saccharomyces cerevisiae*. J. Bacteriol. 182, 3655-3660.

Steves J. E. and Stahl S. S., 2013. Copper(I)/ABNO-catalyzed aerobic alcohol oxidation: alleviating steric and electronic constraints of Cu/TEMPO catalyst systems. J. Am. Chem. Soc., 135, 15742-15745

Stovicek V, Borja G M, Forster J, Borodina I. EasyClone 2.0: expanded toolkit of integrative vectors for stable gene expression in industrial *Saccharomyces cerevisiae* strains. J Ind Microbiol Biotechnol. 2015 November; 42(11): 1519-31.

Tamura, Aoyama, Takido, Kodomari, 2012. Novel [4-Hydroxy-TEMPO+NaCl]/SiO2 as a reusable catalyst for aerobic oxidation of alcohols to carbonyls. Synlett, 23, 1397-1407.

Wu, Zhang, Yao, Xu, Wang and Zhang, 2012. Management of diamondback moth, *Plutella xylostella* (Lepidoptera: Plutellidae) by mating disruption. Insect Science 19 (6), 643-648.

Yadav, Reddy, Basak, Narsaiah, 2004. Recyclable 2nd generation ionic liquids as green solvents for the oxidation of alcohols with hypervalent iodine reagents, Tetrahedron, 60, 2131-2135.

Items

1. A yeast cell capable of producing a desaturated fatty alcohol and optionally a desaturated fatty alcohol acetate, said yeast cell expressing:
   i) at least one heterologous desaturase capable of introducing at least one double bond in a fatty acyl-CoA having a carbon chain length of 14; and
   ii) at least one heterologous fatty acyl-CoA reductase (FAR), capable of converting at least part of said desaturated fatty acyl-CoA to a desaturated fatty alcohol; and
   iii) optionally an acetyltransferase capable of converting at least part of said desaturated fatty alcohol to a desaturated fatty alcohol acetate;
   wherein the desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA.

2. The yeast cell according to item 1, wherein the at least one heterologous desaturase is selected from the group consisting of a Δ3 desaturase, a Δ5 desaturase, a Δ6 desaturase, a Δ7 desaturase, a Δ8 desaturase, a Δ9 desaturase, a Δ10 desaturase, a Δ11 desaturase, a Δ12 desaturase and a Δ13 desaturase.

3. The yeast cell according to any one of the preceding items, wherein the desaturase is capable of introducing at least one double bond in position 5, 6, 7, 8, 9, 10, 11, 12 or 13.

4. The yeast cell according to any one of the preceding items, wherein the desaturase is derived from an organism selected from *Pelargonium hortorum, Ricinus communis, Drosophila melanogaster, Spodoptera litura* and *Tribolium castaneum*, preferably the desaturase is derived from *Drosophila melanogaster*.

5. The yeast cell according to any one of the preceding items, wherein the at least one heterologous desaturase is selected from the group consisting of:
   i) a Δ9 desaturase having at least 60% homology to the Δ9 desaturase from *Pelargonium hortorum* as set forth in SEQ ID NO: 2;
   ii) a Δ9 desaturase having at least 60% homology to the Δ9 desaturase from *Ricinus communis* as set forth in SEQ ID NO: 4;
   iii) a Δ9 desaturase having at least 60% homology to the Δ9 desaturase from *Drosophila melanogaster* as set forth in SEQ ID NO: 10;
   iv) a Δ9 desaturase having at least 60% homology to the Δ9 desaturase from *Spodoptera litura* as set forth in SEQ ID NO: 12;
   v) a Δ9 desaturase having at least 60% homology to the Δ9 desaturase from *Chauliognathus lugubris* as set forth in SEQ ID NO: 14;
   vi) a desaturase having at least 60% homology to the desaturase from *Tribolium castaneum* as set forth in SEQ ID NO: 16; and
   vii) a desaturase having at least 60% homology to the desaturase from *Tribolium castaneum* as set forth in SEQ ID NO: 18;
   viii) a Δ11 desaturase having at least 60% homology to the desaturase from *Choristoneura rosaceana* as set forth in SEQ ID NO: 65;
   ix) a Δ11 desaturase having at least 60% homology to the desaturase from *Choristoneura parallela* as set forth in SEQ ID NO: 66,
   preferably the desaturase is a Δ9 desaturase having at least 60% homology to the Δ9 desaturase from *Drosophila melanogaster* as set forth in SEQ ID NO: 10 or a Δ9 desaturase having at least 60% homology to the Δ9 desaturase from *Spodoptera litura* as set forth in SEQ ID NO: 12.

6. The yeast cell according to any one of the preceding items, wherein the at least one heterologous desaturase is selected from the group consisting of:
   i) a Δ9 desaturase having at least 60% homology to the Δ9 desaturase from *Drosophila melanogaster* as set forth in SEQ ID NO: 10;
   ii) a Δ9 desaturase having at least 60% homology to the Δ9 desaturase from *Spodoptera litura* as set forth in SEQ ID NO: 12;
   iii) a Δ9 desaturase having at least 60% homology to the Δ9 desaturase from *Chauliognathus lugubris* as set forth in SEQ ID NO: 14;
   iv) a desaturase having at least 60% homology to the desaturase from *Tribolium castaneum* as set forth in SEQ ID NO: 16; and
   v) a desaturase having at least 60% homology to the desaturase from *Tribolium castaneum* as set forth in SEQ ID NO: 18;
   vi) a Δ11 desaturase having at least 60% homology to the desaturase from *Choristoneura rosaceana* as set forth in SEQ ID NO: 65;
   vii) a Δ11 desaturase having at least 60% homology to the desaturase from *Choristoneura parallela* as set forth in SEQ ID NO: 66.

7. The yeast cell according to any one of the preceding items, wherein the fatty acyl-CoA reductase (FAR) is selected from:
   i) a FAR having at least 80% homology to the FAR from *Helicoverpa armigera* as set forth in SEQ ID NO: 25 or SEQ ID NO: 27;
   ii) a FAR having at least 80% homology to the FAR from *Helicoverpa assulta* as set forth in SEQ ID NO: 29 or SEQ ID NO: 31;
   iii) a FAR having at least 80% homology to the FAR from *Heliothis subflexa* as set forth in SEQ ID NO: 33 or SEQ ID NO: 35; and
   iv) a FAR having at least 80% homology to the FAR from *Bicyclus anynana* as set forth in SEQ ID NO: 45,
   preferably the FAR is a FAR having at least 80% homology to the FAR from *Helicoverpa armigera* as set forth in SEQ ID NO: 25 or SEQ ID NO: 27.

8. The yeast cell according to any one of the preceding items, wherein the acetyltransferase is a heterologous acetyltransferase expressed from said yeast cell or a native acetyltransferase overexpressed from said yeast cell.

9. The yeast cell according to any one of the preceding items, wherein the acetyltransferase has at least 75% homology to the acetyltransferase Atf1 from *Saccharomyces cerevisiae* as set forth in SEQ ID NO: 21.

10. The yeast cell according to any one of the preceding items, wherein the yeast is of a genus selected from *Saccharomyces, Pichia, Yarrowia, Kluyveromyces, Candida, Rhodotorula, Rhodosporidium, Cryptococ-* cus, *Trichosporon* and *Lipomyces*, preferably the genus is *Saccharomyces* or *Yarrowia*, most preferably the genus is *Yarrowia*.

11. The yeast cell according to any one of the preceding items, wherein the yeast is of a species selected from *Saccharomyces cerevisiae, Pichia pastoris, Kluyveromyces marxianus, Cryptococcus albidus, Lipomyces lipofera, Lipomyces starkeyi, Rhodosporidium toruloides, Rhodotorula glutinis, Trichosporon pullulan* and *Yarrowia lipolytica*, preferably the yeast cell is a *Saccharomyces cerevisiae* cell or a *Yarrowia lipolytica* cell, most preferably the yeast cell is a *Yarrowia lipolytica* cell.

12. The yeast cell according to any one of the preceding items, wherein the cell:
i) expresses a Δ9 desaturase identical to or having at least 60% homology to the Δ9 desaturase from *Drosophila melanogaster* as set forth in SEQ ID NO: 10; and
ii) expresses a fatty acyl-CoA reductase identical to or having at least 80% homology to the fatty acyl-CoA reductase from *Helicoverpa armigera* as set forth in SEQ ID NO: 25; and
iii) expresses or overexpresses an acetyltransferase identical to or having at least 75% homology to the acetyltransferase from *Saccharomyces cerevisiae* as set forth in SEQ ID NO: 21.

13. The yeast cell according to any one of the preceding items, wherein the acetyltransferase is overexpressed compared to a wild type yeast cell.

14. The yeast cell of any one of the preceding items, wherein the genes encoding the desaturase, the fatty acyl-CoA reductase, or the acetyltransferase are comprised within the genome of said yeast cell or within one or more vector comprised within said yeast cell.

15. The yeast cell of any one of the preceding items, wherein the yeast cell further expresses or overexpresses a thioesterase.

16. The yeast cell of any one of the preceding items, wherein the thioesterase has at least 60% homology to the thioesterase from *Cuphea palustris* as set forth in SEQ ID NO: 23, to the thioesterase from *Cuphea hookeriana* as set forth in SEQ ID NO: 38, to the thioesterase from *Cinnamomum camphora* as set forth in SEQ ID NO: 40, or to the thioesterase from *Escherichia coli* as set forth in SEQ ID NO: 42, preferably the thioesterase has at least 60% homology to the thioesterase from *Cinnamomum camphora* as set forth in SEQ ID NO: 40, or to the thioesterase from *Escherichia coli* as set forth in SEQ ID NO: 42.

17. The yeast cell of any one of the preceding items, wherein the yeast cell further expresses a fatty acyl synthase variant having a modified ketone synthase domain, whereby the variant preferably binds shorter fatty acids.

18. The yeast cell of any one of the preceding items, said yeast cell further having a mutation resulting in partial or total loss of activity of one or more lipases.

19. The yeast cell according to item 18, wherein the one or more lipases has at least 60% homology to lipase 2 of *Yarrowia lipolytica* as set forth in SEQ ID NO: 72, lipase 7 of *Yarrowia lipolytica* as set forth in SEQ ID NO: 73, or lipase 8 of *Yarrowia lipolytica* as set forth in SEQ ID NO: 74.

20. The yeast cell according to any one of items 18 to 19, wherein the yeast cell is *Yarrowia lipolityca* and the one or more lipases are selected from the group consisting of lipase 2 as set forth in SEQ ID NO: 72, lipase 7 as set forth in SEQ ID NO: 73 and lipase 8 as set forth in SEQ ID NO: 74.

21. The yeast cell of any one of the preceding items, wherein at least one of the genes encoding the desaturase, the fatty acyl-CoA reductase, the acetyltransferase or the thioesterase is present in high copy number.

22. The yeast cell of any one of the preceding items, wherein at least one of the genes encoding the desaturase, the fatty acyl-CoA reductase, the acetyltransferase or the thioesterase is under the control of an inducible promoter.

23. The yeast cell of any one of the preceding items, wherein at least one of the genes encoding the desaturase, the fatty acyl-CoA reductase, the acetyltransferase or the thioesterase is codon-optimised for said yeast cell.

24. A method for production of a desaturated fatty acid and optionally a desaturated fatty alcohol acetate in a yeast cell, said method comprising the steps of providing a yeast cell and incubating said yeast cell in a medium, wherein the yeast cell expresses:
i) at least one heterologous desaturase capable of introducing at least one double bond in a fatty acyl-CoA having a carbon chain length of 14, thereby converting at least part of said fatty acyl-CoA to a desaturated fatty acyl-CoA; and
ii) at least one heterologous fatty acyl-CoA reductase, capable of converting at least part of said desaturated fatty acyl-CoA to a desaturated fatty alcohol, thereby producing said desaturated fatty alcohol; and
iii) optionally an acetyltransferase capable of converting at least part of said desaturated fatty alcohol to a desaturated fatty alcohol acetate, thereby producing said desaturated fatty alcohol acetate;
wherein the desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA.

25. The method according to item 24, wherein the yeast cell is as defined in any one of items 1 to 23.

26. The method according to any one of items 24 to 25, wherein the ratio of desaturated tetradecanoyl-CoA to desaturated hexadecanoyl-CoA is of at least 0.1, such as at least 0.2, such as at least 0.3, such as at least 0.4, such as at least 0.5, such as at least 0.75, such as at least 1, such as at least 2, such as at least 3, such as at least 4, such as at least 5, such as at least 6, such as at least 7, such as at least 8, such as at least 9, such as at least 10, such as at least 12.5, such as at least 15.

27. The method according to any one of items 25 to 26, wherein the method yields desaturated fatty alcohols with a titre of at least 1 mg/L, such as at least 1.5 mg/L, such as at least 5 mg/L, such as at least 10 mg/L, such as at least 25 mg/L, such as at least 50 mg/L, such as at least 100 mg/L, such as at least 250 mg/L, such as at least 500 mg/L, such as at least 750 mg/L, such as at least 1 g/L, such as at least 2 g/L, such as at least 3 g/L, such as at least 4 g/L, such as at least 5 g/L, or more.

28. The method according to any one of items 25 to 27, wherein the method yields a desaturated fatty alcohol having a chain length of 14 with a titre of at least 1 mg/L, such as at least 1.5 mg/L, such as at least 5 mg/L, such as at least 10 mg/L, such as at least 25 mg/L, such as at least 50 mg/L, such as at least 100 mg/L, such as at least 250 mg/L, such as at least 500 mg/L, such as at least 750 mg/L, such as at least 1 g/L, such as at least 2 g/L, such as at least 3 g/L, such as at least 4 g/L, such as at least 5 g/L, or more.

29. The method according to any one of items 25 to 28, wherein the method yields desaturated fatty alcohol acetates with a titre of at least 1 mg/L, such as at least 1.5 mg/L, such as at least 5 mg/L, such as at least 10 mg/L, such as at least 25 mg/L, such as at least 50 mg/L, such as at least 100 mg/L, such as at least 250 mg/L, such as at least 500 mg/L, such as at least 750 mg/L, such as at least 1 g/L, such as at least 2 g/L, such as at least 3 g/L, such as at least 4 g/L, such as at least 5 g/L, or more.

30. The method according to any one of items 25 to 29, wherein the method yields a desaturated fatty alcohol acetate having a chain length of 14 with a titre of at least 1 mg/L, such as at least 1.5 mg/L, such as at least 5 mg/L, such as at least 10 mg/L, such as at least 25 mg/L, such as at least 50 mg/L, such as at least 100 mg/L, such as at least 250 mg/L, such as at least 500 mg/L, such as at least 750 mg/L, such as at least 1 g/L, such as at least 2 g/L, such as at least 3 g/L, such as at least 4 g/L, such as at least 5 g/L, or more.

31. The method according to any one of items 25 to 30, wherein the desaturated fatty alcohol acetates comprise at least 1% of a desaturated fatty alcohol acetate having a chain length of 14, such as at least 1.5%, such as at least 2%, such as at least 2.5%, such as at least 3%, such as at least 3.5%, such as at least 4%, such as at least 4.5%, such as at least 5%, such as at least 7.5%, such as at least 10%.

32. The method according to any one of items 25 to 31, wherein the yeast cell is further capable of expressing a thioesterase.

33. The method according to any one of items 25 to 32, wherein the thioesterase has at least 60% homology to the thioesterase from *Cuphea palustris* as set forth in SEQ ID NO: 23, to the thioesterase from *Cuphea hookeriana* as set forth in SEQ ID NO: 38, to the thioesterase from *Cinnamomum camphora* as set forth in SEQ ID NO: 40, or to the thioesterase from *Escherichia coli* as set forth in SEQ ID NO: 42.

34. The method according to any one of items 25 to 33, further comprising the step of recovering said desaturated fatty alcohol and/or desaturated fatty alcohol acetate.

35. The method according to any one of items 25 to 34, further comprising the step of formulating the recovered desaturated fatty alcohol and/or desaturated fatty alcohol acetate into a pheromone composition.

36. The method according to any one of items 25 to 35, wherein the pheromone composition further comprises one or more additional compounds such as a liquid or solid carrier or substrate.

37. A nucleic acid construct for modifying a yeast cell, said construct comprising:
    i) a first polynucleotide encoding at least one heterologous desaturase capable of introducing at least one double bond in a fatty acyl-CoA having a carbon chain length of 14; and
    ii) a second polynucleotide encoding at least one heterologous fatty acyl-CoA reductase (FAR), capable of converting at least part of said desaturated fatty acyl-CoA to a desaturated fatty alcohol; and
    iii) optionally a third polynucleotide encoding an acetyltransferase capable of converting at least part of said desaturated fatty alcohol to a desaturated fatty alcohol acetate, wherein optionally the first polynucleotide, the second polynucleotide and/or the third polynucleotide are under the control of a promoter.

38. A kit of parts comprising:
    a) the yeast cell according to any one of items 1 to 24 and instructions for use; and/or
    b) a nucleic acid construct according to item 37, wherein said construct is for modifying a yeast cell, and
    c) optionally the yeast cell to be modified.

39. A desaturated fatty alcohol obtainable by the method according to any one of items 25 to 36.

40. A desaturated fatty alcohol acetate obtainable by the method according to any one of items 35 to 36.

41. Use of a desaturated fatty alcohol according to any one of items 1 to 24 or 39.

42. Use of a desaturated fatty fatty alcohol acetate according to any one of items 1 to 24 or 40.

The invention claimed is:

1. A yeast cell capable of producing desaturated fatty alcohols, said yeast cell expressing:
   i) at least one heterologous fatty acyl-CoA desaturase capable of introducing at least one double bond in a fatty acyl-CoA having a carbon chain length of 14, wherein said desaturase is selected from the group consisting of a Δ9 desaturase and a Δ11 desaturase; and:
      a. has an amino acid sequence having at least 80% homology to the Δ9 desaturase from *Drosophila melanogaster* as set forth in SEQ ID NO: 10;
      b. has an amino acid sequence having at least 80% homology to the Δ9 desaturase from *Spodoptera litura* as set forth in SEQ ID NO: 12;
      c. has an amino acid sequence having at least 80% homology to the Δ11 desaturase from *Choristoneura parallela* as set forth in SEQ ID NO: 66; or
      d. has an amino acid sequence having at least 80% homology to the Δ11 desaturase from *Choristoneura rosaceana* as set forth in SEQ ID NO: 65; and
   ii) at least one heterologous fatty acyl-CoA reductase (FAR), capable of converting at least part of said desaturated fatty acyl-CoA to a desaturated fatty alcohol
wherein the fatty acyl-CoA desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA and wherein at least 10% of the desaturated fatty alcohols have a carbon chain length of 14.

2. The yeast cell according to claim 1, wherein the desaturase is obtained from an organism selected from the group consisting of *Drosophila melanogaster* and *Spodoptera litura*.

3. The yeast cell according to claim 1, wherein the fatty acyl-CoA reductase (FAR) is selected from:
   i) a FAR having an amino acid sequence having at least 80% homology to the FAR from *Helicoverpa armigera* as set forth in SEQ ID NO: 25 or SEQ ID NO: 27;
   ii) a FAR having an amino acid sequence having at least 80% homology to the FAR from *Helicoverpa assulta* as set forth in SEQ ID NO: 29 or SEQ ID NO: 31;
   iii) a FAR having an amino acid sequence having at least 80% homology to the FAR from *Heliothis subflexa* as set forth in SEQ ID NO: 33 or SEQ ID NO: 35; and
   iv) a FAR having an amino acid sequence having at least 80% homology to the FAR from *Bicyclus anynana* as set forth in SEQ ID NO: 45.

4. The yeast cell according to claim 1, further expressing an acetyltransferase capable of converting at least part of said desaturated fatty alcohol to a desaturated fatty alcohol acetate, wherein the acetyltransferase is a heterologous acetyltransferase expressed from said yeast cell or a native acetyltransferase overexpressed from said yeast cell.

5. The yeast cell according to claim 1, wherein the yeast is of a genus selected from *Saccharomyces, Pichia, Yarrowia, Kluyveromyces, Candida, Rhodotorula, Rhodosporidium, Cryptococcus, Trichosporon* and *Lipomyces*.

6. The yeast cell according to claim 1, wherein the yeast cell further expresses or overexpresses a thioesterase.

7. The yeast cell according to claim 1, wherein the yeast cell further expresses a fatty acyl synthase variant having a modified ketone synthase domain, whereby the yeast cell synthesises a higher proportion of C14 fatty acids than a yeast cell expressing a native fatty acyl synthase in the same conditions.

8. A method for production of a desaturated fatty alcohol in a yeast cell, said method comprising the steps of providing the yeast cell of claim 1 and incubating said yeast cell in a medium, wherein the yeast cell expresses:
   i) at least one heterologous desaturase capable of introducing at least one double bond in a fatty acyl-CoA having a carbon chain length of 14, wherein said desaturase is selected from the group consisting of a Δ9 desaturase and a Δ11 desaturase, thereby converting at least part of said fatty acyl-CoA to a desaturated fatty acyl-CoA; and ii) at least one heterologous fatty acyl-CoA reductase, capable of converting at least part of said desaturated fatty acyl-CoA to a desaturated fatty alcohol, thereby producing said desaturated fatty alcohol;

wherein the desaturase has a higher specificity towards tetradecanoyl-CoA than towards hexadecanoyl-CoA and/or wherein the fatty acyl-CoA reductase has a higher specificity towards desaturated tetradecanoyl-CoA than towards desaturated hexadecanoyl-CoA, thereby producing a desaturated fatty alcohol.

9. The method according to claim 8, further comprising the step of converting at least part of the desaturated fatty alcohol to a desaturated fatty alcohol acetate, wherein the conversion is a chemical conversion, thereby producing a desaturated fatty alcohol acetate.

10. The method according to claim 8, wherein the method yields a desaturated fatty alcohol having a chain length of 14 with a titre of at least 1 mg/L.

11. The yeast cell according to claim 1, further capable of producing a desaturated fatty alcohol acetate, said yeast cell further expressing an acetyltransferase capable of converting at least part of said desaturated fatty alcohol to a desaturated alcohol acyl acetate.

12. The yeast cell according to claim 1, wherein the yeast cell is a *Saccharomyces cerevisiae* cell or a *Yarrowia lipolytica* cell.

13. The yeast cell according to claim 7, wherein the yeast cell is a *Yarrowia lipolytica* cell and wherein the fatty acyl synthase variant is a fatty acid synthase (FAS2) variant comprising a mutation in FAS2 as set forth in the amino acid sequence as set forth in SEQ ID NO: 71.

14. The yeast cell according to claim 13, wherein the mutation in the amino acid sequence of FAS2 is a mutation at position 1220, 1217 or 1226 of FAS2 as set forth in SEQ ID NO: 71.

15. The yeast cell according to claim 14, wherein the mutation in the amino acid sequence as set forth in SEQ ID NO: 71 is an I1220F mutation, an I1220Y mutation, an I1220H mutation, an M1217F mutation, an M1217W mutation, an M1217Y mutation or an M1217H mutation.

16. The method according to claim 8, wherein the method is for production of a desaturated fatty alcohol and a desaturated fatty alcohol acetate in the yeast cell, wherein the yeast cell further expresses an acetyltransferase capable of converting at least part of said desaturated fatty alcohol to a desaturated fatty alcohol acetate.

17. The method according to claim 8, wherein the yeast cell is a *Saccharomyces cerevisiae* cell or a *Yarrowia lipolytica* cell.

18. The yeast cell according to claim 6, wherein the thioesterase has an amino acid sequence having at least 60% homology to the thioesterase from *Cinnamomum camphora* as set forth in SEQ ID NO: 40, or to the thioesterase from *Escherichia coli* as set forth in SEQ ID NO: 42.

\* \* \* \* \*

SEQUENCE LISTING

```
<160> NUMBER OF SEQ ID NOS: 74

<210> SEQ ID NO 1
<211> LENGTH: 1107
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1107)
<223> OTHER INFORMATION: Y.lipolytica codon-optimized nucleotide
      sequence of delta9 desaturase from Pelargonium hortorum

<400> SEQUENCE: 1
atgggcgtgc tgctgaacat ctgttcgtct cccttccccg tggtggcctc tgccgcctct      60
acctctatct ctaaggtgaa ccacatccga aaggtgggcg tgaccggcgt gatggctccc     120
cagaagatcg agatcttcaa gtctatggag gagtggggca agcacaacat cctgccgctg     180
gccaagcccg tcgagaagtc ttggcagcct accgacttcc tgcccgaccc ctcgtctgag     240
ggcttcatgg aggagtacaa cgccttcaag gagcgaactc gagagctgcc cgacgagtac     300
```

| | | | |
|---|---|---|---|
| ttcgtggtgc tggccggcga catgatcacc gaggaggccc tgcccaccta ccagaccctg | | | 360 |
| gtgaaccgac ccgacgaggt ggccgacgag actggccact ctgagtctcc ctgggccgtg | | | 420 |
| tggtcccgag cctggaccgc cgaggagaac cgacacggcg acctgctgaa caagtacctg | | | 480 |
| tacctgtctg gcaagctgga catgcgacag gtcgagaaga ccatccagta cctgatcgct | | | 540 |
| ctgggccagg acatcggcac cgagaagaac ccctaccacc tgttcatcta cacctcgttc | | | 600 |
| caggagcgag ccaccttcat ctctcacgcc aacaccgcca agctggccca gcagcacggc | | | 660 |
| gacaagcagc tggctcagat ctgcggcacc attgccgccg acgagaagcg acatgagact | | | 720 |
| gcctacaccc gaatcgtgga caagctgttc gagctggacc ccgacgagac tatgtcttgc | | | 780 |
| ctggcccaca tgatgaagcg aaagatcacc atgcccgccc acctgatgcg agatggccga | | | 840 |
| gatccccacc tgttccagca cttctctgtg gtggcctccc gaaccggcgt gtacaccgtg | | | 900 |
| atggactaca tcaacatcct cgagcacttc gtcgagaagt ggaacatcga agatcacc | | | 960 |
| gccggactgt ctgacaaggg ccgagaggcc caggactacg tgtgcaagct gggcgagcga | | | 1020 |
| ctgcgaaagg tcgaggagcg agctcatcag cgagtggtgc aggccgaccc catccccttc | | | 1080 |
| tcttggatct cgaccgaaa ggtgtaa | | | 1107 |

<210> SEQ ID NO 2
<211> LENGTH: 368
<212> TYPE: PRT
<213> ORGANISM: Pelargonium x hortorum

<400> SEQUENCE: 2

```
Met Gly Val Leu Leu Asn Ile Cys Ser Ser Pro Phe Pro Val Val Ala
1               5                   10                  15

Ser Ala Ser Thr Ser Ile Ser Lys Val Asn His Ile Arg Lys Val
            20                  25                  30

Gly Val Thr Gly Val Met Ala Pro Gln Lys Ile Glu Ile Phe Lys Ser
        35                  40                  45

Met Glu Glu Trp Gly Lys His Asn Ile Leu Pro Leu Ala Lys Pro Val
    50                  55                  60

Glu Lys Ser Trp Gln Pro Thr Asp Phe Leu Pro Asp Pro Ser Ser Glu
65                  70                  75                  80

Gly Phe Met Glu Glu Tyr Asn Ala Phe Lys Glu Arg Thr Arg Glu Leu
                85                  90                  95

Pro Asp Glu Tyr Phe Val Val Leu Ala Gly Asp Met Ile Thr Glu Glu
            100                 105                 110

Ala Leu Pro Thr Tyr Gln Thr Leu Val Asn Arg Pro Asp Glu Val Ala
        115                 120                 125

Asp Glu Thr Gly His Ser Glu Ser Pro Trp Ala Val Trp Ser Arg Ala
    130                 135                 140

Trp Thr Ala Glu Glu Asn Arg His Gly Asp Leu Leu Asn Lys Tyr Leu
145                 150                 155                 160

Tyr Leu Ser Gly Lys Leu Asp Met Arg Gln Val Glu Lys Thr Ile Gln
                165                 170                 175

Tyr Leu Ile Ala Leu Gly Gln Asp Ile Gly Thr Glu Lys Asn Pro Tyr
            180                 185                 190

His Leu Phe Ile Tyr Thr Ser Phe Gln Glu Arg Ala Thr Phe Ile Ser
        195                 200                 205

His Ala Asn Thr Ala Lys Leu Ala Gln Gln His Gly Asp Lys Gln Leu
    210                 215                 220
```

Ala Gln Ile Cys Gly Thr Ile Ala Ala Asp Glu Lys Arg His Glu Thr
225                 230                 235                 240

Ala Tyr Thr Arg Ile Val Asp Lys Leu Phe Glu Leu Asp Pro Asp Glu
            245                 250                 255

Thr Met Ser Cys Leu Ala His Met Met Lys Arg Lys Ile Thr Met Pro
        260                 265                 270

Ala His Leu Met Arg Asp Gly Arg Asp Pro His Leu Phe Gln His Phe
    275                 280                 285

Ser Val Val Ala Ser Arg Thr Gly Val Tyr Thr Val Met Asp Tyr Ile
290                 295                 300

Asn Ile Leu Glu His Phe Val Glu Lys Trp Asn Ile Glu Lys Ile Thr
305                 310                 315                 320

Ala Gly Leu Ser Asp Lys Gly Arg Glu Ala Gln Asp Tyr Val Cys Lys
            325                 330                 335

Leu Gly Glu Arg Leu Arg Lys Val Glu Glu Arg Ala His Gln Arg Val
        340                 345                 350

Val Gln Ala Asp Pro Ile Pro Phe Ser Trp Ile Phe Asp Arg Lys Val
    355                 360                 365

<210> SEQ ID NO 3
<211> LENGTH: 1191
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1191)
<223> OTHER INFORMATION: Y.lipolytica codon-optimized nucleotide
      sequence of delta9 desaturase from Ricinus communis

<400> SEQUENCE: 3
atggccctga agctgaaccc cttcctgtct caaacccaga gctgccctc tttcgccctg        60 cctcccatgg cctctacccg atctcccaag ttctacatgg cctccaccct gaagtctggc      120
tctaaggagg tcgagaacct gaagaagccc ttcatgcctc ccgagaggt gcacgtgcag       180 gtcaccccact ctatgcctcc ccagaagatc gagatcttca gtctctgga caactgggcc      240 gaggagaaca tcctggtcca cctgaagccc gtcgagaagt gctggcagcc ccaggacttc      300
ctgcccgacc ccgcctctga cggcttcgac gagcaggtcc gagagctgcg agagcgagcc      360
aaggagatcc ccgacgacta cttcgtggtg ctggtgggcg acatgatcac cgaggaggcc      420
ctgcccacct accagaccgc cctgaaccga ggcgacggcg tgcgagatga actggcgcc       480 tctcccacct cttgggccat ctggacccga gcctggaccg ctgaggagaa ccgacacggc      540
gacctgctga caagtacct gtacctgtct ggccgagtgg acatgcgaca gatcgagaag       600
accatccagt acctgatcgg ctctggcatg gacgtgcgag tcgagaactc tccctacctg      660
ctgttcatct acacctcgtt ccaggagcga gccaccttca tctctcacgg caacaccgcc      720
cgacaggcca aggagcacgg cgacatcaag ctggcccaga tctgcggcac cattgccgcc      780
gacgagaagc gacacgagac tgcctacacc aagatcgtcg agaagctgtt cgagatcgac      840
cccgacggca ccgtgctggc cttcgccgac atgatgcgaa agaagatctc tatgcccgcc      900
cacctgatgt acgacggccg agatgacaac ctgttcgacc acttctctgc cgtggctcag      960
cgactgggcg tgtacaccgc caaggactac gccgacatcc tcgagtttct ggtgggcgga     1020
tggaaggtgg acaagctgac cggcctgtct gccgagggcc agaaggccca ggactacgtc     1080
tgccgactgc ctccccgaat ccgacgactc gaggagcgag ctcagggccg agctaaggag     1140
gctcccacca tgcccttctc ttggatcttc gaccgacagg tgaagctgta a   1191

```
<210> SEQ ID NO 4
<211> LENGTH: 396
<212> TYPE: PRT
<213> ORGANISM: Ricinus communis

<400> SEQUENCE: 4
```

Met Ala Leu Lys Leu Asn Pro Phe Leu Ser Gln Thr Gln Lys Leu Pro
1               5                   10                  15

Ser Phe Ala Leu Pro Pro Met Ala Ser Thr Arg Ser Pro Lys Phe Tyr
            20                  25                  30

Met Ala Ser Thr Leu Lys Ser Gly Ser Lys Glu Val Glu Asn Leu Lys
        35                  40                  45

Lys Pro Phe Met Pro Pro Arg Glu Val His Val Gln Val Thr His Ser
50                  55                  60

Met Pro Pro Gln Lys Ile Glu Ile Phe Lys Ser Leu Asp Asn Trp Ala
65                  70                  75                  80

Glu Glu Asn Ile Leu Val His Leu Lys Pro Val Glu Lys Cys Trp Gln
                85                  90                  95

Pro Gln Asp Phe Leu Pro Asp Pro Ala Ser Asp Gly Phe Asp Glu Gln
            100                 105                 110

Val Arg Glu Leu Arg Glu Arg Ala Lys Glu Ile Pro Asp Asp Tyr Phe
        115                 120                 125

Val Val Leu Val Gly Asp Met Ile Thr Glu Glu Ala Leu Pro Thr Tyr
130                 135                 140

Gln Thr Ala Leu Asn Arg Gly Asp Gly Val Arg Asp Glu Thr Gly Ala
145                 150                 155                 160

Ser Pro Thr Ser Trp Ala Ile Trp Thr Arg Ala Trp Thr Ala Glu Glu
                165                 170                 175

Asn Arg His Gly Asp Leu Leu Asn Lys Tyr Leu Tyr Leu Ser Gly Arg
            180                 185                 190

Val Asp Met Arg Gln Ile Glu Lys Thr Ile Gln Tyr Leu Ile Gly Ser
        195                 200                 205

Gly Met Asp Val Arg Val Glu Asn Ser Pro Tyr Leu Leu Phe Ile Tyr
210                 215                 220

Thr Ser Phe Gln Glu Arg Ala Thr Phe Ile Ser His Gly Asn Thr Ala
225                 230                 235                 240

Arg Gln Ala Lys Glu His Gly Asp Ile Lys Leu Ala Gln Ile Cys Gly
                245                 250                 255

Thr Ile Ala Ala Asp Glu Lys Arg His Glu Thr Ala Tyr Thr Lys Ile
            260                 265                 270

Val Glu Lys Leu Phe Glu Ile Asp Pro Asp Gly Thr Val Leu Ala Phe
        275                 280                 285

Ala Asp Met Met Arg Lys Lys Ile Ser Met Pro Ala His Leu Met Tyr
290                 295                 300

Asp Gly Arg Asp Asp Asn Leu Phe Asp His Phe Ser Ala Val Ala Gln
305                 310                 315                 320

Arg Leu Gly Val Tyr Thr Ala Lys Asp Tyr Ala Asp Ile Leu Glu Phe
                325                 330                 335

Leu Val Gly Arg Trp Lys Val Asp Lys Leu Thr Gly Leu Ser Ala Glu
            340                 345                 350

Gly Gln Lys Ala Gln Asp Tyr Val Cys Arg Leu Pro Pro Arg Ile Arg
        355                 360                 365

Arg Leu Glu Glu Arg Ala Gln Gly Arg Ala Lys Glu Ala Pro Thr Met
        370                 375                 380

Pro Phe Ser Trp Ile Phe Asp Arg Gln Val Lys Leu
385                 390                 395

<210> SEQ ID NO 5
<211> LENGTH: 1059
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1059)
<223> OTHER INFORMATION: S. cerevisiae codon-optimized nucleotide
      sequence of delta9 desaturase from Amyelois transitella Atr236

<400> SEQUENCE: 5
atgccgcctc agggtcaaga tcgcgagtcc tgggttctgt acgagaccga cgacaagacg     60
caagatggtg gcactcacgt ggtgcctccc tccgccgaga aaagagtgtg gaaaatcgtc    120
tggaggaatg tcatcgcatt tgctctgctc cacatcggag gcgtttacgg cgcttatttg    180
ttcctcttca agctatgtg gctgaccgat ttgtttgcgg tatttctgta cctgtgctcc    240
ggcctgggcg tcactgcggg cgcgcaccgg ctgtgggcac acaagtcgta caaggcgcgg    300
ctgcctctcc gcctgttgct tactgtcttc aacaccatag cttttcagga tgccgtgatc    360
gactgggctc gcgaccaccg cctgcaccat aagtactcgg agacggacgc cgatccccac    420
aacgcaacaa gggggttctt cttctcccac attggctggt tgctcgtcag gaaacaccca    480
caaatcaagg agaaagggcc caccatcgac ctgaacgact tgagggccga tcccgtactc    540
cacttccaga gaaatactat tttataccttt atgcccttgg catgtttcgt catgcccaca    600
ttagtaccta cactctgggg tgaatctcta tggaacgcgt atttcgtatg cgctatcttc    660
agatacatat atgttctaaa cgtcacttgg ctcgtaaact cagctgcgca cgcttgggga    720
agcaaaccgt acgacaaaaa catcaaccct gtggaaacca gcctgtatc cttggtggtc    780 cttggagaag gcttccacaa ttaccaccac actttcccgt gggattacaa gactgccgaa    840
ttaggagatt actctttaaa cttctccaaa ttattcatcg atgctatggc aaaaataggt    900
tgggcttatg acctgaaaac ggtctctcct gatgtgatcg agaagcgtgt gaagaggacg    960
ggagacggca gtcaccacgt ctggggctgg acgacaaag acgtcccggt tgaagaaaaa   1020
gaagaagcca ccatctttaa cccttcgaaa gatgaataa                         1059

<210> SEQ ID NO 6
<211> LENGTH: 352
<212> TYPE: PRT
<213> ORGANISM: Amyelois transitella

<400> SEQUENCE: 6

Met Pro Pro Gln Gly Gln Asp Arg Glu Ser Trp Val Leu Tyr Glu Thr
1               5                   10                  15

Asp Asp Lys Thr Gln Asp Gly Gly Thr His Val Val Pro Pro Ser Ala
            20                  25                  30

Glu Lys Arg Val Trp Lys Ile Val Trp Arg Asn Val Ile Ala Phe Ala
        35                  40                  45

Leu Leu His Ile Gly Gly Val Tyr Gly Ala Tyr Leu Phe Leu Phe Lys
    50                  55                  60

Ala Met Trp Leu Thr Asp Leu Phe Ala Val Phe Leu Tyr Leu Cys Ser

```
                65                  70                  75                  80
        Gly Leu Gly Val Thr Ala Gly Ala His Arg Leu Trp Ala His Lys Ser
                            85                  90                  95

Tyr Lys Ala Arg Leu Pro Leu Arg Leu Leu Thr Val Phe Asn Thr
                        100                 105                 110

Ile Ala Phe Gln Asp Ala Val Ile Asp Trp Ala Arg Asp His Arg Leu
                    115                 120                 125

His His Lys Tyr Ser Glu Thr Asp Ala Asp Pro His Asn Ala Thr Arg
                130                 135                 140

Gly Phe Phe Phe Ser His Ile Gly Trp Leu Leu Val Arg Lys His Pro
        145                 150                 155                 160

Gln Ile Lys Glu Lys Gly Pro Thr Ile Asp Leu Asn Asp Leu Arg Ala
                        165                 170                 175

Asp Pro Val Leu His Phe Gln Lys Lys Tyr Tyr Leu Tyr Leu Met Pro
                    180                 185                 190

Leu Ala Cys Phe Val Met Pro Thr Leu Val Pro Thr Leu Trp Gly Glu
                195                 200                 205

Ser Leu Trp Asn Ala Tyr Phe Val Cys Ala Ile Phe Arg Tyr Ile Tyr
            210                 215                 220

Val Leu Asn Val Thr Trp Leu Val Asn Ser Ala Ala His Ala Trp Gly
        225                 230                 235                 240

Ser Lys Pro Tyr Asp Lys Asn Ile Asn Pro Val Glu Thr Lys Pro Val
                        245                 250                 255

Ser Leu Val Val Leu Gly Glu Gly Phe His Asn Tyr His His Thr Phe
                    260                 265                 270

Pro Trp Asp Tyr Lys Thr Ala Glu Leu Gly Asp Tyr Ser Leu Asn Phe
                275                 280                 285

Ser Lys Leu Phe Ile Asp Ala Met Ala Lys Ile Gly Trp Ala Tyr Asp
            290                 295                 300

Leu Lys Thr Val Ser Pro Asp Val Ile Glu Lys Arg Val Lys Arg Thr
        305                 310                 315                 320

Gly Asp Gly Ser His His Val Trp Gly Trp Asp Asp Lys Asp Val Pro
                        325                 330                 335

Val Glu Glu Lys Glu Glu Ala Thr Ile Phe Asn Pro Ser Lys Asp Glu
                    340                 345                 350

<210> SEQ ID NO 7
<211> LENGTH: 1059
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1059)
<223> OTHER INFORMATION: S. cerevisiae codon-optimized nucleotide
      sequence of delta9 desaturase from Amyelois transitella Atr1432

<400> SEQUENCE: 7
atggctccaa atgccacaga tgctaatggg gttctgtttg agacggatgc agctacccca      60
gacctggccc tacctcacgc ccctgtacag caagcggaca attaccctaa aaaatatgtg     120
tggagaaata taatattatt tgcctatctc cacattgctg cactctatgg tggctacttg     180
ttcttgttcc atgctaaatg gcagacagat atatttgctt acattctgta tgtgatgtca     240
ggcttgggaa taacggcagg agcccatcgt ctgtgggccc acaagtccta caaagctaaa     300
tggccactca gattgatact tgtcatcttt aacactctgg cattccagga ctctgcaatc     360
```

```
gactggtctc gcgaccaccg aatgcaccac aaatactcgg aaactgatgc tgatccccac    420
aacgcgaccc gcggtttctt cttctcccac attggctggc tgctggttag aagcaccct    480 gaacttaaga ggaaaggcaa aggtctggac cttagtgact tatatgctga ccccatttg    540 agattccaaa agaagtacta cttgatcctg atgcccctca cttgcttcgt gttacctacg    600
gtcatccccg tgtattactg gggcgagact tggaccaacg ccttcttcgt ggccgctctt    660
ttccggtatg ccttcatcct taacgtcacc tggctggtca attctgctgc tcacaagtgg    720
ggcgataagc ttacgatag aaacatcaag ccttcggaaa atatttccgt ctccatgttc    780
gcgctcggag aaggcttcca caactaccac atactttcc cctgggacta caagaccgcg    840
gaacttggca caacatgct caatttcacg actaacttca tcaatttctt tgctaaaatc    900
ggttgggcgt acgatctgaa aactgtttcc gatgaaattg ttaggagccg cgctaagaga    960
acaggagatg gttctcacca tctatggggc tggggtgata aggatcactc tcgtgaggaa   1020
atggccgccg ctataaggat acacccgaaa gatgactag                          1059
```

<210> SEQ ID NO 8
<211> LENGTH: 352
<212> TYPE: PRT
<213> ORGANISM: Amyelois transitella

<400> SEQUENCE: 8

```
Met Ala Pro Asn Ala Thr Asp Ala Asn Gly Val Leu Phe Glu Thr Asp
1               5                   10                  15

Ala Ala Thr Pro Asp Leu Ala Leu Pro His Ala Pro Val Gln Gln Ala
            20                  25                  30

Asp Asn Tyr Pro Lys Lys Tyr Val Trp Arg Asn Ile Ile Leu Phe Ala
        35                  40                  45

Tyr Leu His Ile Ala Ala Leu Tyr Gly Gly Tyr Leu Phe Leu Phe His
    50                  55                  60

Ala Lys Trp Gln Thr Asp Ile Phe Ala Tyr Ile Leu Tyr Val Met Ser
65                  70                  75                  80

Gly Leu Gly Ile Thr Ala Gly Ala His Arg Leu Trp Ala His Lys Ser
                85                  90                  95

Tyr Lys Ala Lys Trp Pro Leu Arg Leu Ile Leu Val Ile Phe Asn Thr
            100                 105                 110

Leu Ala Phe Gln Asp Ser Ala Ile Asp Trp Ser Arg Asp His Arg Met
        115                 120                 125

His His Lys Tyr Ser Glu Thr Asp Ala Asp Pro His Asn Ala Thr Arg
    130                 135                 140

Gly Phe Phe Phe Ser His Ile Gly Trp Leu Leu Val Arg Lys His Pro
145                 150                 155                 160

Glu Leu Lys Arg Lys Gly Lys Gly Leu Asp Leu Ser Asp Leu Tyr Ala
                165                 170                 175

Asp Pro Ile Leu Arg Phe Gln Lys Lys Tyr Tyr Leu Ile Leu Met Pro
            180                 185                 190

Leu Thr Cys Phe Val Leu Pro Thr Val Ile Pro Val Tyr Tyr Trp Gly
        195                 200                 205

Glu Thr Trp Thr Asn Ala Phe Phe Val Ala Ala Leu Phe Arg Tyr Ala
    210                 215                 220

Phe Ile Leu Asn Val Thr Trp Leu Val Asn Ser Ala Ala His Lys Trp
225                 230                 235                 240

Gly Asp Lys Pro Tyr Asp Arg Asn Ile Lys Pro Ser Glu Asn Ile Ser
```

```
                    245                 250                 255
Val Ser Met Phe Ala Leu Gly Glu Gly Phe His Asn Tyr His His Thr
            260                 265                 270

Phe Pro Trp Asp Tyr Lys Thr Ala Glu Leu Gly Asn Asn Met Leu Asn
            275                 280                 285

Phe Thr Thr Asn Phe Ile Asn Phe Phe Ala Lys Ile Gly Trp Ala Tyr
        290                 295                 300

Asp Leu Lys Thr Val Ser Asp Glu Ile Val Arg Ser Arg Ala Lys Arg
305                 310                 315                 320

Thr Gly Asp Gly Ser His His Leu Trp Gly Trp Gly Asp Lys Asp His
                325                 330                 335

Ser Arg Glu Glu Met Ala Ala Ala Ile Arg Ile His Pro Lys Asp Asp
            340                 345                 350
```

<210> SEQ ID NO 9
<211> LENGTH: 1086
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1086)
<223> OTHER INFORMATION: S. cerevisiae codon-optimized nucleotide
      sequence of delta9 desaturase from Drosophila melanogaster Dmd9

<400> SEQUENCE: 9

```
atggctccat actctagaat ctaccaccaa gataagtcct ctagagaaac tggtgttttg      60
ttcgaagatg atgctcaaac cgttgattct gatttgacta ccgatagatt ccaattgaag     120
agagccgaaa aagaagatt gccattggtt tggagaaaca tcatcttgtt cgctttggtt     180
catttggctg ccttgtatgg tttacattcc attttcacta gagctaagtt ggctactact     240
ttgtttgctg ctggttttgta cattatcggt atgttgggtg ttactgctgg tgctcataga     300
ttgtgggctc atagaactta caaagctaaa tggcctttga gattgttgtt ggtcatcttc     360
aacaccattg ctttccaaga tgctgtttat cattgggcca gagatcatag agttcatcac     420
aaatactctg aaaccgatgc tgatccacat aatgctacta gaggttttct cttctctcat     480
gttggttggt tgttgtgcaa gaaacaccca gatatcaaag aaaagggtag aggtttggat     540
ttgtccgatt gagagctga tccaatcttg atgtttcaaa gaaagcacta ctacatcttg     600
atgccattgg cttgttttgt tttgccaacc gttattccaa tggtctactg gaacgaaact     660
ttggcttctt cttggtttgt tgctactatg ttcagatggt gcttccaatt gaatatgacc     720
tggttggtta attccgctgc tcataagttt ggtaatagac atacgataa gaccatgaac     780
ccaactcaaa tgctttcgt ttctgctttc acttttggtg aaggttggca taattaccat     840
catgcttttc catgggatta caagactgct gaatggggtt gttactcttt gaacattact     900
accgccttca ttgatttgtt cgctaaaatt ggttgggcct acgatttgaa aactgttgct     960
ccagatgtta tccaaagaag agtttttgaga actggtgatg gttctcatga attgtgggt   1020
tggggtgata aggatttgac cgctgaagat gctagaaacg ttttgttggt tgacaagtcc   1080
agataa                                                              1086
```

<210> SEQ ID NO 10
<211> LENGTH: 361
<212> TYPE: PRT
<213> ORGANISM: Drosophila melanogaster

<400> SEQUENCE: 10

```
Met Ala Pro Tyr Ser Arg Ile Tyr His Gln Asp Lys Ser Ser Arg Glu
1               5                   10                  15

Thr Gly Val Leu Phe Glu Asp Ala Gln Thr Val Asp Ser Asp Leu
            20                  25                  30

Thr Thr Asp Arg Phe Gln Leu Lys Arg Ala Glu Lys Arg Leu Pro
        35                  40                  45

Leu Val Trp Arg Asn Ile Ile Leu Phe Ala Leu Val His Leu Ala Ala
50                  55                  60

Leu Tyr Gly Leu His Ser Ile Phe Thr Arg Ala Lys Leu Ala Thr Thr
65                  70                  75                  80

Leu Phe Ala Ala Gly Leu Tyr Ile Ile Gly Met Leu Gly Val Thr Ala
                85                  90                  95

Gly Ala His Arg Leu Trp Ala His Arg Thr Tyr Lys Ala Lys Trp Pro
            100                 105                 110

Leu Arg Leu Leu Leu Val Ile Phe Asn Thr Ile Ala Phe Gln Asp Ala
        115                 120                 125

Val Tyr His Trp Ala Arg Asp His Arg Val His His Lys Tyr Ser Glu
130                 135                 140

Thr Asp Ala Asp Pro His Asn Ala Thr Arg Gly Phe Phe Phe Ser His
145                 150                 155                 160

Val Gly Trp Leu Leu Cys Lys Lys His Pro Asp Ile Lys Glu Lys Gly
                165                 170                 175

Arg Gly Leu Asp Leu Ser Asp Leu Arg Ala Asp Pro Ile Leu Met Phe
            180                 185                 190

Gln Arg Lys His Tyr Tyr Ile Leu Met Pro Leu Ala Cys Phe Val Leu
        195                 200                 205

Pro Thr Val Ile Pro Met Val Tyr Trp Asn Glu Thr Leu Ala Ser Ser
210                 215                 220

Trp Phe Val Ala Thr Met Phe Arg Trp Cys Phe Gln Leu Asn Met Thr
225                 230                 235                 240

Trp Leu Val Asn Ser Ala Ala His Lys Phe Gly Asn Arg Pro Tyr Asp
                245                 250                 255

Lys Thr Met Asn Pro Thr Gln Asn Ala Phe Val Ser Ala Phe Thr Phe
            260                 265                 270

Gly Glu Gly Trp His Asn Tyr His His Ala Phe Pro Trp Asp Tyr Lys
        275                 280                 285

Thr Ala Glu Trp Gly Cys Tyr Ser Leu Asn Ile Thr Thr Ala Phe Ile
290                 295                 300

Asp Leu Phe Ala Lys Ile Gly Trp Ala Tyr Asp Leu Lys Thr Val Ala
305                 310                 315                 320

Pro Asp Val Ile Gln Arg Val Leu Arg Thr Gly Asp Gly Ser His
                325                 330                 335

Glu Leu Trp Gly Trp Gly Asp Lys Asp Leu Thr Ala Glu Asp Ala Arg
            340                 345                 350

Asn Val Leu Leu Val Asp Lys Ser Arg
        355                 360
```

<210> SEQ ID NO 11
<211> LENGTH: 1062
<212> TYPE: DNA
<213> ORGANISM: Artificial Sequence
<220> FEATURE:
<223> OTHER INFORMATION: codon-optimized nucleotide sequence
<220> FEATURE:

<221> NAME/KEY: misc_feature
<222> LOCATION: (1)..(1062)
<223> OTHER INFORMATION: Y. lipolytica codon-optimized nucleotide
sequence of delta9 desaturase from Spodoptera litura Des11

<400> SEQUENCE: 11

```
atggctccca acatctctga ggacgtgaac ggcgtgctgt tcgagtctga cgccgctact     60
cccgacctgg ctctggcccg acctcctgtg cagaaggccg acaacaagcc caagcagctg    120
gtgtggcgaa acatcatcct gttcgcctac ctgcacctgg ccgctctgta cggcggctac    180
ctgttcctgt tctctgccaa gtggcagacc gacatcttcg cctacatcct gtacgtgatc    240
tctggcctgg gcatcaccgc tggcgcccac cgactgtggg ctcacaagtc ttacaaggct    300
aagtggcccc tgaaggtgat cctgatcatc ttcaacaccg tggccttcca ggacgccgcc    360
atggactggg cccgagatca ccgaatgcac cacaagtact ctgagactga cgctgaccct    420
cacaacgcta cccgaggctt cttcttctct cacatcggct ggctgctggt gcgaaagcac    480
cccgacctga aggaaaaggg caagggcctc gacatgtctg acctgctggc tgaccccgtg    540
ctgcgattcc agaagaagta ctacctgctg ctgatgcccc tggcctgctt cgtcatgccc    600
accgtgattc ccgtgtacct gtggggcgag acttggacca acgccttctt cgtggccgcc    660
atgttccgat acgccttcat tctgaacgtg acctggctgg tgaactctgc tgcccacaag    720
tggggcgaca agccctacga caagtctatc aagccctctg agaacatgtc tgtggccatg    780
ttcgccctcg gcgagggatt ccacaactac caccacacat tcccttggga ctacaagacc    840
gccgagttcg gcaacaacaa gctgaacttc actaccgcct tcatcaactt tttcgccaag    900
atcggctggg cttacgacat gaagaccgtg tctgaggaca tcgtgaagaa ccgagtgaag    960
cgaaccggcg acggctctca ccacctctgg ggctggggcg acgagaacca gcctaaggaa   1020
gagatcgagg ccgccatccg aatcaacccc aaggacgact aa                      1062
```

<210> SEQ ID NO 12
<211> LENGTH: 353
<212> TYPE: PRT
<213> ORGANISM: Spodoptera litura

<400> SEQUENCE: 12

```
Met Ala Pro Asn Ile Ser Glu Asp Val Asn Gly Val Leu Phe Glu Ser
1               5                   10                  15

Asp Ala Ala Thr Pro Asp Leu Ala Leu Ala Arg Pro Pro Val Gln Lys
            20                  25                  30

Ala Asp Asn Lys Pro Lys Gln Leu Val Trp Arg Asn Ile Ile Leu Phe
        35                  40                  45

Ala Tyr Leu His Leu Ala Ala Leu Tyr Gly Gly Tyr Leu Phe Leu Phe
    50                  55                  60

Ser Ala Lys Trp Gln Thr Asp Ile Phe Ala Tyr Ile Leu Tyr Val Ile
65                  70                  75                  80

Ser Gly Leu Gly Ile Thr Ala Gly Ala His Arg Leu Trp Ala His Lys
                85                  90                  95

Ser Tyr Lys Ala Lys Trp Pro Leu Lys Val Ile Leu Ile Ile Phe Asn
            100                 105                 110

Thr Val Ala Phe Gln Asp Ala Ala Met Asp Trp Ala Arg Asp His Arg
        115                 120                 125

Met His His Lys Tyr Ser Glu Thr Asp Ala Asp Pro His Asn Ala Thr
    130                 135                 140

Arg Gly Phe Phe Phe Ser His Ile Gly Trp Leu Leu Val Arg Lys His
```

Pro Asp Leu Lys Glu Lys Gly Lys Gly Leu Asp Met Ser Asp Leu Leu
               165                 170                 175

Ala Asp Pro Val Leu Arg Phe Gln Lys Lys Tyr Tyr Leu Leu Leu Met
           180                 185                 190

Pro Leu Ala Cys Phe Val Met Pro Thr Val Ile Pro Val Tyr Leu Trp
       195                 200                 205

Gly Glu Thr Trp Thr Asn Ala Phe Phe Val Ala Ala Met Phe Arg Tyr
   210                 215                 220

Ala Phe Ile Leu Asn Val Thr Trp Leu Val Asn Ser Ala Ala His Lys
225                 230                 235                 240

Trp Gly Asp Lys Pro Tyr Asp Lys Ser Ile Lys Pro Ser Glu Asn Met
               245                 250                 255

Ser Val Ala Met Phe Ala Leu Gly Glu Gly Phe His Asn Tyr His His
           260                 265                 270

Thr Phe Pro Trp Asp Tyr Lys Thr Ala Glu Phe Gly Asn Asn Lys Leu
       275                 280                 285

Asn Phe Thr Thr Ala Phe Ile Asn Phe Phe Ala Lys Ile Gly Trp Ala
   290                 295                 300

Tyr Asp Met Lys Thr Val Ser Glu Asp Ile Val Lys Asn Arg Val Lys
305                 310                 315                 320

Arg Thr Gly Asp Gly Ser His His Leu Trp Gly Trp Gly Asp Glu Asn
               325                 330                 335

Gln Pro Lys Glu Glu Ile Glu Ala Ala Ile Arg Ile Asn Pro Lys Asp
               340                 345                 350

Asp

<210> SEQ ID NO 13
<211> LENGTH: 1050
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1050)
<223> OTHER INFORMATION: Y.lipolytica codon-optimized nucleotide
      sequence of delta 9 desaturase from Chauliognathus lugubris Cld9

<400> SEQUENCE: 13

```
atggctccca actctaacga cgccaccggc gtgctgcaag agactgacga cgacgtgtcc      60
tctaaccagg tcctgcagca gatcaccaag tctgagaagt ctaagctgat catcgtgtgg     120
tctaacgtga tgtacttcgt gatcctgcac gtgggcgccc tgtacggcct gtggctgctg     180
ctgacctctg tcagatctg gacctgcctg tgggtgttcg ccatgtacga gttcggcgag     240
atctgcatca ccgctggcgt gcaccgactg tggtcccacc gatcttacaa ggccaagtgg     300
cccctgcgac tgttccacac catgggacag acctggcct tccagacgc cgtggtggac      360 tgggcccgag atcaccgagt gcaccacaag tactctgaaa ccgacgctga ccctcacaac    420
gccaagcgag gcttcttctt ctctcacatg ggctggctga tgtgccgaaa gtccaagcag    480
gtcaaggaaa agggcaagga acccgacatc tctgacctgt acgctgatcc atcctgcga    540 taccaaaaga gtactacat gctgttcatg cccctgatgt gcttcgcttt ccccaccgtg    600 gtgccctgt acttctggaa cgagtctctc aagaccgcct tcttcgtgaa catcttccgg    660
tacatcttct ccctgcacgc cacctggctg gtgaactctg ccgctcacct ctacggcgag    720
```

```
aagccctaca acaagcacat taaccccgcc gagaacctgg ccgtgtctct gatcgtgaac    780
ggcgaacgat ggcacaacta ccaccacaca ttcccttggg actacaaggc cggcgagttc    840
ggacgatacg gcaccaacct gaccaccgtg ttcatcaacg ccatggccaa gatcggcctg    900
gcctacgacc tgaagttcgt gcccgaggac gtggtgaagc gacgagtgca caagaccggc    960
gacggctctc acgccgtgtg gggctggggc gacaaggacc agaccgtgga agagatttct   1020
aagaccatcg tggcctacaa ccagtcttaa                                    1050
```

<210> SEQ ID NO 14
<211> LENGTH: 349
<212> TYPE: PRT
<213> ORGANISM: Chauliognathus lugubris

<400> SEQUENCE: 14

```
Met Ala Pro Asn Ser Asn Asp Ala Thr Gly Val Leu Gln Glu Thr Asp
1               5                   10                  15

Asp Asp Val Ser Ser Asn Gln Val Leu Gln Gln Ile Thr Lys Ser Glu
            20                  25                  30

Lys Ser Lys Leu Ile Ile Val Trp Ser Asn Val Met Tyr Phe Val Ile
        35                  40                  45

Leu His Val Gly Ala Leu Tyr Gly Leu Trp Leu Leu Leu Thr Ser Ala
    50                  55                  60

Gln Ile Trp Thr Cys Leu Trp Val Phe Ala Met Tyr Glu Phe Gly Glu
65                  70                  75                  80

Ile Cys Ile Thr Ala Gly Val His Arg Leu Trp Ser His Arg Ser Tyr
                85                  90                  95

Lys Ala Lys Trp Pro Leu Arg Leu Phe His Thr Met Gly Gln Thr Leu
            100                 105                 110

Ala Phe Gln Asp Ala Val Val Asp Trp Ala Arg Asp His Arg Val His
        115                 120                 125

His Lys Tyr Ser Glu Thr Asp Ala Asp Pro His Asn Ala Lys Arg Gly
    130                 135                 140

Phe Phe Phe Ser His Met Gly Trp Leu Met Cys Arg Lys Ser Lys Gln
145                 150                 155                 160

Val Lys Glu Lys Gly Lys Glu Pro Asp Ile Ser Asp Leu Tyr Ala Asp
                165                 170                 175

Pro Ile Leu Arg Tyr Gln Lys Lys Tyr Tyr Met Leu Phe Met Pro Leu
            180                 185                 190

Met Cys Phe Ala Phe Pro Thr Val Val Pro Leu Tyr Phe Trp Asn Glu
        195                 200                 205

Ser Leu Lys Thr Ala Phe Phe Val Asn Ile Phe Arg Tyr Ile Phe Ser
    210                 215                 220

Leu His Ala Thr Trp Leu Val Asn Ser Ala Ala His Leu Tyr Gly Glu
225                 230                 235                 240

Lys Pro Tyr Asn Lys His Ile Asn Pro Ala Glu Asn Leu Ala Val Ser
                245                 250                 255

Leu Ile Val Asn Gly Glu Arg Trp His Asn Tyr His His Thr Phe Pro
            260                 265                 270

Trp Asp Tyr Lys Ala Gly Glu Phe Gly Arg Tyr Gly Thr Asn Leu Thr
        275                 280                 285

Thr Val Phe Ile Asn Ala Met Ala Lys Ile Gly Leu Ala Tyr Asp Leu
    290                 295                 300

Lys Phe Val Pro Glu Asp Val Val Lys Arg Arg Val His Lys Thr Gly
305                 310                 315                 320
```

Asp Gly Ser His Ala Val Trp Gly Trp Gly Asp Lys Asp Gln Thr Val
            325                 330                 335

Glu Glu Ile Ser Lys Thr Ile Val Ala Tyr Asn Gln Ser
            340                 345

<210> SEQ ID NO 15
<211> LENGTH: 909
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(909)
<223> OTHER INFORMATION: Y. lipolytica codon-optimized nucleotide
      sequence of desaturase from Tribolium castaneum D6

<400> SEQUENCE: 15
atgttcctgc gaaccatcac ctctaagttc tactctgacc agatcgtgtg gcgaaacgtg      60
ttcctgctgc tgatcctgca catcatctcc ctgcaaggct ggtacttcgt gctgaccacc     120
accaactggc ccactctgat ctacggcttc atcttcggcg ccctgaccgg ccagggaatc     180
aagctgggag cccaccgact gtgggctcac cgatgctaca aggccaagct gcccctgcga     240
atcttcctgt gcttcctgca gaccgtgact ctgcagaacc ctctgtacga gtgggtgcga     300
gatcaccagg tgcaccacaa gtacaccgac accaacgctg accctctgaa cgctacccga     360
ggcttcttct tctctcacat gggctggctg ctggtgcgaa agcaccccaa cgtgatcgcc     420
aagggcaaga ccctggacct gtctgacctg aagaggacc ccgtggtgat gttccagaag     480
aagtactaca agatcattgc ccctgtgctg accctggcta tccccgctct gatcccctgg     540
tactttttcg gcgaggacct gtacctgtct tgggtgacca cctgtgtgct gccctacttc     600
atcaccctgc actctacctg ggccgtgaac tctgtggccc acatctgggg caccaagcct     660
tacaacaaga cattctgcc caccgagaac attgccgtgg ccattgtggc ctacggcgaa     720
ggctggcaca ctaccacca cgtgttccct tgggactaca aggctgccga gctgggcaac     780
taccgaccta acctgtctac cgccttcatc gacttcatgg ccaagatcgc ctgggcctac     840
gacctgaagt ctgtgtctcc cgagatgctg cgaaagcgaa agatgcgaac cggcgactgc     900
gactactaa                                                              909

<210> SEQ ID NO 16
<211> LENGTH: 302
<212> TYPE: PRT
<213> ORGANISM: Tribolium castaneum

<400> SEQUENCE: 16

Met Phe Leu Arg Thr Ile Thr Ser Lys Phe Tyr Ser Asp Gln Ile Val
1               5                   10                  15

Trp Arg Asn Val Phe Leu Leu Leu Ile Leu His Ile Ile Ser Leu Gln
            20                  25                  30

Gly Trp Tyr Phe Val Leu Thr Thr Thr Asn Trp Pro Thr Leu Ile Tyr
        35                  40                  45

Gly Phe Ile Phe Gly Ala Leu Thr Gly Gln Gly Ile Lys Leu Gly Ala
    50                  55                  60

His Arg Leu Trp Ala His Arg Cys Tyr Lys Ala Lys Leu Pro Leu Arg
65                  70                  75                  80

Ile Phe Leu Cys Phe Leu Gln Thr Val Thr Leu Gln Asn Pro Leu Tyr
                85                  90                  95

Glu Trp Val Arg Asp His Gln Val His His Lys Tyr Thr Asp Thr Asn
            100                 105                 110

Ala Asp Pro Leu Asn Ala Thr Arg Gly Phe Phe Ser His Met Gly
            115                 120                 125

Trp Leu Leu Val Arg Lys His Pro Asn Val Ile Ala Lys Gly Lys Thr
130                 135                 140

Leu Asp Leu Ser Asp Leu Glu Glu Asp Pro Val Val Met Phe Gln Lys
145                 150                 155                 160

Lys Tyr Tyr Lys Ile Ile Ala Pro Val Leu Thr Leu Ala Ile Pro Ala
                165                 170                 175

Leu Ile Pro Trp Tyr Phe Phe Gly Glu Asp Leu Tyr Leu Ser Trp Val
            180                 185                 190

Thr Thr Cys Val Leu Pro Tyr Phe Ile Thr Leu His Ser Thr Trp Ala
            195                 200                 205

Val Asn Ser Val Ala His Ile Trp Gly Thr Lys Pro Tyr Asn Lys Asn
210                 215                 220

Ile Leu Pro Thr Glu Asn Ile Ala Val Ala Ile Val Ala Tyr Gly Glu
225                 230                 235                 240

Gly Trp His Asn Tyr His His Val Phe Pro Trp Asp Tyr Lys Ala Ala
                245                 250                 255

Glu Leu Gly Asn Tyr Arg Pro Asn Leu Ser Thr Ala Phe Ile Asp Phe
            260                 265                 270

Met Ala Lys Ile Ala Trp Ala Tyr Asp Leu Lys Ser Val Ser Pro Glu
            275                 280                 285

Met Leu Arg Lys Arg Lys Met Arg Thr Gly Asp Cys Asp Tyr
            290                 295                 300

<210> SEQ ID NO 17
<211> LENGTH: 1170
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1170)
<223> OTHER INFORMATION: Y. lipolytica codon-optimized nucleotide
      sequence of desaturase from Tribolium castaneum D8

<400> SEQUENCE: 17
atggctccca acctgctggg caactctacc ctgttcctgg ccagactaa ctctgctgag      60 cccatccaga tcatctctaa gcccggcctg caggacgtgc tgccccaggt gaagccccag     120
atctcttctc gatcttctgt gtctcagtac cgatggcaga tcgtgtggcg aaacgtgctg     180
atcttcatct acctgcacat tgccggcatc tacggcctgt actacgccat tgctcaggcc     240
cagtggaaga ccctgctgtg gggctacctg gtgatcctgg cctctggcat cggcgtgacc     300
gctggcgccc accgactgtg ggctcaccga acctacaagg ccaagctgcc cctgcgaatc     360
tacctggcct tctgccagac cgtggctctg cagaacgaca tctacgagtg ggtgcgagat     420
caccgagtgc accacaagtt caccgacacc gacgctgacc ctcacaactc taaccgaggc     480
ttcttcttct ctcacatggg ctggctgctg gtgaagaagc acaaggacgt tttcgtgaag     540
ggcaagaccg tggacatgtc tgacgtcgag gctgaccccg tggtgcgatt ccagcgaaag     600
tactacatca ttctgacccc tatcctgacc ttcgtgttcc ccgctatcgt gccctggtac     660
ttctggaacg agactcccac cgtgtgcttc tactctgtgg ccatcttccg atatatcctg     720

```
actctgcacg gcacctggct ggtgaactct gccgctcaca tctggggata ccgaccttac    780
gacaagaaca tcaacgccac cgagaacaag tctgtgtcta ttctggcctt cggcgaagga    840
tggcacaact accaccacgt gttcccttgg gactacaagg ctgccgagct gggaaactac    900
cgaatgaact tcaccaccgc ctttctggac ctgatgtcta agatcggcca ggcctacgac    960
ctcaagactg tgtctgtgga catgatcaac aagcgacgaa agcgaaccgg cgacggaacc   1020
ggcctggtgg acgaggaact gctcgagaac gaggacaagc accaccacca tcacgacgac   1080
tctatttggg gctggggcga caaggacatg aagcaggacg acatggacat ggtccaggtg   1140
cacaaccctt ctcgagagaa gttcgactaa                                    1170

<210> SEQ ID NO 18
<211> LENGTH: 389
<212> TYPE: PRT
<213> ORGANISM: Tribolium castaneum

<400> SEQUENCE: 18

Met Ala Pro Asn Leu Leu Gly Asn Ser Thr Leu Phe Leu Ala Glu Thr
1               5                   10                  15

Asn Ser Ala Glu Pro Ile Gln Ile Ile Ser Lys Pro Gly Leu Gln Asp
            20                  25                  30

Val Leu Pro Gln Val Lys Pro Gln Ile Ser Ser Arg Ser Ser Val Ser
        35                  40                  45

Gln Tyr Arg Trp Gln Ile Val Trp Arg Asn Val Leu Ile Phe Ile Tyr
    50                  55                  60

Leu His Ile Ala Gly Ile Tyr Gly Leu Tyr Tyr Ala Ile Ala Gln Ala
65                  70                  75                  80

Gln Trp Lys Thr Leu Leu Trp Gly Tyr Leu Val Ile Leu Ala Ser Gly
                85                  90                  95

Ile Gly Val Thr Ala Gly Ala His Arg Leu Trp Ala His Arg Thr Tyr
            100                 105                 110

Lys Ala Lys Leu Pro Leu Arg Ile Tyr Leu Ala Phe Cys Gln Thr Val
        115                 120                 125

Ala Leu Gln Asn Asp Ile Tyr Glu Trp Val Arg Asp His Arg Val His
    130                 135                 140

His Lys Phe Thr Asp Thr Asp Ala Asp Pro His Asn Ser Asn Arg Gly
145                 150                 155                 160

Phe Phe Phe Ser His Met Gly Trp Leu Leu Val Lys Lys His Lys Asp
                165                 170                 175

Val Phe Val Lys Gly Lys Thr Val Asp Met Ser Asp Val Glu Ala Asp
            180                 185                 190

Pro Val Val Arg Phe Gln Arg Lys Tyr Tyr Ile Ile Leu Thr Pro Ile
        195                 200                 205

Leu Thr Phe Val Phe Pro Ala Ile Val Pro Trp Tyr Phe Trp Asn Glu
    210                 215                 220

Thr Pro Thr Val Cys Phe Tyr Ser Val Ala Ile Phe Arg Tyr Ile Leu
225                 230                 235                 240

Thr Leu His Gly Thr Trp Leu Val Asn Ser Ala Ala His Ile Trp Gly
                245                 250                 255

Tyr Arg Pro Tyr Asp Lys Asn Ile Asn Ala Thr Glu Asn Lys Ser Val
            260                 265                 270

Ser Ile Leu Ala Phe Gly Glu Gly Trp His Asn Tyr His His Val Phe
        275                 280                 285

Pro Trp Asp Tyr Lys Ala Ala Glu Leu Gly Asn Tyr Arg Met Asn Phe
```

```
                290                 295                 300
Thr Thr Ala Phe Leu Asp Leu Met Ser Lys Ile Gly Gln Ala Tyr Asp
305                 310                 315                 320

Leu Lys Thr Val Ser Val Asp Met Ile Asn Lys Arg Arg Lys Arg Thr
                325                 330                 335

Gly Asp Gly Thr Gly Leu Val Asp Glu Glu Leu Leu Glu Asn Glu Asp
                340                 345                 350

Lys His His His His Asp Asp Ser Ile Trp Gly Trp Gly Asp Lys
                355                 360                 365

Asp Met Lys Gln Asp Asp Met Asp Met Val Gln Val His Asn Pro Ser
                370                 375                 380

Arg Glu Lys Phe Asp
385

<210> SEQ ID NO 19
<211> LENGTH: 1578
<212> TYPE: DNA
<213> ORGANISM: Saccharomyces cerevisiae

<400> SEQUENCE: 19
atgaatgaaa tcgatgagaa aaatcaggcc cccgtgcaac aagaatgcct gaaagagatg      60
attcagaatg ggcatgctcg gcgtatggga tctgttgaag atctgtatgt tgctctcaac     120
agacaaaact tatatcgaaa cttctgcaca tatggagaat tgagtgatta ctgtactagg     180
gatcagctca cattagcttt gagggaaatc tgcctgaaaa atccaactct tttacatatt     240
gttctaccaa caagatggcc aaatcatgaa aattattatc gcagttccga atactattca     300
cggccacatc cagtgcatga ttatatttca gtattacaag aattgaaact gagtggtgtg     360
gttctcaatg aacaacctga gtacagtgca gtaatgaagc aaatattaga agaattcaaa     420
aatagtaagg gttcctatac tgcaaaaatt tttaaactta ctaccacttt gactattcct     480
tactttggac caacaggacc gagttggcgg ctaatttgtc ttccagaaga gcacacagaa     540
aagtggaaaa aatttatctt tgtatctaat cattgcatgt ctgatggtcg gtcttcgatc     600
cacttttttc atgatttaag agacgaatta aataatatta aaactccacc aaaaaaatta     660
gattacattt tcaagtacga ggaggattac caattattga ggaaacttcc agaaccgatc     720
gaaaaggtga tagactttag accaccgtac ttgtttattc cgaagtcact tctttcgggt     780
ttcatctaca atcatttgag attttcttca aaaggtgtct gtatgagaat ggatgatgtg     840
gaaaaaaccg atgatgttgt caccgagatc atcaatattt caccaacaga atttcaagcg     900
attaaagcaa atattaaatc aaatatccaa ggtaagtgta ctatcactcc gtttttacat     960
gtttgttggt ttgtatctct tcataaatgg ggtaaatttt tcaaaccatt gaacttcgaa    1020
tggcttacgg atattttat ccccgcagat tgccgctcac aactaccaga tgatgatgaa    1080
atgagacaga tgtacagata tggcgctaac gttggattta ttgacttcac ccctggata    1140 agcgaatttg acatgaatga taacaaagaa aattttttggc cacttattga gcactaccat    1200
gaagtaattt cggaagcttt aagaaataaa aagcatctcc atggcttagg gttcaatata    1260
caaggcttcg ttcaaaaata tgtgaacatt gacaaggtaa tgtgcgatcg tgccatcggg    1320
aaaagacgcg gaggtacatt gttaagcaat gtaggtctgt ttaatcagtt agaggagccc    1380
gatgccaaat attctatatg cgatttggca tttggccaat tcaaggatc ctggcaccaa    1440 gcattttcct gggtgtttg ttcgactaat gtaaggggga tgaatattgt tgttgcttca    1500
acaaagaatg ttgttggtag tcaagaatct ctcgaagagc tttgctccat ttacaaagct    1560
``` ctcctttag gcccttag                                                                  1578

<210> SEQ ID NO 20
<211> LENGTH: 1578
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1578)
<223> OTHER INFORMATION: Y.lipolytica codon-optimized nucleotide
       sequence of alcohol acetyltransferase from S. cerevisiae ATF1

<400> SEQUENCE: 20

| | | | | |
|---|---|---|---|---|
| atgaacgaga | tcgacgagaa | gaaccaggct | cctgtgcagc | aagagtgcct | gaaggaaatg | 60 |
| atccagaacg | gacacgcccg | acgaatgggc | tctgtcgagg | acctgtacgt | ggccctgaac | 120 |
| cgacagaacc | tgtaccgaaa | cttctgcacc | tacggcgagc | tgtctgacta | ctgcacccga | 180 |
| gatcagctga | ccctggctct | gcagagagatc | tgcctgaaga | accctactct | gctgcatatc | 240 |
| gtgctgccca | ctcgatggcc | caaccacgag | aactactacc | gatcttctga | gtactactct | 300 |
| cgaccccatc | ctgtgcacga | ctacatctcc | gtgctgcaag | agctgaagct | gtctggcgtg | 360 |
| gtgctgaacg | agcagcccga | gtactctgcc | gtgatgaagc | agatcctgga | gagttcaag | 420 |
| aactctaagg | gctcttacac | cgccaagatc | ttcaagctga | ctactaccct | gaccattcct | 480 |
| tacttcggcc | ccactggacc | ctcttggcga | ctgatctgtc | tgcccgagga | acacaccgag | 540 |
| aagtggaaga | agttcatctt | cgtttctaac | cactgcatgt | ctgacggacg | atcctctatc | 600 |
| cacttctttc | acgacctgcg | agatgagctg | aacaacatca | gaccccctcc | aaagaagctg | 660 |
| gactacattt | tcaagtacga | gaggactac | cagctgctgc | gaaagctgcc | cgagcctatc | 720 |
| gagaaggtga | tcgacttccg | acctccttac | ctgttcatcc | caagtctct | gctgtctgga | 780 |
| ttcatctaca | ccacctccg | attctcttcg | aagggcgtgt | gcatgcgaat | ggacgacgtg | 840 |
| gaaaagaccg | acgacgttgt | gaccgagatc | atcaacatct | ctcccaccga | gttccaggcc | 900 |
| atcaaggcca | acattaagtc | taacatccag | ggcaagtgta | ccatcactcc | ctttctgcac | 960 |
| gtgtgctggt | tcgtgtctct | gcacaagtgg | ggcaagttct | ttaagcccct | gaacttcgag | 1020 |
| tggctgaccg | acatcttcat | ccccgccgac | tgccgatctc | agctgcctga | cgacgacgag | 1080 |
| atgcgacaga | tgtaccgata | cggcgccaac | gtgggcttca | tcgacttcac | cccttggatc | 1140 |
| tctgagttcg | acatgaacga | caacaaggaa | aacttctggc | ccctgatcga | gcactaccac | 1200 |
| gaggtgattt | ctgaggccct | gcgaaacaag | aagcacctcc | acggcctggg | cttcaacatt | 1260 |
| cagggcttcg | tccagaagta | cgtcaacatt | gacaaggtga | tgtgcgaccg | agccatcggc | 1320 |
| aagcgacgag | gcggcaccct | gctgtctaac | gtgggcctgt | tcaaccagct | cgaggaaccc | 1380 |
| gacgccaagt | actctatctg | cgacctggcc | ttcggccagt | tccaaggctc | ttggcaccag | 1440 |
| gctttctccc | tgggcgtgtg | ttctaccaac | gtgaagggca | tgaacatcgt | ggtggcctct | 1500 |
| accaagaacg | tggtgggctc | tcaagagtct | ctggaagaac | tgtgctctat | ctacaaggcc | 1560 |
| ctgctgctgg | gcccctaa   |            |            |            |            | 1578 |

<210> SEQ ID NO 21
<211> LENGTH: 525
<212> TYPE: PRT
<213> ORGANISM: Saccharomyces cerevisiae

<400> SEQUENCE: 21

-continued

```
Met Asn Glu Ile Asp Glu Lys Asn Gln Ala Pro Val Gln Gln Glu Cys
1               5                   10                  15

Leu Lys Glu Met Ile Gln Asn Gly His Ala Arg Arg Met Gly Ser Val
            20                  25                  30

Glu Asp Leu Tyr Val Ala Leu Asn Arg Gln Asn Leu Tyr Arg Asn Phe
        35                  40                  45

Cys Thr Tyr Gly Glu Leu Ser Asp Tyr Cys Thr Arg Asp Gln Leu Thr
    50                  55                  60

Leu Ala Leu Arg Glu Ile Cys Leu Lys Asn Pro Thr Leu Leu His Ile
65                  70                  75                  80

Val Leu Pro Thr Arg Trp Pro Asn His Glu Asn Tyr Tyr Arg Ser Ser
                85                  90                  95

Glu Tyr Tyr Ser Arg Pro His Pro Val His Asp Tyr Ile Ser Val Leu
                100                 105                 110

Gln Glu Leu Lys Leu Ser Gly Val Val Leu Asn Glu Gln Pro Glu Tyr
            115                 120                 125

Ser Ala Val Met Lys Gln Ile Leu Glu Glu Phe Lys Asn Ser Lys Gly
        130                 135                 140

Ser Tyr Thr Ala Lys Ile Phe Lys Leu Thr Thr Thr Leu Thr Ile Pro
145                 150                 155                 160

Tyr Phe Gly Pro Thr Gly Pro Ser Trp Arg Leu Ile Cys Leu Pro Glu
                165                 170                 175

Glu His Thr Glu Lys Trp Lys Lys Phe Ile Phe Val Ser Asn His Cys
                180                 185                 190

Met Ser Asp Gly Arg Ser Ser Ile His Phe Phe His Asp Leu Arg Asp
            195                 200                 205

Glu Leu Asn Asn Ile Lys Thr Pro Pro Lys Lys Leu Asp Tyr Ile Phe
210                 215                 220

Lys Tyr Glu Glu Asp Tyr Gln Leu Leu Arg Lys Leu Pro Glu Pro Ile
225                 230                 235                 240

Glu Lys Val Ile Asp Phe Arg Pro Pro Tyr Leu Phe Ile Pro Lys Ser
                245                 250                 255

Leu Leu Ser Gly Phe Ile Tyr Asn His Leu Arg Phe Ser Ser Lys Gly
            260                 265                 270

Val Cys Met Arg Met Asp Asp Val Glu Lys Thr Asp Asp Val Val Thr
        275                 280                 285

Glu Ile Ile Asn Ile Ser Pro Thr Glu Phe Gln Ala Ile Lys Ala Asn
290                 295                 300

Ile Lys Ser Asn Ile Gln Gly Lys Cys Thr Ile Thr Pro Phe Leu His
305                 310                 315                 320

Val Cys Trp Phe Val Ser Leu His Lys Trp Gly Lys Phe Phe Lys Pro
                325                 330                 335

Leu Asn Phe Glu Trp Leu Thr Asp Ile Phe Ile Pro Ala Asp Cys Arg
            340                 345                 350

Ser Gln Leu Pro Asp Asp Asp Glu Met Arg Gln Met Tyr Arg Tyr Gly
        355                 360                 365

Ala Asn Val Gly Phe Ile Asp Phe Thr Pro Trp Ile Ser Glu Phe Asp
370                 375                 380

Met Asn Asp Asn Lys Glu Asn Phe Trp Pro Leu Ile Glu His Tyr His
385                 390                 395                 400

Glu Val Ile Ser Glu Ala Leu Arg Asn Lys Lys His Leu His Gly Leu
                405                 410                 415
```

```
Gly Phe Asn Ile Gln Gly Phe Val Gln Lys Tyr Val Asn Ile Asp Lys
                420                 425                 430

Val Met Cys Asp Arg Ala Ile Gly Lys Arg Arg Gly Gly Thr Leu Leu
            435                 440                 445

Ser Asn Val Gly Leu Phe Asn Gln Leu Glu Glu Pro Asp Ala Lys Tyr
        450                 455                 460

Ser Ile Cys Asp Leu Ala Phe Gly Gln Phe Gln Gly Ser Trp His Gln
465                 470                 475                 480

Ala Phe Ser Leu Gly Val Cys Ser Thr Asn Val Lys Gly Met Asn Ile
                485                 490                 495

Val Val Ala Ser Thr Lys Asn Val Val Gly Ser Gln Glu Ser Leu Glu
            500                 505                 510

Glu Leu Cys Ser Ile Tyr Lys Ala Leu Leu Leu Gly Pro
        515                 520                 525

<210> SEQ ID NO 22
<211> LENGTH: 1236
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1236)
<223> OTHER INFORMATION: Y.lipolytica codon-optimized nucleotide
      sequence of thioesterase from Cuphea palustris CpFATB2

<400> SEQUENCE: 22
atggtggccg ctgccgcctc cgccgccttc ttctctgtgg ccacccctcg aactaacatc      60
tctccctcgt ctctgtctgt gcccttcaag cccaagtcta accacaacgg cggcttccag     120
gtgaaggcca acgcctctgc caccccaag gccaacggat ctgccgtgtc tctgaagtct      180
ggctctctcg agactcagga ggacaagacc tcttcttcgt cgcctcctcc ccgaaccttc     240
atcaaccagc tgcccgtgtg gtctatgctg ctgtctgccg tgaccaccgt gttcggcgtg     300
gccgagaagc agtggcccat gctggaccga aagtctaagc gacccgacat gctggtcgag     360
cccctgggcg tggaccgaat cgtgtacgac ggcgtgtctt ccgacagtc tttctctatc      420 cgatcttacg agatcggcgc tgaccgaacc gcctctatcg agactctgat gaacatgttc     480
caggagactt ctctgaacca ctgcaagatc atcggcctgc tgaacgacgg cttcggccga     540
acccctgaga tgtgcaagcg agatctgatt tgggtggtga ccaagatgca gatcgaggtg     600
aaccgatacc ccacctgggg cgacaccatt gaggtgaaca cctgggtgtc tgcctctggc     660
aagcacggca tgggccgaga ctggctgatc tctgactgcc acaccggcga gatcctgatc     720
cgagccacct ctgtgtgggc catgatgaac cagaagaccc gacgactgtc taagatcccc     780
tacgaggtgc gacaggagat cgagccccag ttcgtggact ctgctcccgt gatcgtggac     840
gaccgaaagt tccacaagct ggacctcaag accggcgact ctatctgcaa cggcctgacc     900
cctcgatgga ccgacctgga cgtgaaccag cacgtgaaca cgtgaagta catcggctgg     960 atcctgcagt ctgtgcccac cgaggtgttt gagactcagg agctgtgcgg cctgaccctc    1020
gagtaccgac gagagtgcgg ccgagactct gtgctcgagt ctgtgaccgc catgaccccc    1080
tctaaggagg gcgaccgatc tctgtaccag cacctcctgc gactcgagga cggcgccgac    1140
atcgtgaagg gccgaaccga gtggcgaccc aagaacgctg gcgccaaggg cgccatcctg    1200
accggcaaga cctctaacgg caactctatc tcttaa                              1236
```

<210> SEQ ID NO 23
<211> LENGTH: 411
<212> TYPE: PRT
<213> ORGANISM: Cuphea palustris

<400> SEQUENCE: 23

```
Met Val Ala Ala Ala Ser Ala Ala Phe Phe Ser Val Ala Thr Pro
1               5                   10                  15

Arg Thr Asn Ile Ser Pro Ser Ser Leu Ser Val Pro Phe Lys Pro Lys
                20                  25                  30

Ser Asn His Asn Gly Gly Phe Gln Val Lys Ala Asn Ala Ser Ala His
            35                  40                  45

Pro Lys Ala Asn Gly Ser Ala Val Ser Leu Lys Ser Gly Ser Leu Glu
    50                  55                  60

Thr Gln Glu Asp Lys Thr Ser Ser Ser Pro Pro Pro Arg Thr Phe
65                  70                  75                  80

Ile Asn Gln Leu Pro Val Trp Ser Met Leu Leu Ser Ala Val Thr Thr
                85                  90                  95

Val Phe Gly Val Ala Glu Lys Gln Trp Pro Met Leu Asp Arg Lys Ser
                100                 105                 110

Lys Arg Pro Asp Met Leu Val Glu Pro Leu Gly Val Asp Arg Ile Val
            115                 120                 125

Tyr Asp Gly Val Ser Phe Arg Gln Ser Phe Ser Ile Arg Ser Tyr Glu
    130                 135                 140

Ile Gly Ala Asp Arg Thr Ala Ser Ile Glu Thr Leu Met Asn Met Phe
145                 150                 155                 160

Gln Glu Thr Ser Leu Asn His Cys Lys Ile Ile Gly Leu Leu Asn Asp
                165                 170                 175

Gly Phe Gly Arg Thr Pro Glu Met Cys Lys Arg Asp Leu Ile Trp Val
            180                 185                 190

Val Thr Lys Met Gln Ile Glu Val Asn Arg Tyr Pro Thr Trp Gly Asp
    195                 200                 205

Thr Ile Glu Val Asn Thr Trp Val Ser Ala Ser Gly Lys His Gly Met
210                 215                 220

Gly Arg Asp Trp Leu Ile Ser Asp Cys His Thr Gly Glu Ile Leu Ile
225                 230                 235                 240

Arg Ala Thr Ser Val Trp Ala Met Met Asn Gln Lys Thr Arg Arg Leu
                245                 250                 255

Ser Lys Ile Pro Tyr Glu Val Arg Gln Glu Ile Glu Pro Gln Phe Val
            260                 265                 270

Asp Ser Ala Pro Val Ile Val Asp Arg Lys Phe His Lys Leu Asp
    275                 280                 285

Leu Lys Thr Gly Asp Ser Ile Cys Asn Gly Leu Thr Pro Arg Trp Thr
    290                 295                 300

Asp Leu Asp Val Asn Gln His Val Asn Asn Val Lys Tyr Ile Gly Trp
305                 310                 315                 320

Ile Leu Gln Ser Val Pro Thr Glu Val Phe Glu Thr Gln Glu Leu Cys
                325                 330                 335

Gly Leu Thr Leu Glu Tyr Arg Arg Glu Cys Gly Arg Asp Ser Val Leu
            340                 345                 350

Glu Ser Val Thr Ala Met Asp Pro Ser Lys Glu Gly Asp Arg Ser Leu
    355                 360                 365

Tyr Gln His Leu Leu Arg Leu Glu Asp Gly Ala Asp Ile Val Lys Gly
    370                 375                 380
```

```
Arg Thr Glu Trp Arg Pro Lys Asn Ala Gly Ala Lys Gly Ala Ile Leu
385                 390                 395                 400

Thr Gly Lys Thr Ser Asn Gly Asn Ser Ile Ser
                405                 410
```

<210> SEQ ID NO 24
<211> LENGTH: 1368
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1368)
<223> OTHER INFORMATION: S. cerevisiae-codon-optimized nucleotide
      sequence of Helicoverpa armigera fatty acyl reductase; mRNA-coding
      sequence

<400> SEQUENCE: 24

```
atggttgtct tgacctccaa agaaactaag ccatctgttg ctgaatttta cgctggtaag      60
tctgttttca ttactggtgg tactggtttc ttgggtaagg ttttcattga aaagttgttg     120
tactcctgcc cagatatcgg taatatctac atgttgatca gagaaaagaa gggtttgtcc     180
gtttccgaaa gaatcaagca cttttttgat gatcctttgt tcaccagatt gaagaaaaaa     240
agaccagccg acttggaaaa gatcgttttg attccaggtg atattactgc tccagatttg     300
ggtattacct ccgaaaacga aaagatgttg atcgaaaagg tcagtgtcat tattcattct     360
gctgctaccg ttaagttcaa cgaaccattg ccaactgctt ggaagattaa cgttgaaggt     420
actagaatga tgttggcctt gtctagaaga atgaagagaa tcgaagtttt catccatatc     480
tctaccgctt acactaacac caacagagaa gttgttgacg aaatcttgta ccagctcca      540
gctgatattg atcaagttca cagatatgtt aaggacggta tctctgaaga agaaactgaa     600
aaaatcttga acggtagacc aaacacttac actttcacta aggctttgac cgaacatttg     660
gttgctgaaa tcaagctta cgttccaacc attatcgtta ccatcagtg tgttgctgcc      720
attaaggatg aacctattaa gggttggttg gtaattggt atggtgctac aggtttgact     780
gttttactg ctaagggttt gaacagagtt atctacggtc actcttctaa catcgttgat     840
ttgatcccag ttgattacgt tgccaacttg gttattgctg ctggtgctaa atcttctaag     900
tctactgaat tgaaggtcta caactgctgt tcttctgctt gtaacccaat tactatcggt     960
aagttgatgt ccatgttgc tgaagatgct atcaagcaaa agtcttacgc tatgccattg    1020
ccaggttggt acattttac taagtacaag tggttggtct tgttgttgac cattttgttc    1080
caagttattc cagcctacat taccgacttg tacagacatt tgattggtaa gaacccaaga    1140
tatatcaagt tgcaatcctt ggtcaatcaa accagatcct ccattgattt cttcacctct    1200
cattcttggg ttatgaaggc tgatagagtc agagaattat tcgcttcttt gtctccagca    1260
gataagtact tgtttccatg tgatccaacc gatattaact ggacccatta cattcaagat    1320
tactgctggg tgttagaca tttcttggaa aaaaaaagct acgaataa                  1368
```

<210> SEQ ID NO 25
<211> LENGTH: 455
<212> TYPE: PRT
<213> ORGANISM: Helicoverpa armigera

<400> SEQUENCE: 25

```
Met Val Val Leu Thr Ser Lys Glu Thr Lys Pro Ser Val Ala Glu Phe
1               5                   10                  15
```

```
Tyr Ala Gly Lys Ser Val Phe Ile Thr Gly Thr Gly Phe Leu Gly
            20                  25                  30

Lys Val Phe Ile Glu Lys Leu Leu Tyr Ser Cys Pro Asp Ile Gly Asn
        35                  40                  45

Ile Tyr Met Leu Ile Arg Glu Lys Lys Gly Leu Ser Val Ser Glu Arg
    50                  55                  60

Ile Lys His Phe Leu Asp Asp Pro Leu Phe Thr Arg Leu Lys Glu Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Thr Ser Glu Asn Glu Lys Met Leu Ile Glu
            100                 105                 110

Lys Val Ser Val Ile Ile His Ser Ala Ala Thr Val Lys Phe Asn Glu
        115                 120                 125

Pro Leu Pro Thr Ala Trp Lys Ile Asn Val Glu Gly Thr Arg Met Met
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Arg Tyr Val Lys Asp
            180                 185                 190

Gly Ile Ser Glu Glu Thr Glu Lys Ile Leu Asn Gly Arg Pro Asn
        195                 200                 205

Thr Tyr Thr Phe Thr Lys Ala Leu Thr Glu His Leu Val Ala Glu Asn
    210                 215                 220

Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
            260                 265                 270

Gly His Ser Ser Asn Ile Val Asp Leu Ile Pro Val Asp Tyr Val Ala
        275                 280                 285

Asn Leu Val Ile Ala Ala Gly Ala Lys Ser Ser Lys Ser Thr Glu Leu
    290                 295                 300

Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
                325                 330                 335

Ala Met Pro Leu Pro Gly Trp Tyr Ile Phe Thr Lys Tyr Lys Trp Leu
            340                 345                 350

Val Leu Leu Leu Thr Ile Leu Phe Gln Val Ile Pro Ala Tyr Ile Thr
        355                 360                 365

Asp Leu Tyr Arg His Leu Ile Gly Lys Asn Pro Arg Tyr Ile Lys Leu
    370                 375                 380

Gln Ser Leu Val Asn Gln Thr Arg Ser Ser Ile Asp Phe Phe Thr Ser
385                 390                 395                 400

His Ser Trp Val Met Lys Ala Asp Arg Val Arg Glu Leu Phe Ala Ser
                405                 410                 415

Leu Ser Pro Ala Asp Lys Tyr Leu Phe Pro Cys Asp Pro Thr Asp Ile
            420                 425                 430

Asn Trp Thr His Tyr Ile Gln Asp Tyr Cys Trp Gly Val Arg His Phe
```

Leu Glu Lys Lys Ser Tyr Glu
    450             455

<210> SEQ ID NO 26
<211> LENGTH: 1365
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1365)
<223> OTHER INFORMATION: S. cerevisiae-codon-optimized nucleotide
      sequence of H. armigera fatty acyl reductase with signal peptide
      changed to HDEL; DNA coding sequence.

<400> SEQUENCE: 26

| | | | | |
|---|---|---|---|---|
| atggttgtct | tgacctccaa | agaaactaag | ccatctgttg | ctgaatttta cgctggtaag | 60 |
| tctgttttca | ttactggtgg | tactggtttc | ttgggtaagg | ttttcattga aaagttgttg | 120 |
| tactcctgcc | agatatcgg | taatatctac | atgttgatca | gagaaaagaa gggtttgtcc | 180 |
| gtttccgaaa | gaatcaagca | cttttttggat | gatcctttgt | tcaccagatt gaaagaaaaa | 240 |
| agaccagccg | acttggaaaa | gatcgttttg | attccaggtg | atattactgc tccagatttg | 300 |
| ggtattacct | ccgaaaacga | aaagatgttg | atcgaaaagg | tcagtgtcat tattcattct | 360 |
| gctgctaccg | ttaagttcaa | cgaaccattg | ccaactgctt | ggaagattaa cgttgaaggt | 420 |
| actagaatga | tgttggcctt | gtctagaaga | atgaagagaa | tcgaagtttt catccatatc | 480 |
| tctaccgctt | acactaacac | caacagagaa | gttgttgacg | aaatcttgta ccagctcca | 540 |
| gctgatattg | atcaagttca | cagatatgtt | aaggacggta | tctctgaaga agaaactgaa | 600 |
| aaaatcttga | acggtagacc | aaaacacttac | actttcacta | aggctttgac cgaacatttg | 660 |
| gttgctgaaa | tcaagcttta | cgttccaacc | attatcgtta | gaccatcagt tgttgctgcc | 720 |
| attaaggatg | aacctattaa | gggttggttg | ggtaattggt | atggtgctac aggtttgact | 780 |
| gttttttactg | ctaagggttt | gaacagagtt | atctacggtc | actcttctaa catcgttgat | 840 |
| ttgatcccag | ttgattacgt | tgccaacttg | gttattgctc | tggtgctaa atcttctaag | 900 |
| tctactgaat | tgaaggtcta | caactgctgt | tcttctgctt | gtaacccaat tactatcggt | 960 |
| aagttgatgt | ccatgtttgc | tgaagatgct | atcaagcaaa | agtcttacgc tatgccattg | 1020 |
| ccaggttggt | acatttttac | taagtacaag | tggttggtct | tgttgttgac catttttgttc | 1080 |
| caagttattc | cagcctacat | taccgacttg | tacagacatt | tgattggtaa gaacccaaga | 1140 |
| tatatcaagt | tgcaatcctt | ggtcaatcaa | accagatcct | ccattgattt cttcacctct | 1200 |
| cattcttggg | ttatgaaggc | tgatagagtc | agagaattat | tcgcttctt gtctccagca | 1260 |
| gataagtact | tgtttccatg | tgatccaacc | gatattaact | ggacccatta cattcaagat | 1320 |
| tactgctggg | gtgttagaca | ttctccttggaa | catgatgaat | tgtaa | 1365 |

<210> SEQ ID NO 27
<211> LENGTH: 454
<212> TYPE: PRT
<213> ORGANISM: Helicoverpa armigera
<220> FEATURE:
<221> NAME/KEY: MISC_FEATURE
<222> LOCATION: (1)..(454)
<223> OTHER INFORMATION: H. armigera fatty acyl reductase with signal
      peptide changed to HDEL

<400> SEQUENCE: 27

-continued

```
Met Val Val Leu Thr Ser Lys Glu Thr Lys Pro Ser Val Ala Glu Phe
1               5                   10                  15

Tyr Ala Gly Lys Ser Val Phe Ile Thr Gly Gly Thr Gly Phe Leu Gly
                20                  25                  30

Lys Val Phe Ile Glu Lys Leu Leu Tyr Ser Cys Pro Asp Ile Gly Asn
            35                  40                  45

Ile Tyr Met Leu Ile Arg Glu Lys Lys Gly Leu Ser Val Ser Glu Arg
        50                  55                  60

Ile Lys His Phe Leu Asp Asp Pro Leu Phe Thr Arg Leu Lys Glu Lys
65                      70                  75                  80

Arg Pro Ala Asp Leu Glu Lys Ile Val Leu Ile Pro Gly Asp Ile Thr
                85                  90                  95

Ala Pro Asp Leu Gly Ile Thr Ser Glu Asn Glu Lys Met Leu Ile Glu
            100                 105                 110

Lys Val Ser Val Ile Ile His Ser Ala Ala Thr Val Lys Phe Asn Glu
        115                 120                 125

Pro Leu Pro Thr Ala Trp Lys Ile Asn Val Glu Gly Thr Arg Met Met
    130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Arg Tyr Val Lys Asp
            180                 185                 190

Gly Ile Ser Glu Glu Thr Glu Lys Ile Leu Asn Gly Arg Pro Asn
        195                 200                 205

Thr Tyr Thr Phe Thr Lys Ala Leu Thr Glu His Leu Val Ala Glu Asn
    210                 215                 220

Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
            260                 265                 270

Gly His Ser Ser Asn Ile Val Asp Leu Ile Pro Val Asp Tyr Val Ala
        275                 280                 285

Asn Leu Val Ile Ala Ala Gly Ala Lys Ser Ser Lys Ser Thr Glu Leu
    290                 295                 300

Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
                325                 330                 335

Ala Met Pro Leu Pro Gly Trp Tyr Ile Phe Thr Lys Tyr Lys Trp Leu
            340                 345                 350

Val Leu Leu Leu Thr Ile Leu Phe Gln Val Ile Pro Ala Tyr Ile Thr
        355                 360                 365

Asp Leu Tyr Arg His Leu Ile Gly Lys Asn Pro Arg Tyr Ile Lys Leu
    370                 375                 380

Gln Ser Leu Val Asn Gln Thr Arg Ser Ser Ile Asp Phe Phe Thr Ser
385                 390                 395                 400

His Ser Trp Val Met Lys Ala Asp Arg Val Arg Glu Leu Phe Ala Ser
                405                 410                 415
```

Leu Ser Pro Ala Asp Lys Tyr Leu Phe Pro Cys Asp Pro Thr Asp Ile
            420                 425                 430

Asn Trp Thr His Tyr Ile Gln Asp Tyr Cys Trp Gly Val Arg His Phe
            435                 440                 445

Leu Glu His Asp Glu Leu
    450

<210> SEQ ID NO 28
<211> LENGTH: 1371
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1371)
<223> OTHER INFORMATION: S. cerevisiae-codon-optimized nucleotide
      sequence of H. assulta fatty acyl reductase; mRNA-coding sequence

<400> SEQUENCE: 28
atggttgtct tgacctccaa agaaactaag ccatctgttg ctgaatttta cgctggtaag      60
tctgttttca ttactggtgg tactggtttc ttgggtaaga tcttcattga aaagttgttg     120
tactcctgcc agatatcgg taatatctac atgttgatca gagaaagaa gggtttgtcc      180 gtttccgaaa gaatcaagca attttttggat gacccttttgt tcaccagatt gaaagaaaaa    240
agaccagccg acttggaaaa gatcgttttg attccaggtg atattactgc tccagatttg     300
ggtattacct ccgaaaacga aaagatgttg atcgaaaagg tcagtgtcat tattcattct     360
gctgctaccg ttaagttcaa cgaaccattg ccaactgctt ggaagattaa cgttgaaggt     420
actagaatga tgttggcctt gtctagaaga atgaagagaa tcgaagtttt catccatatc     480
tctaccgctt acactaacac caacagagaa gttgttgacg aaatcttgta tccagctcca     540
gctgatattg atcaagttca ccaatatgtt aaggacggta tctctgaaga gaaaactgaa     600
aaaatcttga acggtagacc aaacacttac actttcacta aggctttgac cgaacatttg     660
gttgctgaaa tcaagcttta cgttccaacc attatcgtta gaccatcagt tgttgctgcc     720
attaaggatg aacctattaa gggttggttg ggtaattggt atggtgctac aggttttgact    780 gttttttactg ctaagggttt gaacagagtt atctacggtc attcctctta catcgttgat    840
ttgatcccag ttgattacgt tgccaacttg gttattgctg ctggtgctaa atcttctaag    900
tctactgaat tgaaggtcta caactgctgt tcttctgctt gtaacccaat tactatcggt     960
aagttgatgt ccatgttttgc tgaagatgct atcaagcaaa agtcttacgc tatgccattg    1020
ccaggttggt atgttttttac aaagtacaag tggttggtct tgttgttgac cattttgttc    1080
caagttattc cagcctacat taccgacttg tacagacatt tgattggtaa gaacccaaga    1140
tatatcaagt tgcaatcctt ggtcaatcaa accagatcct ccattgattt cttcacctct    1200
cattcttggg ttatgaaggc tgatagagtc agagaattat tcgcttcttt gtctccagca    1260
gataagtact tgtttccatg tgatccaacc gatattaact ggacccatta cattcaagat    1320
tactgctggg gtgttagaca cttcttggaa aaaagactaa ccaacaagta a           1371

<210> SEQ ID NO 29
<211> LENGTH: 456
<212> TYPE: PRT
<213> ORGANISM: Helicoverpa assulta

<400> SEQUENCE: 29

Met Val Val Leu Thr Ser Lys Glu Thr Lys Pro Ser Val Ala Glu Phe

```
  1               5                  10                 15
Tyr Ala Gly Lys Ser Val Phe Ile Thr Gly Gly Thr Gly Phe Leu Gly
                 20                 25                 30

Lys Ile Phe Ile Glu Lys Leu Leu Tyr Ser Cys Pro Asp Ile Gly Asn
                 35                 40                 45

Ile Tyr Met Leu Ile Arg Glu Lys Lys Gly Leu Ser Val Ser Glu Arg
                 50                 55                 60

Ile Lys Gln Phe Leu Asp Asp Pro Leu Phe Thr Arg Leu Lys Glu Lys
 65              70                 75                 80

Arg Pro Ala Asp Leu Glu Lys Ile Val Leu Ile Pro Gly Asp Ile Thr
                 85                 90                 95

Ala Pro Asp Leu Gly Ile Thr Ser Glu Asn Glu Lys Met Leu Ile Glu
                100                105                110

Lys Val Ser Val Ile Ile His Ser Ala Ala Thr Val Lys Phe Asn Glu
                115                120                125

Pro Leu Pro Thr Ala Trp Lys Ile Asn Val Glu Gly Thr Arg Met Met
                130                135                140

Leu Ala Leu Ser Arg Arg Met Lys Arg Ile Glu Val Phe Ile His Ile
145              150                155                160

Ser Thr Ala Tyr Thr Asn Thr Asn Arg Glu Val Val Asp Glu Ile Leu
                 165                170                175

Tyr Pro Ala Pro Ala Asp Ile Asp Gln Val His Gln Tyr Val Lys Asp
                180                185                190

Gly Ile Ser Glu Glu Glu Thr Glu Lys Ile Leu Asn Gly Arg Pro Asn
                195                200                205

Thr Tyr Thr Phe Thr Lys Ala Leu Thr Glu His Leu Val Ala Glu Asn
210              215                220

Gln Ala Tyr Val Pro Thr Ile Ile Val Arg Pro Ser Val Ala Ala
225              230                235                240

Ile Lys Asp Glu Pro Ile Lys Gly Trp Leu Gly Asn Trp Tyr Gly Ala
                245                250                255

Thr Gly Leu Thr Val Phe Thr Ala Lys Gly Leu Asn Arg Val Ile Tyr
                260                265                270

Gly His Ser Ser Tyr Ile Val Asp Leu Ile Pro Val Asp Tyr Val Ala
                275                280                285

Asn Leu Val Ile Ala Ala Gly Ala Lys Ser Ser Lys Ser Thr Glu Leu
                290                295                300

Lys Val Tyr Asn Cys Cys Ser Ser Ala Cys Asn Pro Ile Thr Ile Gly
305              310                315                320

Lys Leu Met Ser Met Phe Ala Glu Asp Ala Ile Lys Gln Lys Ser Tyr
                325                330                335

Ala Met Pro Leu Pro Gly Trp Tyr Val Phe Thr Lys Tyr Lys Trp Leu
                340                345                350

Val Leu Leu Leu Thr Ile Leu Phe Gln Val Ile Pro Ala Tyr Ile Thr
                355                360                365

Asp Leu Tyr Arg His Leu Ile Gly Lys Asn Pro Arg Tyr Ile Lys Leu
                370                375                380

Gln Ser Leu Val Asn Gln Thr Arg Ser Ser Ile Asp Phe Phe Thr Ser
385              390                395                400

His Ser Trp Val Met Lys Ala Asp Arg Val Arg Glu Leu Phe Ala Ser
                405                410                415

Leu Ser Pro Ala Asp Lys Tyr Leu Phe Pro Cys Asp Pro Thr Asp Ile
                420                425                430
```

Asn Trp Thr His Tyr Ile Gln Asp Tyr Cys Trp Gly Val Arg His Phe
    435                 440                 445

Leu Glu Lys Lys Thr Thr Asn Lys
    450                 455

<210> SEQ ID NO 30
<211> LENGTH: 1365
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1365)
<223> OTHER INFORMATION: S. cerevisiae-codon-optimized nucleotide
      sequence of Helicoverpa assulta fatty acyl reductase with signal
      peptide changed to HDEL; mRNA-coding sequence

<400> SEQUENCE: 30
atggttgtct tgacctccaa agaaactaag ccatctgttg ctgaattta cgctggtaag      60 tctgttttca ttactggtgg tactggtttc ttgggtaaga tcttcattga aaagttgttg     120
tactcctgcc agatatcgg taatatctac atgttgatca gagaaagaa gggtttgtcc      180 gtttccgaaa gaatcaagca atttttggat gacccttgt tcaccagatt gaaagaaaaa     240
agaccagccg acttggaaaa gatcgttttg attccaggtg atattactgc tccagatttg    300
ggtattacct ccgaaaacga aaagatgttg atcgaaaagg tcagtgtcat tattcattct    360
gctgctaccg ttaagttcaa cgaaccattg ccaactgctt ggaagattaa cgttgaaggt    420
actagaatga tgttggcctt gtctagaaga atgaagagaa tcgaagtttt catccatatc    480
tctaccgctt acactaacac caacagagaa gttgttgacg aaatcttgta tccagctcca    540
gctgatattg atcaagttca ccaatatgtt aaggacggta tctctgaaga gaaaactgaa    600
aaaatcttga acggtagacc aaacacttac actttcacta aggctttgac cgaacatttg    660
gttgctgaaa atcaagctta cgttccaacc attatcgtta gaccatcagt tgttgctgcc    720
attaaggatg aacctattaa gggttggttg ggtaattggt atggtgctac aggttttgact   780 gttttttactg ctaagggttt gaacagagtt atctacggtc attcctctta catcgttgat   840
ttgatcccag ttgattacgt tgccaacttg gttattgctg ctggtgctaa atcttctaag    900
tctactgaat tgaaggtcta caactgctgt cttctgcttg taacccaat tactatcggt     960 aagttgatgt ccatgttgc tgaagatgct atcaagcaaa agtcttacgc tatgccattg     1020
ccaggttggt atgtttttac aaagtacaag tggttggtct tgttgttgac catttgttc    1080 caagttattc cagcctacat taccgacttg tacagacatt tgattggtaa gaacccaaga    1140
tatatcaagt tgcaatcctt ggtcaatcaa accagatcct ccattgattt cttcacctct    1200
cattcttggg ttatgaaggc tgatagagtc agagaattat tcgcttcttt gtctccagca   1260
gataagtact tgtttccatg tgatccaacc gatattaact ggaccccatta cattcaagat   1320 tactgctggg gtgttagaca cttcttggaa catgatgaat tgtaa                   1365

<210> SEQ ID NO 31
<211> LENGTH: 454
<212> TYPE: PRT
<213> ORGANISM: Helicoverpa assulta
<220> FEATURE:
<221> NAME/KEY: MISC_FEATURE
<222> LOCATION: (1)..(454)
<223> OTHER INFORMATION: amino acid sequence of H. assulta fatty acyl
      reductase with signal peptide changed to HDEL

<400> SEQUENCE: 31

Met Val Val Leu Thr Ser Lys Glu Thr Lys Pro Ser Val Ala Glu Phe
1               5                   10                  15

Tyr Ala Gly Lys Ser Val Phe Ile Thr Gly Thr Gly Phe Leu Gly
            20                  25                  30

Lys Ile Phe Ile Glu Lys Leu Leu Tyr Ser Cys Pro Asp Ile Gly Asn
                35                  40                  45

Ile Tyr Met Leu Ile Arg Glu Lys Lys Gly Leu Ser Val Ser Glu Arg
50                  55                  60

Ile Lys Gln Phe Leu Asp Asp Pro Leu Phe Thr Arg Leu Lys Glu Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Thr Ser Glu Asn Glu Lys Met Leu Ile Glu
                100                 105                 110

Lys Val Ser Val Ile Ile His Ser Ala Ala Thr Val Lys Phe Asn Glu
                115                 120                 125

Pro Leu Pro Thr Ala Trp Lys Ile Asn Val Glu Gly Thr Arg Met Met
130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
                180                 185                 190

Gly Ile Ser Glu Glu Thr Glu Lys Ile Leu Asn Gly Arg Pro Asn
                195                 200                 205

Thr Tyr Thr Phe Thr Lys Ala Leu Thr Glu His Leu Val Ala Glu Asn
210                 215                 220

Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
                260                 265                 270

Gly His Ser Ser Tyr Ile Val Asp Leu Ile Pro Val Asp Tyr Val Ala
                275                 280                 285

Asn Leu Val Ile Ala Ala Gly Ala Lys Ser Ser Lys Ser Thr Glu Leu
                290                 295                 300

Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
                325                 330                 335

Ala Met Pro Leu Pro Gly Trp Tyr Val Phe Thr Lys Tyr Lys Trp Leu
                340                 345                 350

Val Leu Leu Leu Thr Ile Leu Phe Gln Val Ile Pro Ala Tyr Ile Thr
                355                 360                 365

Asp Leu Tyr Arg His Leu Ile Gly Lys Asn Pro Arg Tyr Ile Lys Leu
                370                 375                 380

Gln Ser Leu Val Asn Gln Thr Arg Ser Ser Ile Asp Phe Phe Thr Ser
385                 390                 395                 400

His Ser Trp Val Met Lys Ala Asp Arg Val Arg Glu Leu Phe Ala Ser 405                 410                 415
Leu Ser Pro Ala Asp Lys Tyr Leu Phe Pro Cys Asp Pro Thr Asp Ile
        420                 425                 430

Asn Trp Thr His Tyr Ile Gln Asp Tyr Cys Trp Gly Val Arg His Phe
        435                 440                 445

Leu Glu His Asp Glu Leu
    450

<210> SEQ ID NO 32
<211> LENGTH: 1362
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1362)
<223> OTHER INFORMATION: S. cerevisiae-codon-optimized nucleotide
      sequence of Heliothis subflexa fatty acyl reductase; mRNA-coding
      sequence.

<400> SEQUENCE: 32
atggttgtct tgacctccaa agaaactaag ccatctgttg ctgaattta cgctggtaag      60 tctgttttca ttactggtgg tactggtttc ttgggtaagg ttttcattga aaagttgttg    120
tactcctgcc cagatatcgg taatatctac atgttgatca gagaaagaa gggtttgtcc    180 gtttccgaaa gaatcaagca ctttttggat gatcctttgt tcaccagatt gaaagaaaaa    240
agaccagccg acttggaaaa gatcgttttg attccaggtg atattactgc tccagatttg    300
ggtattacct ccgaaaacga aagatgttg atcgaaaagg tcagtgtcat tattcattct    360
gctgctaccg ttaagttcaa cgaaccattg ccaactgctt ggaagattaa cgttgaaggt    420
actagaatga tgttggcctt gtctagaaga atgaagagaa tcgaagtttt catccatatc    480
tctaccgctt acactaacac caacagaaa gttgttgacg aaatcttgta tccagctcca    540
gctgatattg atcaagttca ccaatatgtt aaggacggta tctctgaaga agaaactgaa    600
aaaatcttga acggtagacc aaacacttac actttcacta aggctttgac cgaacatttg    660
gttgctgaaa tcaagctta cgttccaacc attatcgtta gaccatcagt tgttgctgcc    720
attaaggatg aacctattaa gggttggttg ggtaattggt atggtgctac aggtttgact    780 gttttttactg ctaagggttt gaacagagtt atctacggtc actcttctaa catcgttgat    840
ttgatcccag ttgattacgt tgccaacttg gttattgctg ctggtgctaa atcttctaag    900
tctactgaat gaaggtcta caactgctgt tcttctgctt gtaacccaat tactatcggt    960
aagttgatgt ccatgtttgc tgaagatgct atcaagcaaa agtcttacgc tatgccattg   1020
ccaggttggt acattttttac taagtacaag tggttggtct tgttgttgac catttttgttc   1080 caagttattc cagcctacat taccgacttg tacagacatt tgattggtaa gaacccaaga   1140
tatatcaagt tgcaatcctt ggtcaatcaa accagatcct ccattgattt cttcaccaac   1200
cattcttggg ttatgaaggc tgatagagtc agagaattat tcgcttcttt gtctccagca   1260
gataagtact tgtttccatg tgatccagtc aacatcaatt ggagacaata tccaagat    1320 tactgctggg gtgttagaca tttcttggaa aaaagactt aa                       1362

<210> SEQ ID NO 33
<211> LENGTH: 453
<212> TYPE: PRT
<213> ORGANISM: Heliothis subflexa

```
<400> SEQUENCE: 33

Met Val Val Leu Thr Ser Lys Glu Thr Lys Pro Ser Val Ala Glu Phe
1               5                   10                  15

Tyr Ala Gly Lys Ser Val Phe Ile Thr Gly Thr Gly Phe Leu Gly
            20                  25                  30

Lys Val Phe Ile Glu Lys Leu Leu Tyr Ser Cys Pro Asp Ile Gly Asn
            35                  40                  45

Ile Tyr Met Leu Ile Arg Glu Lys Lys Gly Leu Ser Val Ser Glu Arg
50                  55                  60

Ile Lys His Phe Leu Asp Asp Pro Leu Phe Thr Arg Leu Lys Glu Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Thr Ser Glu Asn Gly Lys Met Leu Ile Glu
                100                 105                 110

Lys Val Ser Val Ile Ile His Ser Ala Ala Thr Val Lys Phe Asn Glu
            115                 120                 125

Pro Leu Pro Thr Ala Trp Lys Ile Asn Val Glu Gly Thr Arg Met Met
            130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
            180                 185                 190

Gly Ile Ser Glu Glu Glu Thr Glu Lys Ile Leu Asn Gly Arg Pro Asn
            195                 200                 205

Thr Tyr Thr Phe Thr Lys Ala Leu Thr Glu His Leu Val Ala Glu Asn
210                 215                 220

Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
            260                 265                 270

Gly His Ser Ser Asn Ile Val Asp Leu Ile Pro Val Asp Tyr Val Ala
            275                 280                 285

Asn Leu Val Ile Ala Ala Gly Ala Lys Ser Ser Lys Ser Thr Glu Leu
            290                 295                 300

Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
                325                 330                 335

Ala Met Pro Leu Pro Gly Trp Tyr Ile Phe Thr Lys Tyr Lys Trp Leu
            340                 345                 350

Val Leu Leu Leu Thr Ile Leu Phe Gln Val Ile Pro Ala Tyr Ile Thr
            355                 360                 365

Asp Leu Tyr Arg His Leu Ile Gly Lys Asn Pro Arg Tyr Ile Lys Leu
            370                 375                 380

Gln Ser Leu Val Asn Gln Thr Arg Ser Ser Ile Asp Phe Phe Thr Asn
385                 390                 395                 400

His Ser Trp Val Met Lys Ala Asp Arg Val Arg Glu Leu Phe Ala Ser
                405                 410                 415
```

Leu Ser Pro Ala Asp Lys Tyr Leu Phe Pro Cys Asp Pro Val Asn Ile
       420                 425                 430

Asn Trp Arg Gln Tyr Ile Gln Asp Tyr Cys Trp Gly Val Arg His Phe
       435                 440                 445

Leu Glu Lys Lys Thr
    450

<210> SEQ ID NO 34
<211> LENGTH: 1362
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1362)
<223> OTHER INFORMATION: S. cerevisiae-codon-optimized nucleotide
      sequence of H. subflexa fatty acyl reductase with signal peptide
      changed to HDEL; mRNA-coding sequence

<400> SEQUENCE: 34
atggttgtct tgacctccaa agaaactaag ccatctgttg ctgaatttta cgctggtaag      60
tctgttttca ttactggtgg tactggtttc ttgggtaagg ttttcattga aaagttgttg     120
tactcctgcc cagatatcgg taatatctac atgttgatca gagaaaagaa gggtttgtcc     180
gtttccgaaa gaatcaagca ctttttggat gatcctttgt tcaccagatt gaagaaaaa      240 agaccagccg acttggaaaa gatcgttttg attccaggtg atattactgc tccagatttg     300
ggtattacct ccgaaaacga aaagatgttg atcgaaaagg tcagtgtcat tattcattct     360
gctgctaccg ttaagttcaa cgaaccattg ccaactgctt ggaagattaa cgttgaaggt     420
actagaatga tgttggcctt gtctagaaga atgaagagaa tcgaagtttt catccatatc     480
tctaccgctt acactaacac caacagagaa gttgttgacg aaatcttgta ccagctcca     540 gctgatattg atcaagttca ccaatatgtt aaggacggta tctctgaaga agaaactgaa     600
aaaatcttga acggtagacc aaacacttac actttcacta aggctttgac cgaacatttg     660
gttgctgaaa tcaagcttac cgttccaacc attatcgtta gaccatcagt tgttgctgcc     720
attaaggatg aacctattaa gggttggttg ggtaattggt atggtgctac aggtttgact     780 gttttactg ctaagggttt gaacagagtt atctacggtc actcttctaa catcgttgat     840
ttgatcccag ttgattacgt tgccaacttg gttattgctg ctggtgctaa atcttctaag     900
tctactgaat tgaaggtcta caactgctgt tcttctgctt gtaacccaat tactatcggt     960
aagttgatgt ccatgtttgc tgaagatgct atcaagcaaa agtcttacgc tatgccattg    1020
ccaggttggt acattttac taagtacaag tggttggtct tgttgttgac catttttgttc    1080 caagttattc cagcctacat taccgacttg tacagacatt tgattggtaa gaacccaaga    1140
tatatcaagt tgcaatcctt ggtcaatcaa accagatcct ccattgattt cttcaccaac    1200
cattcttggg ttatgaaggc tgatagagtc agagaattat tcgcttcttt gtctccagca    1260
gataagtact tgtttccatg tgatccagtc aacatcaatt ggagacaata tccaagat     1320 tactgctggg gtgttagaca tttcttgcat gatgaattgt aa                       1362

<210> SEQ ID NO 35
<211> LENGTH: 453
<212> TYPE: PRT
<213> ORGANISM: Heliothis subflexa
<220> FEATURE:
<221> NAME/KEY: MISC_FEATURE
<222> LOCATION: (1)..(453)
<223> OTHER INFORMATION: amino acid sequence of H. subflexa fatty acyl
    reductase with signal peptide changed to HDEL

<400> SEQUENCE: 35

Met Val Val Leu Thr Ser Lys Glu Thr Lys Pro Ser Val Ala Glu Phe
1               5                   10                  15

Tyr Ala Gly Lys Ser Val Phe Ile Thr Gly Thr Gly Phe Leu Gly
            20                  25                  30

Lys Val Phe Ile Glu Lys Leu Leu Tyr Ser Cys Pro Asp Ile Gly Asn
                35                  40                  45

Ile Tyr Met Leu Ile Arg Glu Lys Lys Gly Leu Ser Val Ser Glu Arg
50                  55                  60

Ile Lys His Phe Leu Asp Asp Pro Leu Phe Thr Arg Leu Lys Glu Lys
65                  70                  75                  80

Arg Pro Ala Asp Leu Glu Lys Ile Val Leu Ile Pro Gly Asp Ile Thr
                85                  90                  95

Ala Pro Asp Leu Gly Ile Thr Ser Glu Asn Gly Lys Met Leu Ile Glu
            100                 105                 110

Lys Val Ser Val Ile Ile His Ser Ala Ala Thr Val Lys Phe Asn Glu
            115                 120                 125

Pro Leu Pro Thr Ala Trp Lys Ile Asn Val Glu Gly Thr Arg Met Met
130                 135                 140

Leu Ala Leu Ser Arg Arg Met Lys Arg Ile Glu Val Phe Ile His Ile
145                 150                 155                 160

Ser Thr Ala Tyr Thr Asn Thr Asn Arg Glu Val Val Asp Glu Ile Leu
                165                 170                 175

Tyr Pro Ala Pro Ala Asp Ile Asp Gln Val His Gln Tyr Val Lys Asp
            180                 185                 190

Gly Ile Ser Glu Glu Glu Thr Glu Lys Ile Leu Asn Gly Arg Pro Asn
            195                 200                 205

Thr Tyr Thr Phe Thr Lys Ala Leu Thr Glu His Leu Val Ala Glu Asn
210                 215                 220

Gln Ala Tyr Val Pro Thr Ile Ile Val Arg Pro Ser Val Val Ala Ala
225                 230                 235                 240

Ile Lys Asp Glu Pro Ile Lys Gly Trp Leu Gly Asn Trp Tyr Gly Ala
                245                 250                 255

Thr Gly Leu Thr Val Phe Thr Ala Lys Gly Leu Asn Arg Val Ile Tyr
            260                 265                 270

Gly His Ser Ser Asn Ile Val Asp Leu Ile Pro Val Asp Tyr Val Ala
            275                 280                 285

Asn Leu Val Ile Ala Ala Gly Ala Lys Ser Ser Lys Ser Thr Glu Leu
290                 295                 300

Lys Val Tyr Asn Cys Cys Ser Ser Ala Cys Asn Pro Ile Thr Ile Gly
305                 310                 315                 320

Lys Leu Met Ser Met Phe Ala Glu Asp Ala Ile Lys Gln Lys Ser Tyr
                325                 330                 335

Ala Met Pro Leu Pro Gly Trp Tyr Ile Phe Thr Lys Tyr Lys Trp Leu
            340                 345                 350

Val Leu Leu Leu Thr Ile Leu Phe Gln Val Ile Pro Ala Tyr Ile Thr
            355                 360                 365

Asp Leu Tyr Arg His Leu Ile Gly Lys Asn Pro Arg Tyr Ile Lys Leu
            370                 375                 380

Gln Ser Leu Val Asn Gln Thr Arg Ser Ser Ile Asp Phe Phe Thr Asn

His Ser Trp Val Met Lys Ala Asp Arg Val Arg Glu Leu Phe Ala Ser
385                 390                 395                 400

Leu Ser Pro Ala Asp Lys Tyr Leu Phe Pro Cys Asp Pro Val Asn Ile
        405                 410                 415

Asn Trp Arg Gln Tyr Ile Gln Asp Tyr Cys Trp Gly Val Arg His Phe
420                 425                 430

Leu His Asp Glu Leu
435                 440                 445

450

<210> SEQ ID NO 36
<211> LENGTH: 1086
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1086)
<223> OTHER INFORMATION: Y. lipolytica codon-optimized nucleotide
      sequence of delta9 desaturase from Drosophila melanogaster Dmd9

<400> SEQUENCE: 36
atggctccct actctcgaat ctaccaccag acaagtcgt cccgagagac tggcgtgctg    60
ttcgaggacg acgcccagac cgtggactct gacctgacca ccgaccgatt ccagctgaag   120
cgagccgaga gcgacgact gcccctggtg tggcgaaaca tcatcctgtt cgccctggtg   180
cacctggccg ctctgtacgg cctgcactct atcttcaccc gagccaagct ggccaccact   240
ctgttcgctg ccggcctgta catcatcggc atgctgggcg tgaccgctgg cgcccaccga   300
ctgtgggctc accgaaccta caaggccaag tggcccctgc actgctgct ggtgatcttc   360 aacaccattg ccttccagga cgccgtgtac cactgggccc gagatcaccg agtgcaccac   420
aagtactctg agactgacgc tgaccctcac aacgctaccc gaggcttctt ctttctctcac   480 gtcggctggc tgctgtgcaa gaagcacccc gacatcaagg aaaagggccg aggcctggac   540
ctgtctgacc tgcgagctga ccccatcctg atgttccagc gaaagcacta ctacattctg   600
atgcccctgg cctgcttcgt gctgccaccc gtgattccca tggtgtactg gaacgagact   660
ctggcctctt cctggttcgt ggccaccatg ttccgatggt gcttccagct caacatgacc   720
tggctggtga actctgccgc tcacaagttc ggcaaccgac cttacgacaa gactatgaac   780
cccactcaga cgccttcgt gtctgccttc accttcggcg aaggctggca caactaccac   840
cacgcattcc cttgggacta caagaccgcc gagtggggct gctactctct gaacatcacc   900
accgccttca tcgacctgtt cgctaagatc ggctgggcct acgacctcaa gaccgtggct   960
cccgacgtga tccagcgacg agtgctgcga accggcgacg ctctcacga gctgtgggc  1020 tggggcgaca aggacctgac cgctgaggac gcccgaaacg tcctgctggt ggacaagtct  1080
cgataa                                                            1086

<210> SEQ ID NO 37
<211> LENGTH: 1185
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1185)
<223> OTHER INFORMATION: Y. lipolytica codon-optimised nucleotide
      sequence of thioesterase from Cuphea hookeriana ChFatB3

<400> SEQUENCE: 37

```
atggtggccg ctgccgcctc ttctgccttc ttctcggtgc ccactcctgg catctctccc     60
aagcctggca agttcggcaa cggcggcttc caggtgaagg ccaacgccaa cgctcacccc    120
tcgctgaagt ctggctctct cgagactgag gacgacacct cttcctcttc tccaccacct    180
cgaaccttca tcaaccagct gcctgactgg tctatgctgc tgtctgccat caccaccatc    240
ttcggagccg ccgagaagca gtggatgatg ctggaccgaa agtctaagcg acccgacatg    300
ctgatggaac ccttcggcgt ggactctatc gtgcaggacg gcgtgttctt ccgacagtct    360
ttctctatcc gatcttacga gattggcgcc gaccgaacca cctctatcga gactctgatg    420
aacatgtttc aagagacttc tctgaaccac tgcaagtcta acggcctgct gaacgacggc    480
ttcggacgaa cccctgagat gtgcaagaag ggcctgatct gggtcgtgac caagatgcag    540
gtcgaggtga acagataccc catctggggc gactctattg aggtcaacac ctgggtgtct    600
gagtctggca gaacggcat gggccgagac tggctgatct ctgactgctc taccggcgag    660
atcctggtgc gagccaccct ctgtgtgggc catgatgaacc agaagacccg acgactgtct    720
aagttcccat cgaggtgcg acaagagatc gctcccaact tcgtcgactc tgtccccgtg    780
atcgaggacg accgaaagct gcacaagctg gacgtcaaga ccggcgactc catccacaac    840
ggactgaccc ctcgatggaa cgacctggac gtgaaccagc acgtgaacaa cgtgaagtac    900
atcggctgga tcctgaagtc ggtgcccacc gacgtgttcg aggcccaaga gctgtgcggc    960
gtgaccctcg agtaccgacg agagtgcgga cgagactccg tgatggaatc tgtgaccgct   1020
atggaccccct ctaaagaagg cgaccgatct gtctaccagc acctcctgcg actcgaggac   1080
ggcgccgaca ttgccatcgg ccgaaccgag tggcgaccca gaacgctgg cgccaacggc   1140
gccatctcta ccggaaagac ctctaaccga aactctgtgt cttaa                    1185
```

<210> SEQ ID NO 38
<211> LENGTH: 394
<212> TYPE: PRT
<213> ORGANISM: Cuphea hookeriana

<400> SEQUENCE: 38

```
Met Val Ala Ala Ala Ser Ser Ala Phe Phe Ser Val Pro Thr Pro
1               5                   10                  15

Gly Ile Ser Pro Lys Pro Gly Lys Phe Gly Asn Gly Gly Phe Gln Val
                20                  25                  30

Lys Ala Asn Ala Asn Ala His Pro Ser Leu Lys Ser Gly Ser Leu Glu
            35                  40                  45

Thr Glu Asp Asp Thr Ser Ser Ser Pro Pro Arg Thr Phe Ile
        50                  55                  60

Asn Gln Leu Pro Asp Trp Ser Met Leu Leu Ser Ala Ile Thr Thr Ile
65                  70                  75                  80

Phe Gly Ala Ala Glu Lys Gln Trp Met Met Leu Asp Arg Lys Ser Lys
                85                  90                  95

Arg Pro Asp Met Leu Met Glu Pro Phe Gly Val Asp Ser Ile Val Gln
            100                 105                 110

Asp Gly Val Phe Phe Arg Gln Ser Phe Ser Ile Arg Ser Tyr Glu Ile
        115                 120                 125

Gly Ala Asp Arg Thr Thr Ser Ile Glu Thr Leu Met Asn Met Phe Gln
    130                 135                 140

Glu Thr Ser Leu Asn His Cys Lys Ser Asn Gly Leu Leu Asn Asp Gly
```

```
       145                 150                 155                 160
   Phe Gly Arg Thr Pro Glu Met Cys Lys Lys Gly Leu Ile Trp Val Val
                   165                 170                 175

Thr Lys Met Gln Val Glu Val Asn Arg Tyr Pro Ile Trp Gly Asp Ser
               180                 185                 190

Ile Glu Val Asn Thr Trp Val Ser Glu Ser Gly Lys Asn Gly Met Gly
               195                 200                 205

Arg Asp Trp Leu Ile Ser Asp Cys Ser Thr Gly Glu Ile Leu Val Arg
           210                 215                 220

Ala Thr Ser Val Trp Ala Met Met Asn Gln Lys Thr Arg Arg Leu Ser
   225                 230                 235                 240

Lys Phe Pro Phe Glu Val Arg Gln Glu Ile Ala Pro Asn Phe Val Asp
                   245                 250                 255

Ser Val Pro Val Ile Glu Asp Asp Arg Lys Leu His Lys Leu Asp Val
               260                 265                 270

Lys Thr Gly Asp Ser Ile His Asn Gly Leu Thr Pro Arg Trp Asn Asp
               275                 280                 285

Leu Asp Val Asn Gln His Val Asn Asn Val Lys Tyr Ile Gly Trp Ile
           290                 295                 300

Leu Lys Ser Val Pro Thr Asp Val Phe Glu Ala Gln Glu Leu Cys Gly
   305                 310                 315                 320

Val Thr Leu Glu Tyr Arg Arg Glu Cys Gly Arg Asp Ser Val Met Glu
                   325                 330                 335

Ser Val Thr Ala Met Asp Pro Ser Lys Glu Gly Asp Arg Ser Val Tyr
               340                 345                 350

Gln His Leu Leu Arg Leu Glu Asp Gly Ala Asp Ile Ala Ile Gly Arg
               355                 360                 365

Thr Glu Trp Arg Pro Lys Asn Ala Gly Ala Asn Gly Ala Ile Ser Thr
           370                 375                 380

Gly Lys Thr Ser Asn Arg Asn Ser Val Ser
   385                 390

<210> SEQ ID NO 39
<211> LENGTH: 1149
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1149)
<223> OTHER INFORMATION: Y. lipolytica codon-optimised nucleotide
      sequence of thioesterase from Cinnamomum camphora CcFatB1

<400> SEQUENCE: 39
atggctacca cctctctggc ctctgccttc tgctctatga aggccgtgat gctggcccga      60
gatggccgag aatgaagcc ccgatcttct gacctgcagc tgcgagccgg caacgcccag     120
acctctctga agatgatcaa cggcaccaag ttctcttaca ccgagtcgct gaagaagctg     180
cccgactggt ctatgctgtt cgccgtgatc accaccatct tctctgccgc cgagaagcag     240
tggaccaacc tcgagtggaa gcccaagcct aaccctcctc agctgctgga cgaccacttc     300
ggaccccacg gcctggtgtt ccgacgaacc ttcgccatcc gatcttacga ggtgggcccc     360
gaccgatcta cctctatcgt ggccgtcatg aaccacctcc aagaggccgc tctgaaccac     420
gccaagtctg tgggcatcct cggcgacggc ttcggcacca ctctcgagat gtctaagcga     480
gatctgattt gggtcgtgaa cgaacccac gtcgccgtcg agcgataccc cgcctggggc     540
```

```
gacaccgtcg aggtcgagtg ctgggtgggc gcctctggca acaacggccg acgacacgac    600
tttctggtgc gagactgcaa gaccggcgag attctgaccc gatgtacctc tctgtctgtg    660
atgatgaaca cccgaactcg acgactgtct aagatccccg aggaagtgcg aggcgagatc    720
ggacccgcct tcatcgacaa cgtggccgtg aaggacgagg aaatcaagaa gccccagaag    780
ctgaacgact ctaccgccga ctacatccaa ggcggactga cccctcgatg gaacgacctg    840
gacatcaacc agcacgtgaa caacatcaag tacgtggact ggatcctcga gactgtgccc    900
gactctatct tcgagtctca ccacatctct tcgttcacca tcgagtaccg acgagagtgc    960
accatggact ctgtgctgca gtctctgacc accgtgtctg gcggctcctc tgaggccgga   1020
ctggtgtgcg agcacctcct gcagctcgaa ggcggctctg aggtcctgcg agccaagacc   1080
gagtggcgac ccaagctgac tgactctttc cgaggcatct ctgtgatccc cgccgagtcc   1140
tctgtgtaa                                                          1149
```

<210> SEQ ID NO 40
<211> LENGTH: 382
<212> TYPE: PRT
<213> ORGANISM: Cinnamomum camphora

<400> SEQUENCE: 40

```
Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Gln Thr Ser Leu Lys Met Ile Asn Gly
        35                  40                  45

Thr Lys Phe Ser Tyr Thr Glu Ser Leu Lys Lys Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Asn Pro Pro Gln Leu Leu
                85                  90                  95

Asp Asp His Phe Gly Pro His Gly Leu Val Phe Arg Arg Thr Phe Ala
            100                 105                 110

Ile Arg Ser Tyr Glu Val Gly Pro Asp Arg Ser Thr Ser Ile Val Ala
        115                 120                 125

Val Met Asn His Leu Gln Glu Ala Ala Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Ile Trp Val Val Lys Arg Thr His Val Ala Val Glu Arg Tyr
                165                 170                 175

Pro Ala Trp Gly Asp Thr Val Glu Val Glu Cys Trp Val Gly Ala Ser
            180                 185                 190

Gly Asn Asn Gly Arg Arg His Asp Phe Leu Val Arg Asp Cys Lys Thr
        195                 200                 205

Gly Glu Ile Leu Thr Arg Cys Thr Ser Leu Ser Val Met Met Asn Thr
    210                 215                 220

Arg Thr Arg Arg Leu Ser Lys Ile Pro Glu Glu Val Arg Gly Glu Ile
225                 230                 235                 240

Gly Pro Ala Phe Ile Asp Asn Val Ala Val Lys Asp Glu Glu Ile Lys
                245                 250                 255
```

```
Lys Pro Gln Lys Leu Asn Asp Ser Thr Ala Asp Tyr Ile Gln Gly Gly
            260                 265                 270

Leu Thr Pro Arg Trp Asn Asp Leu Asp Ile Asn Gln His Val Asn Asn
        275                 280                 285

Ile Lys Tyr Val Asp Trp Ile Leu Glu Thr Val Pro Asp Ser Ile Phe
    290                 295                 300

Glu Ser His His Ile Ser Ser Phe Thr Ile Glu Tyr Arg Arg Glu Cys
305                 310                 315                 320

Thr Met Asp Ser Val Leu Gln Ser Leu Thr Thr Val Ser Gly Gly Ser
                325                 330                 335

Ser Glu Ala Gly Leu Val Cys Glu His Leu Leu Gln Leu Glu Gly Gly
            340                 345                 350

Ser Glu Val Leu Arg Ala Lys Thr Glu Trp Arg Pro Lys Leu Thr Asp
        355                 360                 365

Ser Phe Arg Gly Ile Ser Val Ile Pro Ala Glu Ser Ser Val
    370                 375                 380

<210> SEQ ID NO 41
<211> LENGTH: 627
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(627)
<223> OTHER INFORMATION: Y.lipolytica codon-optimized nucleotide
      sequence of thioesterase from Escherichia coli TesA, without the
      leader sequence, named TesA(LL)

<400> SEQUENCE: 41
atgatgaact tcaacaacgt gttccgatgg catctgccct ttctgtttct ggtgctgctg      60
accttccgag ccgccgctgc tgacaccctg ctgatcctgg gcgactctct gtctgccggc     120
taccgaatgt ctgcctctgc cgcttggccc gctctgctga cgacaagtg gcagtctaag      180 acctctgtgg tgaacgcctc tatctctggc gacacctctc agcagggcct cgctcgactg     240
cctgctctgc tcaagcagca tcagccccga tgggtgctcg tcgagcttgg cggcaacgac     300
ggcctgcgag gcttccagcc tcagcagacc gagcagaccc tgcgacagat tctgcaggac     360
gtgaaggccg ccaacgctga gcctctgctg atgcagattc gactgcccgc caactacggc     420
cgacgataca cgaggccctt ctctgctatc taccccaagc tggccaagga attcgacgtg     480
cccctgctgc cattcttcat ggaagaggtg tacctgaagc tcagtggat gcaggacgac      540 ggcattcacc ccaaccgaga tgctcagccc ttcattgccg actggatggc caagcagctg     600
cagcctctgg tgaaccacga ctcttaa                                         627

<210> SEQ ID NO 42
<211> LENGTH: 208
<212> TYPE: PRT
<213> ORGANISM: Escherichia coli
<220> FEATURE:
<221> NAME/KEY: MISC_FEATURE
<222> LOCATION: (1)..(208)
<223> OTHER INFORMATION: protein sequence of thioesterase from
      Escherichia coli TesA, without the leader sequence, named TesA(LL)

<400> SEQUENCE: 42

Met Met Asn Phe Asn Asn Val Phe Arg Trp His Leu Pro Phe Leu Phe
1               5                   10                  15

Leu Val Leu Leu Thr Phe Arg Ala Ala Ala Ala Asp Thr Leu Leu Ile
```

```
                    20                  25                  30
Leu Gly Asp Ser Leu Ser Ala Gly Tyr Arg Met Ser Ala Ser Ala Ala
                35                  40                  45

Trp Pro Ala Leu Leu Asn Asp Lys Trp Gln Ser Lys Thr Ser Val Val
         50                  55                  60

Asn Ala Ser Ile Ser Gly Asp Thr Ser Gln Gln Gly Leu Ala Arg Leu
 65                  70                  75                  80

Pro Ala Leu Leu Lys Gln His Gln Pro Arg Trp Val Leu Val Glu Leu
                 85                  90                  95

Gly Gly Asn Asp Gly Leu Arg Gly Phe Gln Pro Gln Gln Thr Glu Gln
                100                 105                 110

Thr Leu Arg Gln Ile Leu Gln Asp Val Lys Ala Ala Asn Ala Glu Pro
            115                 120                 125

Leu Leu Met Gln Ile Arg Leu Pro Ala Asn Tyr Gly Arg Arg Tyr Asn
        130                 135                 140

Glu Ala Phe Ser Ala Ile Tyr Pro Lys Leu Ala Lys Glu Phe Asp Val
145                 150                 155                 160

Pro Leu Leu Pro Phe Phe Met Glu Glu Val Tyr Leu Lys Pro Gln Trp
                165                 170                 175

Met Gln Asp Asp Gly Ile His Pro Asn Arg Asp Ala Gln Pro Phe Ile
                180                 185                 190

Ala Asp Trp Met Ala Lys Gln Leu Gln Pro Leu Val Asn His Asp Ser
            195                 200                 205

<210> SEQ ID NO 43
<211> LENGTH: 1368
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1368)
<223> OTHER INFORMATION: Y.lipolytica codon-optimized nucleotide
      sequence of fatty acyl reductase from H. armigera Har_FAR

<400> SEQUENCE: 43
atggtggtcc tgacctctaa ggagactaag ccctccgtgg ccgagttcta cgctggcaag    60
tctgtcttca tcaccggcgg aaccggtttc ctgggcaagg tcttcattga aagctgctg   120 tactcctgtc ccgacatcgg caacatctac atgctgatcc gagagaagaa gggactgtct   180
gtgtccgagc gaattaagca cttcctggac gacccctgt tcacccgact gaaggagaag   240
cgacccgccg acctggagaa gatcgtgctg attcccggag acatcaccgc tcccgacctg   300
ggtattacct ctgagaacga aagatgctg atcgagaagg tgtctgtcat cattcactcc   360
gccgctaccg tcaagttcaa cgagcccctg cccaccgcct ggaagatcaa cgtggaggga   420
acccgaatga tgctggctct gtctcgacga atgaagcgaa ttgaggtctt catccacatt   480
tccaccgcct acaccaacac caaccgagag gtggtggacg atcctgta ccctgctcct   540 gctgacattg accaggtgca ccgatacgtc aaggacggta tctctgagga agagactgag   600
aagattctga acgccgacc caacacctac accttcacca aggccctgac cgagcacctg   660
gtggctgaga ccaggcttta cgtgcccacc atcattgtcc gaccctccgt ggtcgccgct   720
atcaaggacg agcccattaa gggatggctg ggtaactggt acggagctac cggactgacc   780
gtgttcaccg ctaagggtct gaaccgagtc atctacggcc actcttccaa catcgtggac   840
ctgattcccg tggactacgt cgccaacctg gtcattgccg ctggcgctaa gtcttccaag   900
```

| | | | |
|---|---|---|---|
| tccaccgagc | tgaaggtgta | caactgttgc tcttccgcct | gcaaccccat caccattgga | 960 |
| aagctgatgt | ctatgttcgc | cgaggacgct atcaagcaga | agtcctacgc tatgcccctg | 1020 |
| cccggttggt | acatcttcac | caagtacaag tggctggtcc | tgctgctgac cattctgttc | 1080 |
| caggtcatcc | ccgcctacat | taccgacctg taccgacacc | tgatcggcaa gaaccccga | 1140 |
| tacattaagc | tgcagtctct | ggtcaaccag acccgatctt | ccattgactt cttcacctct | 1200 |
| cactcctggg | tcatgaaggc | tgaccgagtc cgagagctgt | tcgcctctct gtccccgct | 1260 |
| gacaagtacc | tgttccctg | tgaccccacc gacatcaact | ggacccacta cattcaggac | 1320 |
| tactgctggg | gagtgcgaca | cttcctggag aagaagtcct | acgagtag | 1368 |

<210> SEQ ID NO 44
<211> LENGTH: 1437
<212> TYPE: DNA
<213> ORGANISM: Artificial Sequence
<220> FEATURE:
<223> OTHER INFORMATION: codon-optimized nucleotide sequence
<220> FEATURE:
<221> NAME/KEY: misc_feature
<222> LOCATION: (1)..(1437)
<223> OTHER INFORMATION: Y.lipolytica codon-optimized nucleotide
 sequence of fatty acyl reductase from Bicyclus anynana Ban-wFAR2

<400> SEQUENCE: 44

| | | | |
|---|---|---|---|
| atgtaccgaa | acgtgaacaa | caactacaag ggccactctg | tgtacaccaa cggcgctggc | 60 |
| tctcgagtga | agtctctgct | gtcctctgcc accgacaaca | ccaacgagta ccagtctatc | 120 |
| gccgagtgct | acaagggaca | gtccgtgttc atcaccggcg | gcaccggctt cgtcggcaag | 180 |
| gtgctgctcg | agaagctgct | gtactcttgc cccggcatcg | acaaggtgta cctgctggtg | 240 |
| cgagagactc | agggcgccac | cgctcaccag cgaatgcaga | agctcctgga agaacccgcc | 300 |
| ttctcgcgaa | tcaaggaaga | gaaccctcag gccttcgaga | aggtgatccc catcgtgggc | 360 |
| gacatcaccc | agcctcagct | gggcatcatg gccgagaacg | aggaactgct gattaaggaa | 420 |
| gtgtctttcg | tctaccacgt | ggccgccacc accaagttca | cgagactct ggacattgcc | 480 |
| atgaacgtga | acgtggccgg | aaccggacga gtgctggacc | tgtctaagcg aatggaaaac | 540 |
| atcaaggcct | tcgtgtacgt | gtctaccgcc tactctaaca | ccgaccgaga ggtggtggaa | 600 |
| gaggtgctgt | accccgctcc | tgtgtctctg aacgaggtgc | acaagctgct gaagatcggc | 660 |
| atcaccgacg | ctcaggtgaa | ggaactgatc aagggacgac | ccaacaccta cccttcacc | 720 |
| aaggctctgg | ctgagaacct | ggtggccgac aaccacggac | acgtgcccgc catcatcgtg | 780 |
| cgaccctcta | tcgtgtcctc | gtctaagaag gaacccatca | ccggatggat cgactcttgg | 840 |
| tacgcgcca | ccttcctggc | caccgtgacc atgaagggct | tcaaccgagt gttcgtgtcg | 900 |
| tcttacgagt | acaacctgga | cttcatcccc gtggactacg | tgtccaacct gatcatcgtg | 960 |
| gccgctgctc | gatgcaagtg | tctctgacaag gtggacgtgt | acaactcttc tacctccggc | 1020 |
| gaaaaccctc | tgaagattgg | cgccttcttc gacgacatca | ttgcctactc ttgcaagcac | 1080 |
| aagttctacg | acatccctct | gcctatggcc tacctgactc gataccgatg | ggtcatgttc | 1140 |
| ctgatcaccc | tgctgctgca | gaccctgcct gcctatatcg | ccgacctgtt cctgctgatc | 1200 |
| gtgggcaaga | agccccgata | cgtcaagctg gcctctaaga | tctctgccgc tcacgaggtc | 1260 |
| ctggactact | cccctctcg | aacctggtct atgtctgccc | gacagaccac cgctctgttc | 1320 |
| cagtctctgt | ctccctcgga | ccgagatcag tttccttgcg | accccaccga catcgactgg | 1380 |
| aaggagtaca | tcgtcaccta | ctgccaggga atccgacagt | tcctgtgcaa gtcttaa | 1437 |

<210> SEQ ID NO 45
<211> LENGTH: 478
<212> TYPE: PRT
<213> ORGANISM: Bicyclus anynana

<400> SEQUENCE: 45

Met Tyr Arg Asn Val Asn Asn Tyr Lys Gly His Ser Val Tyr Thr
1               5                   10                  15

Asn Gly Ala Gly Ser Arg Val Lys Ser Leu Leu Ser Ser Ala Thr Asp
            20                  25                  30

Asn Thr Asn Glu Tyr Gln Ser Ile Ala Glu Cys Tyr Lys Gly Gln Ser
        35                  40                  45

Val Phe Ile Thr Gly Gly Thr Gly Phe Val Gly Lys Val Leu Leu Glu
50                  55                  60

Lys Leu Leu Tyr Ser Cys Pro Gly Ile Asp Lys Val Tyr Leu Leu Val
65                  70                  75                  80

Arg Glu Thr Gln Gly Ala Thr Ala His Gln Arg Met Gln Lys Leu Leu
                85                  90                  95

Glu Glu Pro Ala Phe Ser Arg Ile Lys Glu Glu Asn Pro Gln Ala Phe
            100                 105                 110

Glu Lys Val Ile Pro Ile Val Gly Asp Ile Thr Gln Pro Gln Leu Gly
        115                 120                 125

Ile Met Ala Glu Asn Glu Glu Leu Leu Ile Lys Glu Val Ser Phe Val
130                 135                 140

Tyr His Val Ala Ala Thr Thr Lys Phe Asn Glu Thr Leu Asp Ile Ala
145                 150                 155                 160

Met Asn Val Asn Val Ala Gly Thr Gly Arg Val Leu Asp Leu Ser Lys
                165                 170                 175

Arg Met Glu Asn Ile Lys Ala Phe Val Tyr Val Ser Thr Ala Tyr Ser
            180                 185                 190

Asn Thr Asp Arg Glu Val Val Glu Glu Val Leu Tyr Pro Ala Pro Val
        195                 200                 205

Ser Leu Asn Glu Val His Lys Leu Leu Lys Ile Gly Ile Thr Asp Ala
210                 215                 220

Gln Val Lys Glu Leu Ile Lys Gly Arg Pro Asn Thr Tyr Thr Phe Thr
225                 230                 235                 240

Lys Ala Leu Ala Glu Asn Leu Val Ala Asp Asn His Gly His Val Pro
                245                 250                 255

Ala Ile Ile Val Arg Pro Ser Ile Val Ser Ser Ser Lys Lys Glu Pro
            260                 265                 270

Ile Thr Gly Trp Ile Asp Ser Trp Tyr Gly Ala Thr Phe Leu Ala Thr
        275                 280                 285

Val Thr Met Lys Gly Phe Asn Arg Val Phe Val Ser Ser Tyr Glu Tyr
290                 295                 300

Asn Leu Asp Phe Ile Pro Val Asp Val Ser Asn Leu Ile Ile Val
305                 310                 315                 320

Ala Ala Ala Arg Cys Lys Cys Ser Asp Lys Val Asp Val Tyr Asn Ser
                325                 330                 335

Ser Thr Ser Gly Glu Asn Pro Leu Lys Ile Gly Ala Phe Phe Asp Asp
            340                 345                 350

Ile Ile Ala Tyr Ser Cys Lys His Lys Phe Tyr Asp Ile Pro Leu Pro
        355                 360                 365

Met Ala Tyr Leu Thr Arg Tyr Arg Trp Val Met Phe Leu Ile Thr Leu

```
                370             375             380
Leu Leu Gln Thr Leu Pro Ala Tyr Ile Ala Asp Leu Phe Leu Leu Ile
385                 390                 395                 400

Val Gly Lys Lys Pro Arg Tyr Val Lys Leu Ala Ser Lys Ile Ser Ala
                405                 410                 415

Ala His Glu Val Leu Asp Tyr Phe Pro Ser Arg Thr Trp Ser Met Ser
            420                 425                 430

Ala Arg Gln Thr Thr Ala Leu Phe Gln Ser Leu Ser Pro Ser Asp Arg
        435                 440                 445

Asp Gln Phe Pro Cys Asp Pro Thr Asp Ile Asp Trp Lys Glu Tyr Ile
    450                 455                 460

Val Thr Tyr Cys Gln Gly Ile Arg Gln Phe Leu Cys Lys Ser
465                 470                 475
```

```
<210> SEQ ID NO 46
<211> LENGTH: 29
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(29)
<223> OTHER INFORMATION: PR-1852 (PTDH3_fw)
     n = uracil

<400> SEQUENCE: 46
cacgcganat aaaaaacacg cttttttcag                                    29

<210> SEQ ID NO 47
<211> LENGTH: 34
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(34)
<223> OTHER INFORMATION: pr-1853 (ptdh3_rv)
     n = uracil

<400> SEQUENCE: 47
acctgcacnt tgtttgttt atgtgtgttt attc                                34

<210> SEQ ID NO 48
<211> LENGTH: 26
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(26)
<223> OTHER INFORMATION: pr-1565 (ptef1)
     n = uracil

<400> SEQUENCE: 48
atgacagant tgtaattaaa acttag                                        26

<210> SEQ ID NO 49
<211> LENGTH: 37
<212> TYPE: DNA
<213> ORGANISM: Artificial Sequence
<220> FEATURE:
<223> OTHER INFORMATION: Primer sequence
<220> FEATURE:
```

```
<221> NAME/KEY: misc_feature
<222> LOCATION: (1)..(37)
<223> OTHER INFORMATION: pr-8332 (har_far_u1_fw)
      n = uracil

<400> SEQUENCE: 49
agtgcaggna aaacaatggt tgtcttgacc tccaaag                                37

<210> SEQ ID NO 50
<211> LENGTH: 43
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(43)
<223> OTHER INFORMATION: pr-10739 (har_far_hdel_u1_rev)
      n = uracil

<400> SEQUENCE: 50
cgtgcgantt acaattcatc atgttccaag aaatgtctaa cac                         43

<210> SEQ ID NO 51
<211> LENGTH: 33
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(33)
<223> OTHER INFORMATION: pr-14318 (phd9_u2_fw)
      n = uracil

<400> SEQUENCE: 51
atctgtcana aaacaatggg cgtcctgctg aac                                    33

<210> SEQ ID NO 52
<211> LENGTH: 21
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(21)
<223> OTHER INFORMATION: PR-14276 (Phd9_U2_rev)
      n = uracil

<400> SEQUENCE: 52
cacgcgantt agacctttcg g                                                 21

<210> SEQ ID NO 53
<211> LENGTH: 27
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(27)
<223> OTHER INFORMATION: pr-14319 (rcd9_u2_fw)
      n = uracil

<400> SEQUENCE: 53
atctgtcana aaacaatggc cctgaag                                           27

<210> SEQ ID NO 54
```

```
<211> LENGTH: 23
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(23)
<223> OTHER INFORMATION: pr-14278 (rcd9_u2_rev)
<220> FEATURE:
<221> NAME/KEY: misc_feature
<222> LOCATION: (1)..(23)
<223> OTHER INFORMATION: pr-14278 (rcd9_u2_rev)
      n = uracil

<400> SEQUENCE: 54
cacgcgantt acagcttcac ctg                                      23

<210> SEQ ID NO 55
<211> LENGTH: 33
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(33)
<223> OTHER INFORMATION: pr-14320 (atf1_u2_fw)
      n = uracil

<400> SEQUENCE: 55
atctgtcana aaacaatgaa tgaaatcgat gag                            33

<210> SEQ ID NO 56
<211> LENGTH: 33
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(33)
<223> OTHER INFORMATION: pr-14321 (atf1_u2_rev)
      n = uracil

<400> SEQUENCE: 56
cacgcganct aagggcctaa aaggagagct ttg                            33

<210> SEQ ID NO 57
<211> LENGTH: 36
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(36)
<223> OTHER INFORMATION: pr-15974 (dmd9_u1_fw)
      n = uracil

<400> SEQUENCE: 57
agtgcaggna aaacaatggc tccatactct agaatc                         36

<210> SEQ ID NO 58
<211> LENGTH: 27
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
```

```
<222> LOCATION: (1)..(27)
<223> OTHER INFORMATION: pr-15975 (dmd9_u1_rev)
      n = uracil

<400> SEQUENCE: 58
cgtgcgantt atctggactt gtcaacc                                        27

<210> SEQ ID NO 59
<211> LENGTH: 53
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(53)
<223> OTHER INFORMATION: pr-15976 (attb1_dmd9_f)

<400> SEQUENCE: 59
ggggacaagt ttgtacaaaa aagcaggcta tggctccata ctctagaatc tac           53

<210> SEQ ID NO 60
<211> LENGTH: 64
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(64)
<223> OTHER INFORMATION: pr-15977 (attb2_dmd9_r)

<400> SEQUENCE: 60
ggggaccact ttgtacaaga aagctgggtt tatctggact tgtcaaccaa caaaacgttt    60
ctag                                                                 64

<210> SEQ ID NO 61
<211> LENGTH: 53
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(53)
<223> OTHER INFORMATION: pr-15978 (attb1_phd9_f)

<400> SEQUENCE: 61
ggggacaagt ttgtacaaaa aagcaggcta tggccctgaa gctgaacccc ttc           53

<210> SEQ ID NO 62
<211> LENGTH: 54
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(54)
<223> OTHER INFORMATION: pr-15979 (attb2_phd9_r)

<400> SEQUENCE: 62
ggggaccact ttgtacaaga aagctgggtt tacagcttca cctgtcggtc gaag          54

<210> SEQ ID NO 63
<211> LENGTH: 52
<212> TYPE: DNA
<213> ORGANISM: Artificial Sequence
```

-continued

```
<220> FEATURE:
<223> OTHER INFORMATION: Primer sequence
<220> FEATURE:
<221> NAME/KEY: misc_feature
<222> LOCATION: (1)..(52)
<223> OTHER INFORMATION: pr-15980 (attb1_rcd9_f)

<400> SEQUENCE: 63
ggggacaagt ttgtacaaaa aagcaggcta tgggcgtcct gctgaacatc tg          52

<210> SEQ ID NO 64
<211> LENGTH: 53
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(53)
<223> OTHER INFORMATION: pr-15981 (attb1_rcd9_r)

<400> SEQUENCE: 64
ggggaccact ttgtacaaga aagctgggtt tagacctttc ggtcgaagat cca         53

<210> SEQ ID NO 65
<211> LENGTH: 335
<212> TYPE: PRT
<213> ORGANISM: Choristoneura rosaceana

<400> SEQUENCE: 65
```

Met Ala Pro Asn Val Glu Asp Met Glu Ser Asp Leu Pro Glu Ser Glu
1               5                   10                  15

Glu Lys Leu Glu Lys Leu Val Ala Pro Gln Ala Ala Pro Arg Lys Tyr
                20                  25                  30

Gln Ile Ile Tyr Thr Asn Leu Leu Thr Phe Gly Tyr Trp His Ile Ala
            35                  40                  45

Gly Leu Tyr Gly Leu Tyr Leu Cys Phe Thr Ser Ala Lys Trp Gln Thr
        50                  55                  60

Ile Ile Leu Ala Leu Ile Leu Asn Glu Met Ala Ile Leu Gly Ile Thr
65                  70                  75                  80

Ala Gly Ala His Arg Leu Trp Ala His Arg Ser Tyr Lys Ala Thr Val
                85                  90                  95

Pro Leu Gln Ile Ile Leu Ile Ile Phe Asn Ser Leu Ser Phe Gln Asn
            100                 105                 110

Ser Ala Ile His Trp Ile Arg Asp His Arg Met His His Lys Tyr Ser
        115                 120                 125

Asp Thr Asp Gly Asp Pro His Asn Ala Ser Arg Gly Phe Phe Tyr Ser
    130                 135                 140

His Val Gly Trp Leu Leu Val Lys Lys His Pro Glu Val Lys Lys Arg
145                 150                 155                 160

Ala Lys Thr Ile Asp Met Ser Asp Ile Tyr Ser Asn Pro Ile Leu Arg
                165                 170                 175

Phe Gln Lys Lys Tyr Ala Ile Pro Phe Ile Gly Met Ile Cys Phe Val
            180                 185                 190

Leu Pro Thr Ile Ile Pro Met Tyr Phe Trp Gly Glu Thr Leu Ser Asn
        195                 200                 205

Ala Trp His Ile Thr Met Leu Arg Tyr Val Phe Ser Leu Asn Ser Ile
    210                 215                 220

Phe Leu Val Asn Ser Ala Ala His Leu Tyr Gly Tyr Arg Pro Tyr Asp
225                 230                 235                 240

```
Lys Asn Ile Leu Pro Ala Glu Asn Lys Met Thr Phe Ile Ala Cys Leu
                245                 250                 255

Gly Glu Asn Phe His Asn Tyr His His Val Phe Pro Trp Asp Tyr Arg
            260                 265                 270

Ala Ser Glu Leu Gly Asn Ile Gly Met Asn Trp Thr Ala Lys Phe Ile
        275                 280                 285

Asp Phe Phe Ala Trp Ile Gly Trp Ala Tyr Asp Leu Lys Thr Ala Ser
    290                 295                 300

Asp Glu Asn Ile Lys Ser Arg Met Lys Arg Thr Gly Asp Gly Thr Asp
305                 310                 315                 320

Val Ser Gly Gln Lys Tyr Ser Cys Glu Ser Ser Glu Val Leu Gln
                325                 330                 335

<210> SEQ ID NO 66
<211> LENGTH: 334
<212> TYPE: PRT
<213> ORGANISM: Choristoneura parallela

<400> SEQUENCE: 66

Met Ala Pro Asn Val Glu Asp Met Gly Ser Asp Met Pro Gly Ser Glu
1               5                   10                  15

Lys Trp Glu Lys Leu Val Ala Pro Gln Ala Ala Pro Arg Lys Tyr Glu
                20                  25                  30

Ile Ile Tyr Thr Asn Leu Leu Thr Phe Gly Tyr Gly His Ile Ala Gly
            35                  40                  45

Leu Tyr Gly Leu Tyr Leu Cys Phe Thr Ser Ala Lys Trp Gln Thr Val
    50                  55                  60

Ile Leu Ala Ile Ile Leu Asn Glu Met Ala Ile Leu Gly Ile Thr Ala
65                  70                  75                  80

Gly Ala His Arg Leu Trp Ser His Arg Ser Tyr Lys Ala Ala Val Pro
                85                  90                  95

Leu Gln Ile Ile Leu Met Ile Phe Asn Ser Leu Ala Phe Gln Asn Ser
            100                 105                 110

Ala Ile Asn Trp Val Arg Asp His Arg Met His His Lys Tyr Ser Asp
        115                 120                 125

Thr Asp Gly Asp Pro His Asn Ala Ser Arg Gly Phe Phe Tyr Ser His
    130                 135                 140

Val Gly Trp Leu Leu Val Lys Lys His Pro Glu Val Lys Lys Arg Gly
145                 150                 155                 160

Lys Met Ile Asp Met Ser Asp Ile Tyr Ser Asn Pro Val Leu Arg Phe
                165                 170                 175

Gln Lys Lys Tyr Ala Ile Pro Phe Ile Gly Met Ile Cys Phe Val Leu
            180                 185                 190

Pro Thr Ile Ile Pro Met Tyr Phe Trp Gly Glu Thr Leu Ser Asn Ala
        195                 200                 205

Trp His Ile Thr Met Leu Arg Tyr Val Phe Ser Leu Asn Ser Ile Phe
    210                 215                 220

Leu Val Asn Ser Ala Ala His Leu Tyr Gly Tyr Arg Pro Tyr Asp Lys
225                 230                 235                 240

Asn Ile Leu Pro Ala Glu Asn Lys Ile Ala Leu Ile Ala Cys Leu Gly
                245                 250                 255

Asp Ser Phe His Asn Tyr His His Val Phe Pro Trp Asp Tyr Arg Ala
            260                 265                 270

Ser Glu Leu Gly Asn Ile Gly Met Asn Trp Thr Ala Gln Phe Ile Asp
```

```
                275                 280                 285
Phe Phe Ala Trp Ile Gly Trp Ala Tyr Asp Leu Lys Thr Ala Ser Asp
        290                 295                 300

Glu Asn Ile Asn Ser Arg Met Lys Arg Thr Gly Asp Gly Thr Asp Ile
305                 310                 315                 320

Ser Gly Gln Lys Tyr Ser Cys Glu Ser Ser Glu Val Leu Gln
                325                 330

<210> SEQ ID NO 67
<211> LENGTH: 981
<212> TYPE: DNA
<213> ORGANISM: Artificial Sequence
<220> FEATURE:
<223> OTHER INFORMATION: Artificial sequence
<220> FEATURE:
<221> NAME/KEY: CDS
<222> LOCATION: (1)..(981)
<223> OTHER INFORMATION: codon-optimised for Y. lipolytica

<400> SEQUENCE: 67 atg gtg ccc aac aag ggt tct tcc gac gtc ctg tct gag cac tcc gag      48
Met Val Pro Asn Lys Gly Ser Ser Asp Val Leu Ser Glu His Ser Glu
1               5                   10                  15 ccc cag ttc acc aag ctg att gct ccc cag gct ggc ccc cga aag tac      96
Pro Gln Phe Thr Lys Leu Ile Ala Pro Gln Ala Gly Pro Arg Lys Tyr
                20                  25                  30 aag atc gtg tac cga aac ctg ctg acc ttc gga tac tgg cac ctg tct     144
Lys Ile Val Tyr Arg Asn Leu Leu Thr Phe Gly Tyr Trp His Leu Ser
            35                  40                  45 gcc gtc tac ggt ctg tac ctg tgt ttc acc tgc gcc aag tgg gct acc     192
Ala Val Tyr Gly Leu Tyr Leu Cys Phe Thr Cys Ala Lys Trp Ala Thr
        50                  55                  60 att ctg ttc gcc ttc ttc ctg tac gtg atc gct gag atc ggc att acc     240
Ile Leu Phe Ala Phe Phe Leu Tyr Val Ile Ala Glu Ile Gly Ile Thr
65              70                  75                  80 ggc gga gcc cac cga ctg tgg gct cac cga acc tac aag gcc aag ctg     288
Gly Gly Ala His Arg Leu Trp Ala His Arg Thr Tyr Lys Ala Lys Leu
                85                  90                  95 ccc ctg gag atc ctg ctg ctg att atg aac tct atc gct ttc cag gac     336
Pro Leu Glu Ile Leu Leu Leu Ile Met Asn Ser Ile Ala Phe Gln Asp
                100                 105                 110 acc gcc ttc acc tgg gct cga gat cac cga ctg cac cac aag tac tct     384
Thr Ala Phe Thr Trp Ala Arg Asp His Arg Leu His His Lys Tyr Ser
            115                 120                 125 gac acc gac gct gac cct cac aac gct acc cga ggt ttc ttc tac tcc     432
Asp Thr Asp Ala Asp Pro His Asn Ala Thr Arg Gly Phe Phe Tyr Ser
        130                 135                 140 cac gtg ggc tgg ctg ctg gtc aag aag cac ccc gag gtg aag gcc cgg     480
His Val Gly Trp Leu Leu Val Lys Lys His Pro Glu Val Lys Ala Arg
145                 150                 155                 160 gga aag tac ctg tcc ctg gac gac ctg aag aac aac ccc ctg ctg aag     528
Gly Lys Tyr Leu Ser Leu Asp Asp Leu Lys Asn Asn Pro Leu Leu Lys
                165                 170                 175 ttc cag aag aag tac gct atc ctg gtc att ggc acc ctg tgt ttc ctg     576
Phe Gln Lys Lys Tyr Ala Ile Leu Val Ile Gly Thr Leu Cys Phe Leu
            180                 185                 190 atg ccc acc ttc gtg ccc gtc tac ttc tgg ggt gag ggc att tct acc     624
Met Pro Thr Phe Val Pro Val Tyr Phe Trp Gly Glu Gly Ile Ser Thr
        195                 200                 205 gcc tgg aac atc aac ctg ctg cga tac gtg atg aac ctg aac atg acc     672
Ala Trp Asn Ile Asn Leu Leu Arg Tyr Val Met Asn Leu Asn Met Thr
```

```
                       210                 215                 220
ttc ctg gtc aac tcc gcc gct cac att ttc ggc aac aag ccc tac gac        720
Phe Leu Val Asn Ser Ala Ala His Ile Phe Gly Asn Lys Pro Tyr Asp
225                 230                 235                 240 aag tct att gcc tcc gtg cag aac atc tct gtc tcc ctg gct acc ttc        768
Lys Ser Ile Ala Ser Val Gln Asn Ile Ser Val Ser Leu Ala Thr Phe
                245                 250                 255 gga gag ggt ttc cac aac tac cac cac acc tac cct tgg gac tac cga        816
Gly Glu Gly Phe His Asn Tyr His His Thr Tyr Pro Trp Asp Tyr Arg
            260                 265                 270 gct gct gag ctg ggc aac aac cga ctg aac atg acc acc gcc ttc att        864
Ala Ala Glu Leu Gly Asn Asn Arg Leu Asn Met Thr Thr Ala Phe Ile
        275                 280                 285 gac ttc ttc gcc tgg atc gga tgg gct tac gac ctg aag tcc gtc ccc        912
Asp Phe Phe Ala Trp Ile Gly Trp Ala Tyr Asp Leu Lys Ser Val Pro
    290                 295                 300 cag gaa gcc atc gct aag cga tgc gct aag acc ggc gac gga acc gac        960
Gln Glu Ala Ile Ala Lys Arg Cys Ala Lys Thr Gly Asp Gly Thr Asp
305                 310                 315                 320 atg tgg gga cga aag cga tag                                            981
Met Trp Gly Arg Lys Arg
                325

<210> SEQ ID NO 68
<211> LENGTH: 326
<212> TYPE: PRT
<213> ORGANISM: Artificial Sequence
<220> FEATURE:
<223> OTHER INFORMATION: Synthetic Construct

<400> SEQUENCE: 68

Met Val Pro Asn Lys Gly Ser Ser Asp Val Leu Ser Glu His Ser Glu
1               5                   10                  15

Pro Gln Phe Thr Lys Leu Ile Ala Pro Gln Ala Gly Pro Arg Lys Tyr
            20                  25                  30

Lys Ile Val Tyr Arg Asn Leu Leu Thr Phe Gly Tyr Trp His Leu Ser
        35                  40                  45

Ala Val Tyr Gly Leu Tyr Leu Cys Phe Thr Cys Ala Lys Trp Ala Thr
    50                  55                  60

Ile Leu Phe Ala Phe Phe Leu Tyr Val Ile Ala Glu Ile Gly Ile Thr
65                  70                  75                  80

Gly Gly Ala His Arg Leu Trp Ala His Arg Thr Tyr Lys Ala Lys Leu
                85                  90                  95

Pro Leu Glu Ile Leu Leu Leu Ile Met Asn Ser Ile Ala Phe Gln Asp
            100                 105                 110

Thr Ala Phe Thr Trp Ala Arg Asp His Arg Leu His His Lys Tyr Ser
        115                 120                 125

Asp Thr Asp Ala Asp Pro His Asn Ala Thr Arg Gly Phe Phe Tyr Ser
    130                 135                 140

His Val Gly Trp Leu Leu Val Lys Lys His Pro Glu Val Lys Ala Arg
145                 150                 155                 160

Gly Lys Tyr Leu Ser Leu Asp Asp Leu Lys Asn Asn Pro Leu Leu Lys
                165                 170                 175

Phe Gln Lys Lys Tyr Ala Ile Leu Val Ile Gly Thr Leu Cys Phe Leu
            180                 185                 190

Met Pro Thr Phe Val Pro Val Tyr Phe Trp Gly Glu Gly Ile Ser Thr
        195                 200                 205
```

| | | | | | | | | | | | | |
|---|---|---|---|---|---|---|---|---|---|---|---|---|
| Ala | Trp | Asn | Ile | Asn | Leu | Leu | Arg | Tyr | Val | Met | Asn | Leu | Asn | Met | Thr |
| | 210 | | | | 215 | | | | | 220 | | |

Phe Leu Val Asn Ser Ala Ala His Ile Phe Gly Asn Lys Pro Tyr Asp
225                 230                 235                 240

Lys Ser Ile Ala Ser Val Gln Asn Ile Ser Val Ser Leu Ala Thr Phe
            245                 250                 255

Gly Glu Gly Phe His Asn Tyr His His Thr Tyr Pro Trp Asp Tyr Arg
        260                 265                 270

Ala Ala Glu Leu Gly Asn Asn Arg Leu Asn Met Thr Thr Ala Phe Ile
            275                 280                 285

Asp Phe Phe Ala Trp Ile Gly Trp Ala Tyr Asp Leu Lys Ser Val Pro
290                 295                 300

Gln Glu Ala Ile Ala Lys Arg Cys Ala Lys Thr Gly Asp Gly Thr Asp
305                 310                 315                 320

Met Trp Gly Arg Lys Arg
            325

```
<210> SEQ ID NO 69
<211> LENGTH: 1368
<212> TYPE: DNA
<213> ORGANISM: Artificial Sequence
<220> FEATURE:
<223> OTHER INFORMATION: Artificial sequence
<220> FEATURE:
<221> NAME/KEY: misc_feature
<222> LOCATION: (1)..(1368)
<223> OTHER INFORMATION: Y. lipolytica codon-optimized nucleotide
      sequence of Helicoverpa armigera fatty acyl reductase

<400> SEQUENCE: 69
atggtggtcc tgacctctaa ggagactaag ccctccgtgg ccgagttcta cgctggcaag      60
tctgtcttca tcaccggcgg aaccggtttc ctgggcaagg tcttcattga agagctgctg     120
tactcctgtc ccgacatcgg caacatctac atgctgatcc gagagaagaa gggactgtct     180
gtgtccgagc gaattaagca cttcctggac gaccccctgt tcacccgact gaaggagaag     240
cgacccgccg acctggagaa gatcgtgctg attcccggag acatcaccgc tcccgacctg     300
ggtattacct ctgagaacga aagatgctg atcgagaagg tgtctgtcat cattcactcc      360
gccgctaccg tcaagttcaa cgagcccctg cccaccgcct ggaagatcaa cgtggaggga     420
acccgaatga tgctggctct gtctcgacga atgaagcgaa ttgaggtctt catccacatt     480
tccaccgcct acaccaacac caaccgagag gtggtggacg agatcctgta ccctgctcct     540
gctgacattg accaggtgca ccgatacgtc aaggacggta tctctgagga agagactgag     600
aagattctga acggccgacc caacacctac accttcacca aggccctgac cgagcacctg     660
gtggctgaga accaggctta cgtgcccacc atcattgtcc gaccctccgt ggtcgccgct     720
atcaaggacg agcccattaa gggatggctg gtaactggt acggagctac cggactgacc      780
gtgttcaccg ctaagggtct gaaccgagtc atctacggcc actcttccaa catcgtggac     840
ctgattcccg tggactacgt cgccaacctg gtcattgccg ctggcgctaa gtcttccaag     900
tccaccgagc tgaaggtgta caactgttgc tcttccgcct gcaacccat caccattgga     960 aagctgatgt ctatgttcgc cgaggacgct atcaagcaga gtcctacgc tatgccctg      1020 cccggttggt acatcttcac caagtacaag tggctggtcc tgctgctgac cattctgttc     1080
caggtcatcc ccgcctacat taccgacctg taccgacacc tgatcggcaa gaaccccga     1140 tacattaagc tgcagtctct ggtcaaccag acccgatctt ccattgactt cttcacctct     1200
```

```
cactcctggg tcatgaaggc tgaccgagtc cgagagctgt tcgcctctct gtccccgct    1260 gacaagtacc tgttccctg tgaccccacc gacatcaact ggacccacta cattcaggac    1320
tactgctggg gagtgcgaca cttcctggag aagaagtcct acgagtag                1368
```

<210> SEQ ID NO 70
<211> LENGTH: 1362
<212> TYPE: DNA
<213> ORGANISM: Artificial Sequence
<220> FEATURE:
<223> OTHER INFORMATION: Artificial sequence
<220> FEATURE:
<221> NAME/KEY: misc_feature
<222> LOCATION: (1)..(1362)
<223> OTHER INFORMATION: S. cerevisiae codon-optimized nucleotide
      sequence of Heliothis subflexa fatty acyl reductase

<400> SEQUENCE: 70

```
atggttgtct tgacctccaa agaaactaag ccatctgttg ctgaattta cgctggtaag     60 tctgttttca ttactggtgg tactggtttc ttgggtaagg ttttcattga aaagttgttg   120
tactcctgcc cagatatcgg taatatctac atgttgatca gagaaaagaa gggtttgtcc   180
gtttccgaaa gaatcaagca ctttttggat gatccttttgt tcaccagatt gaaagaaaaa   240
agaccagccg acttggaaaa gatcgttttg attccaggtg atattactgc tccagatttg   300
ggtattacct ccgaaaacga aaagatgttg atcgaaaagg tcagtgtcat tattcattct   360
gctgctaccg ttaagttcaa cgaaccattg ccaactgctt ggaagattaa cgttgaaggt   420
actagaatga tgtggccttt gtctagaaga atgaagagaa tcgaagtttt catccatatc   480
tctaccgctt acactaacac caacagagaa gttgttgacg aaatcttgta tccagctcca   540
gctgatattg atcaagttca ccaatatgtt aaggacggta tctctgaaga agaaaactgaa  600 aaaatcttga acggtagacc aaaacacttac actttcacta aggctttgac cgaacatttg   660
gttgctgaaa atcaagctta cgttccaacc attatcgtta gaccatcagt tgttgctgcc   720
attaaggatg aacctattaa gggttggttg ggtaattggt atggtgctac aggtttgact   780 gttttttactg ctaagggttt gaacagagtt atctacggtc actcttctaa catcgttgat   840
ttgatcccag ttgattacgt tgccaacttg gttattgctc ctggtgctaa atcttctaag   900
tctactgaat tgaaggtcta caactgctgt tcttctgctt gtaacccaat tactatcggt   960
aagttgatgt ccatgtttgc tgaagatgct atcaagcaaa agtcttacgc tatgccattg  1020
ccaggttggt acatttttac taagtacaag tggttggtct tgttgttgac cattttgttc  1080
caagttattc cagcctacat taccgacttg tacagacatt tgattggtaa gaacccaaga  1140
tatatcaagt tgcaatcctt ggtcaatcaa accagatcct ccattgattt cttcaccaac  1200
cattcttggg ttatgaaggc tgatagagtc agagaattat tcgcttcttt gtctccagca  1260
gataagtact gtttccatg tgatccagtc aacatcaatt ggagacaata tatccaagat  1320
tactgctggg gtgttagaca tttcttggaa aaaaagactt aa                      1362
```

<210> SEQ ID NO 71
<211> LENGTH: 1850
<212> TYPE: PRT
<213> ORGANISM: Yarrowia lipolytica

<400> SEQUENCE: 71

```
Met His Pro Glu Val Glu Gln Glu Leu Ala His Val Leu Leu Thr Glu
1               5                   10                  15

Leu Leu Ala Tyr Gln Phe Ala Ser Pro Val Arg Trp Ile Glu Thr Gln
```

```
                20                  25                  30
Asp Val Leu Phe Lys Gln Phe Asn Val Glu Arg Val Glu Val Gly
         35                  40                  45
Pro Ser Pro Thr Leu Ala Gly Met Ala Gln Arg Thr Leu Lys Ser Lys
 50                  55                  60
Tyr Glu Ser Tyr Asp Ala Ala Leu Ser Leu Gln Arg Glu Ile Leu Cys
 65                  70                  75                  80
Tyr Ser Lys Asp Gln Lys Asp Ile Tyr Tyr Leu Ala Asp Glu Ala Asp
             85                  90                  95
Glu Ala Pro Ala Pro Ala Ala Gly Gly Asp Ala Pro Ala Ala Pro Ala
             100                 105                 110
Ala Ala Ala Pro Ala Ala Ala Ala Pro Ala Ala Ala Ala Pro
             115                 120                 125
Ser Gly Pro Val Ala Lys Val Glu Asp Ala Pro Val Lys Ala Gln Glu
         130                 135                 140
Ile Leu His Ala Leu Val Ala His Lys Leu Lys Lys Thr Pro Glu Gln
145                 150                 155                 160
Val Pro Leu Ser Lys Ala Ile Lys Asp Leu Val Gly Gly Lys Ser Thr
             165                 170                 175
Ile Gln Asn Glu Ile Leu Gly Asp Leu Gly Lys Glu Phe Gly Ala Thr
         180                 185                 190
Pro Glu Lys Pro Glu Asp Thr Pro Leu Gly Glu Leu Ala Glu Ser Phe
     195                 200                 205
Gln Ala Ser Phe Asp Gly Lys Leu Gly Lys Gln Ser Ser Ser Leu Ile
         210                 215                 220
Ala Arg Leu Met Ser Ser Lys Met Pro Gly Gly Phe Ser Leu Thr Ser
225                 230                 235                 240
Ala Arg Ser Tyr Leu Asp Ser Arg Trp Gly Leu Ala Ala Gly Arg Gln
             245                 250                 255
Asp Ser Val Leu Leu Val Ala Leu Met Asn Glu Pro Lys Asn Arg Leu
         260                 265                 270
Gly Ser Glu Ala Glu Ala Lys Ala Tyr Leu Asp Glu Gln Thr Gln Lys
         275                 280                 285
Tyr Ala Ala Ser Ala Gly Leu Asn Leu Ser Ala Pro Ala Gly Gly Ala
         290                 295                 300
Glu Gly Gly Asn Gly Gly Ala Val Ile Asp Ser Ala Ala Phe Asp
305                 310                 315                 320
Ala Leu Thr Lys Asp Gln Arg Tyr Leu Val Gln Gln Leu Glu Leu
             325                 330                 335
Phe Ala Asn Tyr Leu Lys Gln Asp Leu Arg Gln Gly Ser Lys Val Ala
             340                 345                 350
Ala Ala Gln Lys Glu Ala Met Asp Ile Leu Gln Ala Glu Leu Asp Leu
         355                 360                 365
Trp Asn Ser Glu His Gly Glu Val Tyr Ala Glu Gly Ile Lys Pro Ala
         370                 375                 380
Phe Ser Ala Leu Lys Ala Arg Val Tyr Asp Ser Tyr Trp Asn Trp Ala
385                 390                 395                 400
Arg Gln Asp Ser Leu Ser Met Tyr Phe Asp Ile Val Phe Gly Arg Leu
             405                 410                 415
Ser Thr Val Asp Arg Glu Ile Met Ala Lys Cys Ile His Leu Met Asn
             420                 425                 430
Arg Thr Asn His Asn Leu Ile Asp Tyr Met Gln Tyr His Met Asp His
             435                 440                 445
```

```
Val Pro Val His Lys Gly Ala Thr Tyr Glu Leu Ala Lys Gln Leu Gly
    450                 455                 460
Leu Gln Leu Leu Glu Asn Cys Lys Glu Thr Leu Thr Glu Ala Pro Val
465                 470                 475                 480
Tyr Lys Asp Val Ser Tyr Pro Thr Gly Pro Gln Thr Thr Ile Asp Val
                485                 490                 495
Lys Gly Asn Ile Val Tyr Asn Glu Val Pro Arg Pro Asn Val Arg Lys
                500                 505                 510
Leu Glu Gln Tyr Val His Glu Met Ala Cys Gly Gly Glu Leu Thr Lys
                515                 520                 525
Asp Pro Ser Phe Val Gly Glu Gly Val Gln Gly Glu Leu Lys Lys Leu
    530                 535                 540
Tyr Ser Gln Ile Ser Ala Leu Ala Lys Thr Gln Thr Gly Ser Thr Leu
545                 550                 555                 560
Asp Ile Glu Ala Leu Tyr Ser Asp Leu Val Ala Lys Ile Ser Gln Ala
                565                 570                 575
Glu Asp Ala Ser Lys Pro Val Val Glu Asn Lys Ala Val Ser Ala Ser
                580                 585                 590
Ile Thr Pro Gly Thr Leu Pro Phe Leu His Ile Lys Lys Lys Thr Glu
    595                 600                 605
Leu Gly Ala Trp Asn Tyr Asp Ser Glu Thr Thr Ala Thr Tyr Leu Asp
    610                 615                 620
Gly Leu Glu Val Ala Ala Arg Asp Gly Leu Thr Phe Gln Gly Lys Thr
625                 630                 635                 640
Ala Leu Ile Thr Gly Ala Gly Ala Gly Ser Ile Gly Ala Ser Ile Leu
                645                 650                 655
Gln Gly Leu Ile Ser Gly Gly Cys Lys Val Ile Val Thr Thr Ser Arg
                660                 665                 670
Tyr Ser Arg Lys Val Thr Glu Tyr Tyr Gln Ser Leu Tyr Thr Lys Phe
    675                 680                 685
Gly Ala Lys Gly Ser Thr Leu Ile Val Val Pro Phe Asn Gln Gly Ser
    690                 695                 700
Lys Lys Asp Val Asp Glu Leu Val Ser Phe Ile Tyr Asn Asp Pro Lys
705                 710                 715                 720
Asn Gly Gly Leu Gly Trp Asp Leu Asp Phe Val Val Pro Phe Ala Ala
                725                 730                 735
Leu Pro Glu Asn Gly Ile Glu Leu Glu His Ile Asp Ser Lys Ser Glu
                740                 745                 750
Leu Ala His Arg Ile Met Leu Thr Asn Leu Leu Arg Leu Leu Gly Asn
    755                 760                 765
Val Lys Lys Gln Lys Val Ala His Ser Tyr Glu Thr Arg Pro Ala Gln
    770                 775                 780
Val Met Leu Pro Leu Ser Pro Asn His Gly Asn Phe Gly Ser Asp Gly
785                 790                 795                 800
Leu Tyr Ser Glu Ser Lys Ile Ser Leu Glu Thr Leu Phe Asn Arg Trp
                805                 810                 815
His Thr Glu Ser Trp Gly Ser Tyr Leu Thr Ile Val Gly Val Val Ile
                820                 825                 830
Gly Trp Thr Arg Gly Thr Gly Leu Met Ser Ala Asn Asn Ile Thr Ala
    835                 840                 845
Glu Gly Leu Glu Gln Leu Gly Val Arg Thr Phe Ser Gln Thr Glu Met
    850                 855                 860
```

```
Ala Phe Ser Ile Met Gly Leu Met Thr Lys Asp Ile Val Arg Leu Ala
865                 870                 875                 880

Gln Asn Ser Pro Val Trp Ala Asp Leu Asn Gly Gly Phe Gln Tyr Ile
            885                 890                 895

Pro Asp Leu Lys Gly Val Val Gly Lys Ile Arg Arg Asp Ile Val Glu
        900                 905                 910

Thr Ser Glu Ile Arg Arg Ala Val Ala Gln Glu Thr Ala Ile Glu Gln
            915                 920                 925

Lys Val Val Asn Gly Pro His Ala Asp Leu Pro Tyr Gln Lys Val Glu
        930                 935                 940

Val Lys Pro Arg Ala Asn Leu Lys Phe Asp Phe Pro Thr Leu Lys Ser
945                 950                 955                 960

Tyr Ala Glu Val Lys Glu Leu Ser Pro Ala Gly Asp Ala Leu Glu Gly
            965                 970                 975

Leu Leu Asp Leu Ser Ser Val Ile Val Val Thr Gly Phe Ala Glu Val
        980                 985                 990

Gly Pro Trp Gly Asn Ala Arg Thr Arg Trp Asp Met Glu Ala Asn Gly
        995                 1000                1005

Val Phe Ser Leu Glu Gly Ala Ile Glu Met Ala Trp Ile Met Gly
    1010                1015                1020

Leu Ile Lys His His Asn Gly Pro Leu Pro Gly Met Pro Gln Tyr
    1025                1030                1035

Ser Gly Trp Ile Asp Thr Lys Thr Lys Gln Pro Val Asp Asp Arg
    1040                1045                1050

Asp Ile Lys Thr Lys Tyr Glu Asp Tyr Leu Leu Glu His Ala Gly
    1055                1060                1065

Ile Arg Leu Ile Glu Pro Glu Leu Phe His Gly Tyr Asn Pro Lys
    1070                1075                1080

Lys Lys Thr Phe Leu Gln Glu Val Ile Val Glu His Asp Leu Glu
    1085                1090                1095

Pro Phe Glu Ala Ser Lys Glu Ser Ala Glu Gln Phe Ala Leu Glu
    1100                1105                1110

Gln Gly Ala Asn Val Glu Ile Phe Ala Val Pro Glu Ser Asp Gln
    1115                1120                1125

Trp Thr Val Arg Leu Leu Lys Gly Ala Lys Leu Leu Ile Pro Lys
    1130                1135                1140

Ala Leu Lys Phe Asp Arg Leu Val Ala Gly Gln Ile Pro Thr Gly
    1145                1150                1155

Trp Asp Ala Arg Arg Tyr Gly Ile Pro Glu Asp Ile Cys Asp Gln
    1160                1165                1170

Val Asp Pro Ile Thr Leu Tyr Ala Leu Val Ser Thr Val Glu Ala
    1175                1180                1185

Leu Leu Ala Ser Gly Ile Thr Asp Pro Tyr Glu Phe Tyr Lys Tyr
    1190                1195                1200

Val His Val Ser Glu Val Gly Asn Cys Ser Gly Ser Gly Met Gly
    1205                1210                1215

Gly Ile Thr Ala Leu Arg Gly Met Phe Lys Asp Arg Phe Met Asp
    1220                1225                1230

Lys Pro Val Gln Asn Asp Ile Leu Gln Glu Ser Phe Ile Asn Thr
    1235                1240                1245

Met Ser Ala Trp Val Asn Met Leu Leu Leu Ser Ser Ser Gly Pro
    1250                1255                1260

Ile Lys Thr Pro Val Gly Ala Cys Ala Thr Ala Val Glu Ser Val
```

```
            1265                    1270                    1275

Asp Ile Gly Cys Glu Thr Ile Leu Ser Gly Lys Ala Arg Ile Cys
            1280                    1285                    1290

Leu Val Gly Gly Tyr Asp Asp Phe Gln Glu Glu Ser Ser Gln Glu
            1295                    1300                    1305

Phe Ala Asn Met Asn Ala Thr Ser Asn Ala Glu Thr Glu Ile Thr
            1310                    1315                    1320

His Gly Arg Thr Pro Ala Glu Met Ser Arg Pro Ile Thr Ser Thr
            1325                    1330                    1335

Arg Ala Gly Phe Met Glu Ala Gln Gly Ala Gly Thr Gln Val Leu
            1340                    1345                    1350

Met Ala Ala Asp Leu Ala Ile Ala Met Gly Val Pro Ile Tyr Cys
            1355                    1360                    1365

Ile Val Gly Tyr Val Asn Thr Ala Thr Asp Lys Ile Gly Arg Ser
            1370                    1375                    1380

Val Pro Ala Pro Gly Lys Gly Ile Leu Thr Thr Ala Arg Glu His
            1385                    1390                    1395

Gln Thr Leu Lys His Ala Asn Pro Leu Leu Asn Ile Lys Tyr Arg
            1400                    1405                    1410

Lys Arg Gln Leu Asp Ser Arg Leu Arg Asp Ile Lys Arg Trp Ala
            1415                    1420                    1425

Glu Gly Glu Met Glu Ala Ile Asp Ile Glu Leu Asp Asp Val Ser
            1430                    1435                    1440

Asp Ala Asp Lys Glu Ser Phe Ile Gln Glu Arg Ser Ala His Ile
            1445                    1450                    1455

Gln Ser Gln Ser Asp Arg Met Ile Arg Glu Ala Lys Asn Ser Trp
            1460                    1465                    1470

Gly Asn Ala Phe Phe Lys Gln Asp Ala Arg Ile Ser Pro Ile Arg
            1475                    1480                    1485

Gly Ala Leu Ala Thr Tyr Gly Leu Thr Ile Asp Asp Ile Ser Val
            1490                    1495                    1500

Ala Ser Phe His Gly Thr Ser Thr Lys Ala Asn Glu Lys Asn Glu
            1505                    1510                    1515

Thr Thr Thr Val Asn Ala Met Leu Glu His Leu Gly Arg Thr Arg
            1520                    1525                    1530

Gly Asn Pro Val Tyr Gly Ile Phe Gln Lys Tyr Leu Thr Gly His
            1535                    1540                    1545

Pro Lys Gly Ala Ala Gly Ala Trp Met Leu Asn Gly Ala Ile Gln
            1550                    1555                    1560

Cys Leu Asn Ser Gly Ile Ile Pro Gly Asn Arg Asn Ala Asp Asn
            1565                    1570                    1575

Val Asp Ala Tyr Phe Glu Gln Cys Gln His Val Val Phe Pro Ser
            1580                    1585                    1590

Arg Ser Leu Gln Thr Asp Gly Leu Lys Ala Ala Ser Val Thr Ser
            1595                    1600                    1605

Phe Gly Phe Gly Gln Lys Gly Ala Gln Ala Ile Val Ile His Pro
            1610                    1615                    1620

Asp Tyr Leu Tyr Ala Ala Leu Thr Pro Ser Glu Tyr Ser Glu Tyr
            1625                    1630                    1635

Thr Thr Arg Val Ala Gln Arg Tyr Lys Lys Ala Tyr Arg Tyr Tyr
            1640                    1645                    1650

His Asn Ala Ile Ala Glu Glu Ser Met Phe Gln Ala Lys Asp Lys
            1655                    1660                    1665
```

-continued

Ala Pro Tyr Ser Ala Glu Leu Glu Gln Glu Val Tyr Leu Asp Pro
    1670                1675                1680

Leu Val Arg Val His Gln Asn Glu Asp Thr Glu Gln Tyr Ser Phe
    1685                1690                1695

Asn Ala Lys Asp Leu Ala Ala Ser Ala Phe Val Lys Asn Ser His
    1700                1705                1710

Lys Asp Thr Ala Lys Val Leu Ala Asn Leu Thr Ser Gln Val Ser
    1715                1720                1725

Gly Ser Gly Lys Asn Val Gly Val Asp Val Glu Ala Ile Ser Ala
    1730                1735                1740

Ile Asn Ile Asp Asn Asp Thr Phe Leu Asp Arg Asn Phe Thr Ala
    1745                1750                1755

Asn Glu Gln Ala Tyr Cys Phe Lys Ala Pro Ser Pro Gln Ser Ser
    1760                1765                1770

Phe Ala Gly Thr Trp Ser Ala Lys Glu Ala Val Phe Lys Ser Leu
    1775                1780                1785

Gly Val Lys Ser Gln Gly Gly Gly Ala Glu Leu Lys Ser Ile Glu
    1790                1795                1800

Ile Thr Arg Asp Gly Asn Gly Ala Pro Val Val Val Leu His Gly
    1805                1810                1815

Ala Ala Lys Asp Ala Ala Ala Ser Lys Gly Ile Ser Thr Val Lys
    1820                1825                1830

Val Ser Ile Ser His Asp Asp Ser Gln Ala Val Ala Val Ala Val
    1835                1840                1845

Ala Glu
    1850

<210> SEQ ID NO 72
<211> LENGTH: 334
<212> TYPE: PRT
<213> ORGANISM: Yarrowia lipolytica

<400> SEQUENCE: 72

Met Lys Leu Ser Thr Ile Leu Phe Thr Ala Cys Ala Thr Leu Ala Ala
1               5                   10                  15

Ala Leu Pro Ser Pro Ile Thr Pro Ser Glu Ala Ala Val Leu Gln Lys
                20                  25                  30

Arg Val Tyr Thr Ser Thr Glu Thr Ser His Ile Asp Gln Glu Ser Tyr
            35                  40                  45

Asn Phe Phe Glu Lys Tyr Ala Arg Leu Ala Asn Ile Gly Tyr Cys Val
        50                  55                  60

Gly Pro Gly Thr Lys Ile Phe Lys Pro Phe Asn Cys Gly Leu Gln Cys
65                  70                  75                  80

Ala His Phe Pro Asn Val Glu Leu Ile Glu Glu Phe His Asp Pro Arg
                85                  90                  95

Leu Ile Phe Asp Val Ser Gly Tyr Leu Ala Val Asp His Ala Ser Lys
            100                 105                 110

Gln Ile Tyr Leu Val Ile Arg Gly Thr His Ser Leu Glu Asp Val Ile
        115                 120                 125

Thr Asp Ile Arg Ile Met Gln Ala Pro Leu Thr Asn Phe Asp Leu Ala
    130                 135                 140

Ala Asn Ile Ser Ser Thr Ala Thr Cys Asp Asp Cys Leu Val His Asn
145                 150                 155                 160

Gly Phe Ile Gln Ser Tyr Asn Asn Thr Tyr Asn Gln Ile Gly Pro Lys

```
            165                 170                 175
Leu Asp Ser Val Ile Glu Gln Tyr Pro Asp Tyr Gln Ile Ala Val Thr
            180                 185                 190

Gly His Ser Leu Gly Gly Ala Ala Leu Leu Phe Gly Ile Asn Leu
            195                 200                 205

Lys Val Asn Gly His Asp Pro Leu Val Val Thr Leu Gly Gln Pro Ile
            210                 215                 220

Val Gly Asn Ala Gly Phe Ala Asn Trp Val Asp Lys Leu Phe Phe Gly
225                 230                 235                 240

Gln Glu Asn Pro Asp Val Ser Lys Val Ser Lys Asp Arg Lys Leu Tyr
            245                 250                 255

Arg Ile Thr His Arg Gly Asp Ile Val Pro Gln Val Pro Phe Trp Asp
            260                 265                 270

Gly Tyr Gln His Cys Ser Gly Glu Val Phe Ile Asp Trp Pro Leu Ile
            275                 280                 285

His Pro Pro Leu Ser Asn Val Val Met Cys Gln Gly Gln Ser Asn Lys
            290                 295                 300

Gln Cys Ser Ala Gly Asn Thr Leu Leu Gln Gly Val Asn Val Ile Gly
305                 310                 315                 320

Asn His Leu Gln Tyr Phe Val Thr Glu Gly Val Cys Gly Ile
            325                 330

<210> SEQ ID NO 73
<211> LENGTH: 366
<212> TYPE: PRT
<213> ORGANISM: Yarrowia lipolytica

<400> SEQUENCE: 73

Met Val Ser Phe Gly Ala Arg Ile Lys Asp Phe Phe Ser Val Leu Leu
1               5                   10                  15

Phe Gly Ala Ala Ser Thr Ser Ser Ser Thr Lys Thr Ala Leu Val Ser
            20                  25                  30

Gln Gly Phe Tyr Asp Ala Ala Leu Asp Phe Ser His Leu Ser Asn Ile
            35                  40                  45

Ala Tyr Cys Val Asn Ala Pro Ile Thr Pro Leu Lys Ser Asp Phe Ser
        50                  55                  60

Cys Gly Gln Ser Cys Val His Phe Pro Asp Ile Glu Leu Val His Ile
65                  70                  75                  80

Phe Gly Gly Asp Phe Phe Ser Thr Ser Ile Thr Gly Tyr Leu Ala Leu
                85                  90                  95

Asp His Val Lys Lys Glu Lys Tyr Val Val Phe Arg Gly Thr Phe Ser
            100                 105                 110

Ile Ala Asp Ala Ile Thr Asp Ile Gln Phe Gln Gln Ser Ser Phe Leu
        115                 120                 125

Val Asn Val Pro Ala Leu Asn Thr Phe Ile Ala Asn Asp Thr Ala Pro
130                 135                 140

Glu Ala Gln Ile Asp Cys Lys Gln Cys Lys Ile His Asp Gly Phe Ser
145                 150                 155                 160

Lys Ala Phe Thr Glu Thr Trp His Asn Ile Gly Asp Leu Leu Glu Gln
                165                 170                 175

His Leu Asp Ser Tyr Pro Asp Tyr Gln Leu Tyr Val Thr Gly His Ser
            180                 185                 190

Leu Gly Ala Ala Met Ala Leu Leu Gly Ala Thr Ser Ile Lys Leu Arg
        195                 200                 205
```

```
Gly Tyr Asp Pro Ile Leu Ile Asn Tyr Gly Gln Pro Arg Val Gly Asn
            210                 215                 220

Lys Ala Phe Ala Asp Tyr Ile Ser Ala Leu Trp Phe Gly Asn Gly Asp
225                 230                 235                 240

Gly Leu Glu Ile Asn Gln Gln Arg Arg Leu Tyr Arg Met Thr His Trp
            245                 250                 255

Asn Asp Val Phe Val Gly Leu Pro Asn Trp Asp Gly Tyr Thr His Ser
            260                 265                 270

Asn Gly Glu Val Tyr Ile Lys Gly Lys Tyr Val Asn Pro Pro Leu Lys
            275                 280                 285

Asp Val Phe Ser Cys Ala Gly Gly Glu Asn Ser Lys Cys Tyr Arg Ser
290                 295                 300

Glu Phe Asn Leu Leu Ala Gln Ile Asn Leu Leu Gln Asn His Leu Cys
305                 310                 315                 320

Tyr Ile Asp Tyr Ile Gly Phe Cys Ala Leu Asn Val Gly Arg Arg Glu
                325                 330                 335

Leu Asn Asp Leu Pro His Tyr Asn Gly Pro Tyr Lys Tyr Gly His Lys
            340                 345                 350

Thr Glu Glu Gln Phe Ile Ala Glu Gly Leu Glu Leu Ser Asn
            355                 360                 365

<210> SEQ ID NO 74
<211> LENGTH: 371
<212> TYPE: PRT
<213> ORGANISM: Yarrowia lipolytica

<400> SEQUENCE: 74

Met Val Ser Leu Ser Ala Arg Ile Lys Asp Phe Phe Ser Val Leu Leu
1               5                   10                  15

Leu Gly Ala Ala Thr Ile Thr Pro Ser Thr Gln Thr Ala Gly Val Ser
            20                  25                  30

Gln Gly Phe Tyr Asp Phe Ala Arg Asp Phe Ala His Leu Ser Asn Ile
        35                  40                  45

Ala Tyr Cys Val Asn Ala Pro Ile Thr Pro Leu Asn Pro Asp Phe Thr
50                  55                  60

Cys Gly Asn Ser Cys Lys His Phe Pro Glu Ile Glu Leu Val Lys Thr
65                  70                  75                  80

Phe Gly Gly Asn Phe Phe Lys Thr Ser Ile Thr Gly Tyr Leu Ala Val
                85                  90                  95

Asp His Val Lys Lys Glu Lys Tyr Val Val Phe Arg Gly Thr Phe Ser
            100                 105                 110

Leu Ala Asp Ala Ile Thr Asp Met Gln Phe Gln Leu Ser Pro Phe Leu
        115                 120                 125

Val Asp Val Pro Ala Leu Asn Thr Phe Ser Ala Asn Asp Thr Thr Ala
130                 135                 140

Glu Ala Gln Thr His Cys Glu Gly Cys Lys Ile His Asp Gly Phe Ser
145                 150                 155                 160

Lys Ala Phe Thr Glu Thr Trp Gly Asn Ile Gly Glu Asp Leu Gln Lys
                165                 170                 175

His Leu Asp Ala Asn Pro Asp Tyr Gln Leu Tyr Val Thr Gly His Ser
            180                 185                 190

Leu Gly Ala Ala Met Ala Leu Leu Gly Ala Thr Ser Ile Lys Leu Lys
        195                 200                 205

Gly Tyr Asp Pro Ile Leu Ile Asn Tyr Gly Gln Pro Arg Val Gly Asn
210                 215                 220
```

```
Lys Pro Phe Ala Glu Phe Ile Asn Lys Leu Trp Phe Gly Glu Gly Asn
225                 230                 235                 240

Gly Leu Glu Ile Thr Pro Glu Arg Lys Leu Tyr Arg Met Thr His Trp
                245                 250                 255

Asn Asp Ile Phe Val Gly Leu Pro Asn Trp Glu Gly Tyr Thr His Ser
            260                 265                 270

Asn Gly Glu Val Tyr Ile Asn Asn Arg Phe Ile Asn Pro Pro Leu Lys
        275                 280                 285

Asp Val Ile Ser Cys Ala Gly Gly Glu Asn Ser Lys Cys Tyr Arg Ser
    290                 295                 300

Ser Phe Ser Leu Leu Ser Gln Ile Asn Leu Leu Gln Asn His Leu Ala
305                 310                 315                 320

Tyr Ile Asp Tyr Ile Gly Tyr Cys Ala Leu Asn Ile Gly Arg Arg Glu
            325                 330                 335

Leu Ala Asp Gln Glu His Tyr Thr Gly Pro Tyr Tyr Tyr Gly His Arg
            340                 345                 350

Ser Glu Glu Asp Phe Lys Lys Leu Gly Leu Glu Leu Ser Thr Pro Gln
            355                 360                 365

Val Glu Asn
    370
```